(12) United States Patent
Meana et al.

(10) Patent No.: US 7,566,552 B2
(45) Date of Patent: Jul. 28, 2009

(54) PROTECTION AGAINST ENVIRONMENTAL TOXICITY THROUGH MANIPULATION OF THE PROCESSING OF MESSENGER RNA PRECURSORS

(75) Inventors: Oscar Vicente Meana, Valencia (ES); Marta Roldan Medina, Valencia (ES); Ramon Serrano Salom, Valencia (ES); José Javier Forment Millet, Valencia (ES); Miguel Angel Naranjo Olivero, Valencia (ES); Roc Ros Palau, Valencia (ES); Rodolpho Arthur Kahnonou, Valencia (ES)

(73) Assignee: CropDesign N.V., Ghent (BE)

( * ) Notice: Subject to any disclaimer, the term of this patent is extended or adjusted under 35 U.S.C. 154(b) by 878 days.

(21) Appl. No.: 10/258,148

(22) PCT Filed: Apr. 19, 2001

(86) PCT No.: PCT/EP01/04479

§ 371 (c)(1),
(2), (4) Date: Dec. 16, 2002

(87) PCT Pub. No.: WO01/81599

PCT Pub. Date: Nov. 1, 2001

(65) Prior Publication Data

US 2004/0203157 A1    Oct. 14, 2004

(30) Foreign Application Priority Data

Apr. 19, 2000    (ES) .................................. 200001102

(51) Int. Cl.
| | |
|---|---|
| *C12N 15/00* | (2006.01) |
| *A01H 5/00* | (2006.01) |
| *C07K 14/00* | (2006.01) |
| *C12N 15/11* | (2006.01) |

(52) U.S. Cl. ................... 435/69.1; 435/320.1; 530/350; 800/298; 536/23.1

(58) Field of Classification Search ........................ None
See application file for complete search history.

(56) References Cited

U.S. PATENT DOCUMENTS 6,281,412 B1 *  8/2001  Murata ........................ 800/288

FOREIGN PATENT DOCUMENTS

| | | |
|---|---|---|
| EP | 1 033 405 | 9/2000 |
| WO | WO 92/21747 | 12/1992 |

OTHER PUBLICATIONS

Leutwiler et al. Nuc. Acids. Res. 1986; 14(10):4051-64.*
Bond, EMBO J. 1988; 7:3509-18.*
Check, Erika, Feb. 13, 2003, Nature, 421: 678.*
Forment et al. Plant J. 2002; 30(5): 511-19.*
Graveley et al. Mol. Cell. 1998; 1:765-71.*
Hastings et al. RNA, 2001; 7:471-82.*
Kmiec, American Scientist, 1999; vol. 87: 240-147.*
Shinozaki et al. Curr. Opin. Plant Bio. 2003; 6:410-17.*
Wang et al. Planta. 2003; 218: 1-14.*
Gravely, 2000, RNA 6:1197-1211.*
Lopato et al., 1996, PNAS 93; 3074-3079.*
Maiti et al., 1997, Transgen. Res., 6:143-156.*
Doelling et al., 1995, Plant J. 8:683-692.*
Donald et al., 1990, EMBO J. 9:1717-1726.*
Chen et al., 2000, Sex. Plant Reprod. 13:85-94.*
Benfrey et al.,1990, Science 250:959-966.*
Kim et al., 1994, Plant Mol. Biol. 24:105-117.*
Arrillaga et al. (1998) "Expression of the yeast HAL2 gene in tomato increases the in vitro salt tolerance of transgenic progenies" *Plant Science* 136(2):219-226.
Dichtl et al. (1997) "Lithium toxicity in yeast is due to the inhibition of RNA processing enzymes" *The EMBO Journal*, vol. 16, No. 23:7184-7195.
Nakamura et al. (1998) "*Arabidopsis thaliana* genomic DNA, chromosome 5, P1 clone: MNJ8" *EMBL* Accession No. AB017069.

* cited by examiner

*Primary Examiner*—Nancy Vogel
(74) *Attorney, Agent, or Firm*—Ann R. Pokalsky, Esq.; Dilworth & Barrese, LLP

(57) ABSTRACT

This invention describes the identification of pre-messenger RNA processing as a novel target of environmental stress caused for example by lithium and sodium toxicity. Overexpression of different types of proteins (or protein fragments) from different organisms but all involved in pre-mRNA processing, protects yeast from salt stress, which indicates that any stimulation of this process, independently of its mechanism, may counteract the toxic effects of mineral salts. A similar phenotype of tolerance to NaCl and to LiCl has been observed by overexpression of these types of proteins in transgenic *Arabidopsis* plants, demonstrating the generality of this protective effect in eukaryotic cells and organisms.

29 Claims, 11 Drawing Sheets

A

Figure 1:
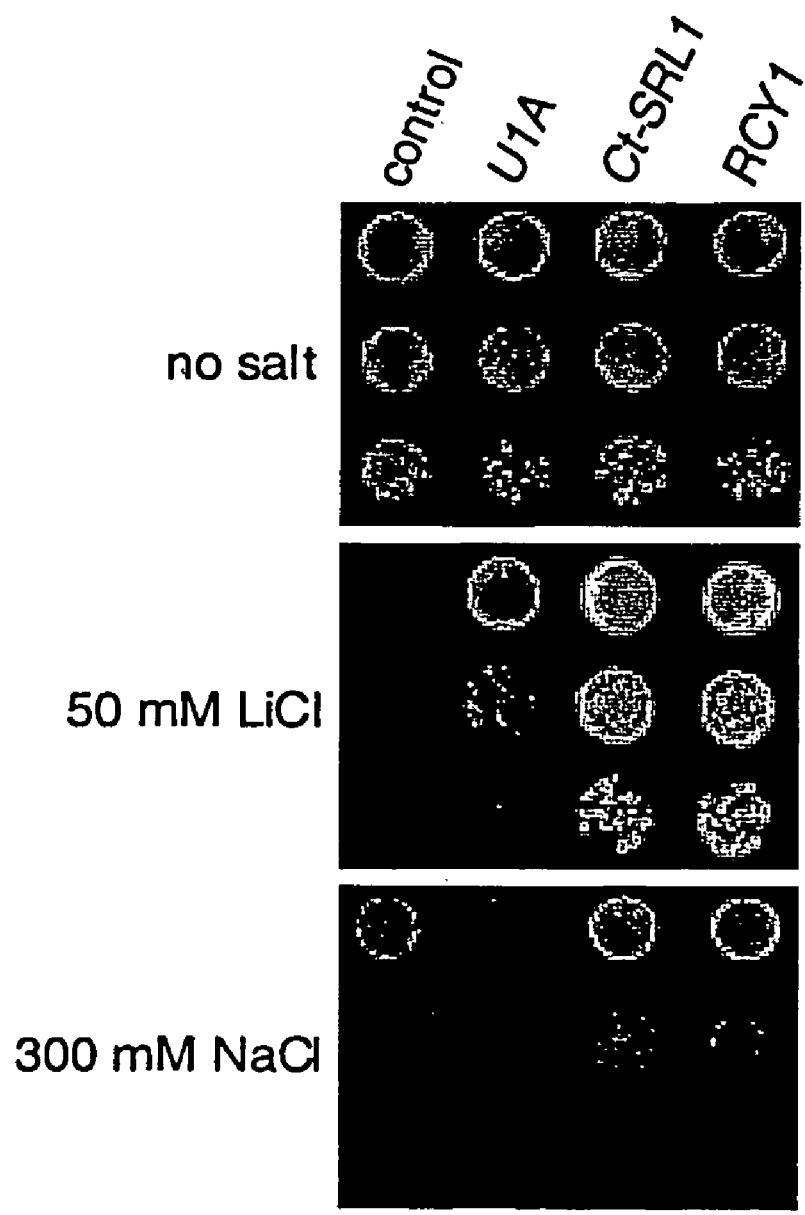

MIYTAIDNFYLTDEQLKASPSRKDGIDETTEISLRIYGCDLI
QEGGILLKLPQAVMATGQVLFQRFYCKKSLAKFDVKIVA
ASCVWLASKLEENPKKARQVIIVFHRMECRRENLPLEHL
DMYAKKFSELKVELSRTERHILKEMGFVCHVEHPHKFIS
NYLATLETPPELRQEAWNLANDSLRTTLCVRFRSEVVAC
GVVYAAARRFQVPLPENPPWWKAFDADKSSIDEVCRVL
AHLYSLPKAQYISVCKDGKPFTFSSRSGNSQGQSATKDL
LPGAGEAVDTKCTAGSANNDLKDGMVTTPHEKATDSKK
SGTESNSQPIVGDSSYERSKVGDRERESDREKERGRER
DRGRSHRGRDSDRDSDRERDKLKDRSHHRSRDRLKDS
GGHSDKSRHHSSRDRDYRDSSKDRRRHH

B

MNLPTKPSGSTGDMTRGSEDTARRPPSVKASLSVSFGQ
RAPHRASTRGSSPVRRPPPTGYDRNGGDEVQQRSPRR
SQSRDYYSDRDSDRQREREREKDRERERGRDRYRERE
RDYGNDRRSRRDYDSRSRRNDYEDDRSRHDRRSRSRS
RSRSRSVQIEREPTPKRDSSNKEKSAVTVNSNLAKLKDL
YGDASSQKRDEGFGTRKDSSSEEVIKLGGSSWR

FIGURE 2

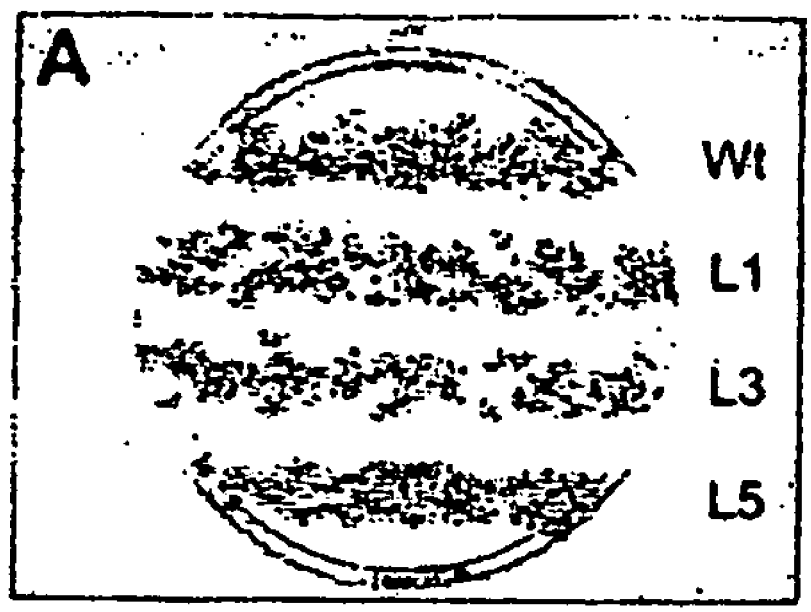
FIGURE 4

Figure 5

SEQ ID NO. 1: nucleotide sequence of Ct-SRL1(840 nucleotides). The Ct-SRL1 encoding region ranges from position 15 to 678 (start and stop codon are underlined)

```
CAAACCTTGA GAAGATGAAT TTACCAACTA AACCTTCTGG TTCAACCGGA
GACATGACCC GTGGCTCAGA AGACACTGCC CGTCGTCCAC CATCAGTAAA
AGCATCTCTC TCTGTTTCAT TTGGTCAGCG TGCACCTCAT CGTGCTTCCA
CCAGAGGCTC TTCTCCTGTT CGCCGTCCTC CACCGACTGG TTATGACAGA
AATGGAGGCG ATGAAGTACA ACAGCGGTCC CCACGTAGAA GCCAGAGCCG
AGACTATTAT TCTGACAGAG ACTCAGATAG ACAACGGGAA AGAGAGAGGG
AGAAAGACCG CGAAAGAGAG AGGGGGAGGG ATAGATACAG AGAAAGGGAG
AGGGATTATG GTAATGATAG GAGATCAAGG CGCGACTATG ATAGTAGAAG
CAGGCGCAAT GATTATGAGG ACGACAGAAG TAGACATGAC CGGAGAAGCA
GGAGCAGAAG CAGAAGTAGG AGCAGGAGTG TGCAGATTGA GCGTGAACCG
ACTCCTAAAA GAGATAGTAG CAACAAAGAG AAATCGGCGG TGACAGTGAA
CAGCAATCTC GCAAAGCTAA AAGATTTGTA TGGAGACGCA AGTAGTCAGA
AAAGGGATGA AGGATTTGGA ACAAGGAAAG ATTCAAGTTC AGAAGAAGTG
ATAAAGCTTG GTGGTTCCTC TTGGAGGTGA AAAAACAAAC AAAACAAAAC
CAAACTGTGG ATTTAAAATG CTTCTTCTAT TTAGCAGGAT GATGCATGTT
GTTTAACTAT ACTGTTTTGA TTTCCAGCAA ACTATTTGTC ATATGCTTTA
TATTACAGTT TAAGAGTTGA TCTTTATCTT GAAAAAAAAA
```

SEQ ID NO. 2: nucleotide sequence of RCY1 (1433 nucleotides). The putative RCY1 encoding region ranges from position 14 to 1262 (putative start and stop codon are underlined)

```
GTTTAGTGAA TCGATGATTT ACACTGCTAT CGACAATTTT TACCTAACCG
ACGAGCAGCT GAAGGCTTCA CCTTCGAGGA AAGATGGGAT AGATGAAACA
ACTGAAATCT CTCTTAGAAT CTATGGATGT GATCTCATCC AAGAGGGTGG
AATATTGCTC AAACTACCAC AGGCAGTTAT GGCTACTGGG CAGGTTCTGT
TTCAGCGATT CTATTGCAAG AAGTCTTTGG CTAAATTTGA TGTCAAGATA
GTTGCTGCCA GCTGTGTATG GCTTGCATCA AAACTGGAAG AAAACCCTAA
AAAAGCTAGA CAGGTCATCA TCGTATTCCA CAGGATGGAG TGTCGCAGGG
AGAACTTGCC ATTAGAACAT CTGGATATGT ATGCCAAGAA GTTCTCTGAG
TTGAAAGTTG AATTAAGCAG AACTGAGAGA CATATACTGA AAGAGATGGG
TTTTGTTTGT CATGTTGAAC ATCCTCACAA GTTCATATCA AACTACCTTG
CCACATTAGA AACACCTCCA GAATTGAGGC AAGAAGCTTG GAATTTGGCC
AATGATAGTC TGCGTACAAC CCTCTGTGTA AGGTTCAGAA GTGAGGTTGT
GGCTTGTGGG GTAGTGTATG CTGCTGCCCG TAGGTTTCAA GTACCACTCC
CTGAGAATCC GCCGTGGTGG AAAGCATTTG ATGCAGATAA ATCTAGTATT
GACGAAGTGT GTAGAGTTCT TGCTCATTTA TACAGTCTTC CAAAGGCTCA
GTATATCTCT GTTTGCAAGG ATGGGAAGCC ATTTACATTT TCTAGCAGAT
CCGGGAATTC TCAAGGTCAA TCAGCGACAA AGGATCTGTT GCCGGGAGCA
GGCGAGGCTG TTGATACTAA ATGTACTGCA GGATCAGCTA ATAACGACTT
GAAGGATGGA ATGGTTACTA CACCACACGA AAAGGCTACA GATTCCAAGA
AAAGTGGTAC CGAGTCAAAC TCTCAGCCAA TTGTAGGAGA CTCAAGCTAT
GAAAGAAGTA AAGTAGGAGA TAGAGAAAGA GAGAGTGATA GAGAGAAGGA
ACGAGGTAGA GAGAGGGACA GGGGTAGGTC TCACAGAGGC AGAGATTCTG
ACAGAGACAG TGATAGGGAG AGAGACAAAC TCAAAGATCG AAGTCATCAT
```

Figure 5 (Cont.)

```
CGGTCAAGAG ACAGATTGAA GGATTCAGGT GGACATTCAG ATAAATCAAG
GCATCATTCT TCTCGGGACC GTGACTACCG CGACTCATCG AAAGACCGTC
GTAGGCACCA TTAAGCCAAT CTTCTTGTCA TCTACATCCC CTTGAGCCTA
CTTGATGTTA AGACAGTATA GTGTTGTATT GTGTTAAGAG TCAAAACCCA
TGTGTACTTA ATCACATGCT AAGATCACGT TGGTTCGACA TATAAATCGA
GAAAGTCTGA TATGTTTCTA AAAAAAAAAA AAA
```

SEQ ID NO. 3: protein sequence of Ct-SRL1 (221 amino acids)

MNLPTKPSGSTGDMTRGSEDTARRPPSVKASLSVSFGQRAPHRASTRGSSPVRRPPPTGYDR
NGGDEVQQRSPRRSQSRDYYSDRDSDRQREREREKDRERERGRDRYRERERDYGNDRRSRRD
YDSRSRRNDYEDDRSRHDRRSRSRSRSRSRSVQIEREPTPKRDSSNKEKSAVTVNSNLAKLK
DLYGDASSQKRDEGFGTRKDSSSEEVIKLGGSSWR

SEQ ID NO.4: putative protein sequence of RCY1 (416 amino acids) The boxed square corresponds to SEG ID No.21. The underlined sequence corresponds to SEQ ID No. 22

MIYTAIDNFYLTDEQLKASPSRKDGIDETTEISLRIYGCDLIQEGGILLKLPQAV

SEQ ID NO. 5: nucleotide sequence of U1A (920 nucleotides). The U1A encoding region ranges from base 30 to base 782 (putative start and stop codon are underlined).

```
ccacgcgtcc gagagatttg gtgaagacga tggagatgca agaggctaat
caaggaggag gatcggaggt ttctccgaat cagacgattt acatcaacaa
tctcaacgaa aaagtgaagc ttgatgagct gaagaaatcg ctgaatgcag
tgttctctca gttcgggaag atactggaga tattggcgtt taagaccttt
aagcacaaag gacaagcttg ggtagtcttc gacaacaccg agtctgcttc
cactgctatt gctaaaatga ataattttcc tttctacgac aaggagatga
gaatacaata tgccaaaaca aaatcagatg ttgttgccaa ggccgatggt
acatttgttc ctcgcgagaa gagaaagaga catgaggaga aaggaggcgg
caagaaaaag aaagaccagc accatgattc tacacagatg ggcatgccca
tgaactcagc atatccaggt gtctatggag ctgcacctcc tctatcgcaa
gtaccatacc ctggtggcat gaaacccaat atgcccgagg caccagctcc
gccaaataat attctctttg tccaaaacct tcctcacgag acaactccaa
tggtgcttca gatgttgttc tgccagtacc aaggatttaa ggaagttaga
atgattgaag ccaaaccggg aatcgccttt gtggagtttg ctgatgagat
gcagtcgacg gtcgcaatgc agggacttca aggtttcaag attcagcaaa
accagatgct catcacgtat gccaagaaat agacaatttc gtttttatttg
tgtttcgatg agatatgttt gtatctgtca atgttacttc ttgccatggg
ggctgtcttc tgggttgtgt gatgctagat atccctctct acttacattt
tttcatcaaa aaaaaaaaa
```

Figure 5 (Cont.)

SEQ ID NO.6: putative protein sequence of U1A (250 amino acids)

MEMQEANQGGGSEVSPNQTIYINNLNEKVKLDELKKSLNAVFSQFGKILEILAFKTFKHKGQ
AWVVFDNTESASTAIAKMNNFPFYDKEMRIQYAKTKSDVVAKADGTFVPREKRKRHEEKGGG
KKKKDQHHDSTQMGMPMNSAYPGVYGAAPPLSQVPYPGGMKPNMPEAPAPPNNILFVQNLPH
ETTPMVLQMLFCQYQGFKEVRMIEAKPGIAFVEFADEMQSTVAMQGLQGFKIQQNQMLITYA
KK

SEQ ID NO.7: protein sequence of Beta vulgaris (1492 nucleotides) The putative coding sequence ranges from position 51 to 1079 (putative start and stop codon are underlined)

TCCTCTCTTTTAACCTAATTTGAGCTCTCATTATCCTGATTTTTTCAACC<u>ATG</u>GATGCTCAG
AGAGCTCTTCTCGATGAATTAATGGGCGCAGCTCGAAATCTGACTGATGAAGAAAAGAAAGG
TTATAGAGAGATAAAGTGGGATGACAAGGAAGTTTGTGCGCCGTAtATGATTCGATTTTGCC
CTCACGATCTCTTCGTCAATACTCGAAGTGATCTTGGACCATGTCCAAGAGTTCATGACCAA
AAGCTGAAAGAGAGCTTTGAGAACTCTCCAAGGCATGACTCATATGTCCCACGTTTTGAAGC
AGAGCTTGCCCAATTTTGTGAGAAGCTGGTGGCAGATTTGGATAGGAAAGTAAGACGTGGGA
GAGAGCGGCTGGACCAGGAGGTTGAACCTCCACCTCCCCCTCCTATTTCTGCAGAAAAAGCT
GAGCAGCTATCTGTACTTGAAGAGAAAATAAAAAATTTGCTTGAACAAGTAGAGTCACTGGG
AGAAGCTGGCAAAGTCGATgAAGCAGAAGCACTCATGCGAAAGGTGGAAAGTCTTAATTTAG
AGAAAGCTGCATTAACTCAACAGCCCCAGAATGCAGCAACAATGCTTACCCAAGAGAAAAAG
ATGGCACTATGTGAAATTTGCGGTTCCTTCCTGGTAGCCAATGATGCTGTGGAAAGAACTCA
ATCTCATATAACTGGCAAGCAGCATATTGGCTATGGCATGGTCCGTGATTACCTTGCTGAGT
ATAAGGAGGCTAAGGAGAAGGCAAGAGAAGAGGAAAGATTAGCAAGGGAGAAAGAAGCAGAA
GAACGTCGGAAGCAGAGGGAAAAGGAAAATGAGAGTAAAAACAGAAGAAGCATCTCCAGTGA
GAGGGACCGTCATCGTGATAGGGATTATGGCCGAGATCGTGAAAGATCACGAGAATGGAACA
ATAGGGGGAATCGAGACGAGGGAAGAGGAATGGATCGGAGAAGGCAATATGATCGCAATGGA
AGGGATGGAGGGAGGAATACGTATCATGGTCGTGAACGTGAAAGGAGCAGGTCACGGTCCCC
TGTTAGGCATGGCCACCGGAGGTGATCTAAGAGTGCTGGTTGCCGATATTAGTAGGCAGTGG
GTTGTGTAGATAAACGATGATCTTAAACCTACTGAGGTAGATGCTTTATATCTCAAGATGTT
TTGTGTCTGTTTTCGAGGTGTTGCATTGCAGTCTTATTGGGGGTTAAACTTTTCTTTATTGT
CCCACAGTGTTGAGACTATACTGTCTCCTCTCATCAATCTTGTTAGAGGTCAAAGAGATTGA
GGTAGGTAAAACTTCATCGTTGTAATCTTACCTATAGTCAACTTGAGTTTTGTCCAATTATA
GCACATGGTCTTTGAAACATTTTTTAATCATGCGGGGTACGCAAGAAAATATGCAACTATG
CTGCATGGCTTGTGTGCAAAAAAAAAAAAAAAAAAAAAAACTCGAGGGGGGCCCGGTACCA
AGAT

SEQ ID NO. 8: putative protein sequence of Beta vulgaris (342 amino acids )

MDAQRALLDELMGAARNLTDEEKKGYREIKWDDKEVCAPYMIRFCPHDLFVNTRSDLGPCPR
VHDQKLKESFENSPRHDSYVPRFEAELAQFCEKLVADLDRKVRRGRERLDQEVEPPPPPPIS
AEKAEQLSVLEEKIKNLLEQVESLGEAGKVDEAEALMRKVESLNLEKAALTQQPQNAATMLT
QEKKMALCEICGSFLVANDAVERTQSHITGKQHIGYGMVRDYLAEYKEAKEKAREEERLARE
KEAEERRKQREKENESKNRRSISSERDRHRDRDYGRDRERSREWNNRGNRDEGRGMDRRRQY
DRNGRDGGRNTYHGRERERSRSRSPVRHGHRR

Figure 5 (Cont.)

SEQ ID NO.9: nucleotide sequence of Beta vulgaris (650 nucleotides) The putative coding sequence ranges from position 14 to 625 (putative start and stop codon are underlined)

```
ACGAACAACAAAAATGGCGGCAGCAGATGTTGAAGCAGTAGACTTCGAACCTGAAGAAGATG
ATCTCATGGACGAAGATGGCGGTGCGGCTGAAGCTGACGGCTCTCCTCGAGCTCCTCACCCT
AAGATTAAATCAGCCATTACTGGCGCCGGAGCTCCATCTTCTGGCGGCTTCGGAGCTAAGAA
AACTAAAGGTCGCGGCTTCCGTGAAGACGCCGATgCTGAGCGTAACAGCCGTATGACTGCTC
GTGAATTTGATTCTCTTGACTCCGATgGTGGACCTGGTCCTGCTCGATCAATTGAGGGCTGG
ATTATACTTGTCACGGGAGTGCATGAAGAGGCTCAAGAAGAGGATCTCCTTAATGTCTTTGG
AGAGTTTGGCCAGCTTAAGAATTTGCATTTGAATCTGGATCGTCGTACTGGGTTTGTCAAGG
GTTATGCATTGATCGAGTATGAGAAGTTTGAAGAAGCACAAGCTGCAATAAAGGAGATGAAT
GGTGCCAAAATGCTTGAGCAGCCGATAAATGTTGATTGGGCATTCTGCAATGGTCCTTACAG
GAGGAGGGGCAACCGAAGAAGATCCCCACGTGGTCACCGATCAAGGAGTCCTAGAAGAAGAT
ATTAAATCTGTTTGCTGCATGTGGAAGTTG
```

SEQ ID NO. 10: putative protein sequence of Beta vulgaris (203 amino acids )

```
MAAADVEAVDFEPEEDDLMDEDGGAAEADGSPRAPHPKIKSAITGAGAPSSGGFGAKKTKGRGFRED
ADAERNSRMTAREFDSLDSDGGPGPARSIEGWIILVTGVHEEAQEEDLLNVFGEFGQLKNLHLNLDR
RTGFVKGYALIEYEKFEEAQAAIKEMNGAKMLEQPINVDWAFCNGPYRRRGNRRRSPRGHRSRSPRR
RY
```

SEQ ID NO.11: nucleotide sequence of Beta vulgaris (1464 nucleotides). The putative coding sequence ranges from position 51 to 1119 (putative start and stop codon are underlined)

```
TTTTGTAGCATTTGATTTTTGCTGAAAAACCCAATTCATATTTTGAAGAAATGACAACAATG
AACCCTTTTGATTTGTTGGGTGACAATGATAACGATGACCCATCTCAGCTTTTAGAGTCTGC
AACTGCTCAGTTGCAGAAAATTGCTGTTAAAAAAACCCCAACTCAGGTTGCTCAACAACCTC
AGCAACAGAAAGCTGCAAAGTTACCCACCAAACCTCTTCCTCCAACTCAAGCTGTCCGGGAG
GCAAAGAATGATTCCCAGCGCGGAGGGGGCGTGGAGGAGGTCGCGGTAGTGGCCGTGGGCG
TGGTGGATACAATAGGGACTACTCAAACAATGAAAATGCTTTTAACAGCACTGGAGTAACTG
GCAGTCAAGGGGATGATGGGGAAAGGGAAAGGCGACCTTATGCGGGACCTCGTGGCCCTTAT
CGTGGTGGTCGCCGAGATGGGTTCAACAATGAGGAGGGAAGAGACGGGGAACGCCCGCGTAG
AACCTATGAGCGACGAAGTGGGACTGGGCGTGGAAGTGAGATCAAACGTGAGGGAGCAGGAC
GTGGAAACTGGGGTGCTGAATCAGATGAAGTTGCACCGGTTACTGAGGAAGCTGGAGAACAA
AATGAGAAGAAGTTGAACCCTGAGAATCTTCCAGCTGTAGAAGATGCTGCTGATGGCATCAA
GGAGGGCCAGCCAGAtGAGACTGAAGAAAAGGAACCAGAGGAAAAGGAGATGACACTTGAAG
AGTATGAGAAGTTGCTGGAAGAGAAGAGGAAGGCTTTATCAGCACTCAAGGCTGAGGAACGC
AAGGTGGAGGTTGACAAAGATTTCGAGTCCATGCAACAGCTTATAAACAAAAAAAAGGATGA
AGACTCAGTTTTCATCAAATTGGGTTCTGACAAGGATAAGAAGAAGGAAGCAGCTGAAAAGG
AGAAAGTGAAGAAGTCTGTCAGCATTAATGAATTTCTGAAGCCTGCTGAAGGGGATAGATAT
GGTGGTCGTGGCAGGGGACGTGGTCGTGGCCCAAGAGGTGGTGGATATGGTGGAGGTAATAG
GATGTTTAGTACGTCTGCTCCAGCAATCGAAGATCCAGGGGAGTTCCCAACCCTAGGTGGCA
AGTGAGGCCACATCTTTGAACTTTGGtCTCTATTTGGGGTTTTACTTGACCCCCTCTGATTT
```

Figure 5 (Cont.)

```
TAAGTCATTTGAGTGACAGGAATGGACTTCCAGCTGTGGGTTTCCTGTACCAAATCCACTTT
TAAGAAAATTTTTATGCTTTTTAAATTTGTATATTTATTCTGTTAAAAAAAAAAAAAAAAAC
TCGTGCCGAATTCGATATCAAGCTTATCGATACCGTCGACCTCGAGGGGGGGCCCGGTACCA
AGATGGCCTTTGGTGGGTTGAAGAAGGAAAAAGACAGAAACGACTTAATTACCTACTTGAAA
AAAGCCTGTGAGTAAACAGGCCCCTTTTCCTTTGTCGA
```

SEQ ID NO. 12: putative protein sequence of Beta vulgaris (356 amino acids)

```
MTTMNPFDLLGDNDNDDPSQLLESATAQLQKIAVKKTPTQVAQQPQQQKAAKLPTKPLPPTQ
AVREAKNDSQRGGGRGGGRGSGRGRGGYNRDYSNNENAFNSTGVTGSQGDDGERERRPYAGP
RGPYRGGRRDGFNNEEGRDGERPRRTYERRSGTGRGSEIKREGAGRGNWGAESDEVAPVTEE
AGEQNEKKLNPENLPAVEDAADGIKEGQPDETEEKEPEEKEMTLEEYEKLLEEKRKALSALK
AEERKVEVDKDFESMQQLINKKKDEDSVFIKLGSDKDKKKEAAEKEKVKKSVSINEFLKPAE
GDRYGGRGRGRGRGPRGGGYGGGNRMFSTSAPAIEDPGEFPTLGGK
```

SEQ ID NO.13: nucleotide sequence of Beta vulgaris (1310 nucleotides). The putative coding sequence ranges from position 51 to 1121 (putative start and stop codon are underlined)

```
CCGACAAGTTAGGGTTTTTCCAAGGGTTTTCTGAAAAACAGCGAATAACAATGGCAACCACT
AACCCTTTCGACTTGCTCGACGACGATgCTGAGGACCCAGCCCTCCTTATTGCTGCGCAGGA
GCAGAAGGTTTCCGCCGTCGTTGCCGGAGATAAGAAAACTCCGGCAGTCGCTGCTAAGCCTG
CTAAACTCCCTACTAAGCCTCTTCCTCCTTCTCAAGCTGTGAGAGAGGCAAGGAATGATGGT
GGTCGTGGTGGAGGTGGCCGCGGGGCCGTGGTTATGGGCGGGGACGTGGTCCAGGTGGACC
TAATAGAGATTCAACAAATAATGATGAAATATATCCCAACGAGAATGGGGGTTCTATGGGAT
ATAGGGAGGACAGAGATAAGCCATCTGAAAGACGTGGAGGATATGGCGGTCCTCGTGGTGGT
TATCGTGGAGGACGACGTGGAGGTTATGATAATGGAGAAGCTGCTGAAGGAGAACGTCCTAG
GAGGATGTATGAACGCCGTAGTGGCACTGGACGAGGAGGTGAGATTAAACGTGAGGGTTCTG
GTCGTGGAAACTGGGGATCTCCTACTGATGAGATAGCTCCGGAGACTGAAGAACCTGTTGTG
GAAAATGAAGCAGCTGTTGCAGCTGATAAGCCAGCAGGAGAGGGAGAAAATGTTGATGCTGA
AAAGGAGAGTCAAGAGAAGGAAGTTGTAGAAGCAGAGCCTGAAGAAAAGGAAATGACTCTTG
AGGAGTATGAGAAGGTATTGGAGGAGAAGAGGAAGGCCTTGCTATCATTGAAAGGGGAGGAA
AGAAAGGTGGATTTGGACAAGGAGTTTGAATCTATGCAGCTGGTTTCAAAGAAGAAGAATGA
TGATGAGGTTTTCATAAAGCTGGGTTCTGATAAGGACAAGAGAAAGGAGGCTGCAGAAAGAG
AAGAAAGGTCCAAGAAGTCTGTGAGCATCAATGAATTTCTTAAGCCTGCCGAGGGTGACGGA
TACCACAGGCGTGGAAGAGGAAGAGGCCGTGGTGGTAGGGGAGGCTATGGTGGAGGATACGG
CATGAACAATGCATCTGCTCCTTCTATTGAGGATCCCAATCAATTCCCATCTTTGGGTGCGA
ACTGAGTTTTTGTCCGTTGTTGTCTTAGTTATTTTTGGGTCTTTCTTATATTTTGAGACTTA
TTTATGATGTTCAGGAGCCTCATCAATTACAAAAAAAGATATTTGACAGGAATAATGTGTTT
TTCCTGTGTTAAGAGTGTAAATCTTAGATGTTTCATCTTTCAAAAAAAaAAAAAAAAACTCG
AGGGGGGG
```

SEQ ID NO. 14: putative protein sequence of Beta vulgaris (356 amino acids)

```
MATTNPFDLLDDDAEDPALLIAAQEQKVSAVVAGDKKTPAVAAKPAKLPTKPLPPSQAVREA
RNDGGRGGGGRGGRGYGRGRGPGGPNRDSTNNDEIYPNENGGSMGYREDRDKPSERRGGYGG
PRGGYRGGRRGGYDNGEAAEGERPRRMYERRSGTGRGGEIKREGSGRGNWGSPTDEIAPETE
EPVVENEAAVAADKPAGEGENVDAEKESQEKEVVEAEPEEKEMTLEEYEKVLEEKRKALLSL
KGEERKVDLDKEFESMQLVSKKKNDDEVFIKLGSDKDKRKEAAEREERSKKSVSINEFLKPA
EGDGYHRRGRGRGRGGRGGYGGGYGMNNASAPSIEDPNQFPSLGAN
```

Figure 5 (Cont.)

SEQ ID NO.15: nucleotide sequence of Beta vulgaris (1155 nucleotides). The putative coding sequence ranges from position 2 to 970 (putative start and stop codon are underlined)

```
GATGGACGAGAATTATATTCGTACTTGTTTCGCTCAATCCGGCGAGCTTGTTAATGTTAAAA
TCATCCGTAATAAGCAAACCATGCAGTCAGAGTGCTATGGATTTATTGAGTTTTCCACCCAT
GCTGCTGCTGAAAGGATTTTGCAGACTTACAATAACACCTTGATGCCAAATGTTGAGCAAAA
CTACAGACTGAATTGGGCTTTCTATGGATCTGGTGAGAAGCGTGGAGAGGATGCTTCTGATT
ATACAATTTTTGTTGGGGATTTAGCTCCAGATGTTACTGATTACACATTGCAAGAGACATTT
AGAGTTCGCTATCCATCTGTAAAAGGTGCTAAGGTTGTGATAGATAGACTGACAAGTAGATC
AAAGGGTTATGGATTTGTTCGTTTCGGAGATGAAAGTGAACAAGCACGTGCCATGTCAGAGA
TGAATGGAATGATGTGCTTAGGCCGTGCAATGCGTATTGGAGCAGCTGCAAACAAGAAAAGT
GTTGGCGGAACAGCTTCATATCAGAATAATCAGGGAACTCCAAATGACAGTGATCCGAGTAA
CACTACTATATTTGTTGGCAATTTGGATTCTAATGTGACTGATGAACATTTGAGACAAACAT
TTAGCCCTTACGGAGAATTGGTCCATGTAAAAATTCCTGCGGGCAAACAGTGCGGGTTTGTT
CAATTTACTAACAGAAGTAGTGCTGAGGAAGCATTGAGGGTATTGAACGGAATGCAATTAGG
CGGACGAAATGTTAGACTTTCGTGGGGCCGTAGTCCTAACAACAGACAGTCTCAACCTGACC
AGAACCAGTGGAACAATGCTGCTTATTATGGTTATCCTCAAGGATACGACTCTTATGGATAT
GTATCTGCTCCTCAAGACCCAAACATGTACTATGGTGGCTACCCTGGTTATGGTGGTTACGC
GATGCCTCAGCAGGCTCAGATGCCATTGCAACAACAGTGATCTACCTTATGCCAAGCAGGAG
AGGTCGGTTGCCAGGGAGCTGTCATTGTACTTGGAGGCTGAGCTTCTGGAGTTGGATGATTC
CTCCCAGAGATGGCAGAATGTAGTATAACTTGGTCATTGTGCTGGTCGAATTTTATTTACTG
TCTTGGGTTTTTGCTCTGTGCTGCTTTTTTGTAGCTTGC
```

SEQ ID NO. 16: putative protein sequence of Beta vulgaris (322 amino acids).

```
MDENYIRTCFAQSGELVNVKIIRNKQTMQSECYGFIEFSTHAAAERILQTYNNTLMPNVEQN
YRLNWAFYGSGEKRGEDASDYTIFVGDLAPDVTDYTLQETFRVRYPSVKGAKVVIDRLTSRS
KGYGFVRFGDESEQARAMSEMNGMMCLGRAMRIGAAANKKSVGGTASYQNNQGTPNDSDPSN
TTIFVGNLDSNVTDEHLRQTFSPYGELVHVKIPAGKQCGFVQFTNRSSAEEALRVLNGMQLG
GRNVRLSWGRSPNNRQSQPDQNQWNNAAYYGYPQGYDSYGYVSAPQDPNMYYGGYPGYGGYA
MPQQAQMPLQQQ
```

SEQ ID NO.17: nucleotide sequence of Beta vulgaris (1200 nucleotides). The putative coding sequence ranges from position 35 to 922 (putative start and stop codon are underlined)

```
AAAAACCTCTTTTTCTCTCTCCTAAATCACAACAATGGCGATACTCTCAGATTACGAGGAAG
AAGAACACCAACCACAACCAGAAAAGAAGCAACCTTCAAAGAAATTTTCAGCAACTTTCGAT
CCTTCGAATCCGCTAGGGTTTCTTCAATCTACTCTCGAATTCGTCTCAAAAGAGTCCGATTT
TTTCGCTAAGGAATCATCTGCGAAAGATGTTGTTTCTCTGGTTCAGAAAGTGAAGGAGAAGT
ACATTGAAGAAGTAGAGAATAAGAAGAAGAAGCTTCTAGATGAATCTGCCGCTGCCGCCGCC
GCCGCCGCTGCTGCTGCTGCGTCGTCGTCTTCATCTGATTTGGAGAAGAAGGTTGATGATAA
TGAGAGTGCGGAAGAGACAGAGAAATCTAAGTACAAAGCTCCAAACAGTGGGAATGGTCAAG
ATCTCGAGAACTACTCATGGATACAGTCCTTGCAAGAAGTTACTGTTAATGTTCCTGTTCCA
CCTGGAACAAAGTCTAGGTTTATCGATTGTCAGATAAGAAGAATCATCTGAAAGTTGGCCT
CAAGGGTCAGCCTCCCATCATCGATGGTGAACTGTTCAAGCCTGTTAAGCCAGATGATTGTT
```

Figure 5 (Cont.)

```
TTTGGAGTTTGGAGGATCAAAAGTCAATCTCTATGCTGCTAACAAAGCATGATCAAATGGAG
TGGTGGAGAAGTCTGGTCAAAGGTGAACCTGAAATCGACACTCAGAAGGTTGAACCTGAGAG
CAGTAAGCTGTCTGACTTGGACCCTGAAACAAGGTCAACTGTTGAGAAGATGATGTTTGACC
AAAGGCAAAAATCCATGGGCTTGCCCACAAGTGATGATATGCAGAAGCAAGACATGCTGAAG
AAGTTCATGTCCGAGCATCCGGAAATGGACTTTTCTAACGCGAAGTTTAACTAGATATCGAT
GTCGGTGATGGACTATGATTTTTTGGGTGGCAAATTCTCGAAACAGGAACTGAAGAAAGCTT
TTGTTATGTCTAATACTGAGCTTGTTCATAGTAGTTACAGTCTCTAGGGTAGATGTCTCATG
AAGAGGGGAACATTGCTTTTTGTTTAACTCTTATTTATATGCAAGTGATATTCGGTTTGCTA
AGCAGTACATTCGTGCATCCTGCGCTTGATTCGGGTCCTGTTCAATCATATATGTAATGTTA
TAGCTGCAAAAAAAAAAAAAAA
```

SEQ ID NO. 18: putative protein sequence of Beta vulgaris (295 amino acids)

```
MAILSDYEEEEHQPQPEKKQPSKKFSATFDPSNPLGFLQSTLEFVSKESDFFAKESSAKDVV
SLVQKVKEKYIEEVENKKKKLLDESAAAAAAAAAAAASSSSSDLEKKVDDNESAEETEKSKY
KAPNSGNGQDLENYSWIQSLQEVTVNVPVPPGTKSRFIDCQIKKNHLKVGLKGQPPIIDGEL
FKPVKPDDCFWSLEDQKSISMLLTKHDQMEWWRSLVKGEPEIDTQKVEPESSKLSDLDPETR
STVEKMMFDQRQKSMGLPTSDDMQKQDMLKKFMSEHPEMDFSNAKFN
```

SEQ ID NO.19: nucleotide sequence of mus musculus (1050 nucleotides). The putative coding sequence ranges from position 37 to 969 (putative start and stop codon are underlined)

```
GAAAAGAGAGGAGAGAGAAAACCAAAATCAACAAAAATGGCGGAACATCTAGCATCGATATT
CGGGACAGAGAAAGACAGAGTGAACTGTCCATTCTACTTCAAGATCGGAGCTTGTAGACATG
GAGATCGTTGCTCAAGGCTTCATACTAAGCCTAGTATTAGCCCTACTTTGTTGCTTGCTAAT
ATGTATCAACGCCCTGATATGATTACTCCTGGTGTTGATCCTCAAGGACAGCCTCTTGATCC
TCGCAAAATTCAACAACATTTTGAGGATTTTTATGAGGATTTATTTGAGGAACTAAGCAAGT
ATGGGGAGATTGAAAGTCTCAACATCTGTGACAATTTGGCTGACCACATGGTTGGGAATGTT
TATGTGCAGTTCAGAGAGGAAGAACATGCTGGCGAgGCACTACGAAACTTGAGTGGAAGATT
TTATGCCGGTCGTCCAATCATTGTTGATTTTTCTCCTGTAACGGACTTCAGAGAAGCAACCT
GCAGACAGTATGAGGAAAATGTGTGCAATCGTGGAGGTTACTGCAACTTTATGCATTTGAAA
AAAATTAGCAGGGAGCTTAGGCGACAGTTGTTTGGAAGGTACAGAAGGAGGCATAGCCGTAG
TAGAAGTCGCAGTCCTCAAGCACATCGGGGGCATGGAGATCGTCCACATGGTGGCCGTGGTT
ATGGTAGAAGAGATGATGATAGAAATCAGCGGTACCATGACAAGGGAAGAAGGCCTAGAAGC
CGTAGCCCTGGGCATAGAGGACGAAGCAGAAGCCCTCCCGGCAGGAGGGATAGGAGTCCAGT
GAGGGAGAATAGTGAGGAGAGAAGAGCAAAGATTGCACAATGGAACAGGGAAAAGGAACAGG
CAGACACTGGTAATAACGATGTTAATCATGATGTCACTGACAACCATGCAAATGGATTTCAG
GACAATGGGGAGGATTACTATGACCATCCTCAGCAGTAACTGGATGAAGTGCACAAGCAGGC
TTTATTCACTACTTCTGGTTTGCTGTTATCAGAGTCTGCTCGTTTGCAGGATTTTTCG
```

SEQ ID NO. 20: putative protein sequence of mus musculus sequence (310 amino acids)

```
MAEHLASIFGTEKDRVNCPFYFKIGACRHGDRCSRLHTKPSISPTLLLANMYQRPDMITPGV
DPQGQPLDPRKIQQHFEDFYEDLFEELSKYGEIESLNICDNLADHMVGNVYVQFREEEHAGE
ALRNLSGRFYAGRPIIVDFSPVTDFREATCRQYEENVCNRGGYCNFMHLKKISRELRRQLFG
RYRRRHSRSRSRSPQAHRGHGDRPHGGRGYGRRDDDRNQRYHDKGRRPRSRSPGHRGRSRSP
PGRRDRSPVRENSEERRAKIAQWNREKEQADTGNNDVNHDVTDNHANGFQDNGEDYYDHPQQ
```

PROTECTION AGAINST ENVIRONMENTAL TOXICITY THROUGH MANIPULATION OF THE PROCESSING OF MESSENGER RNA PRECURSORS

FIELD OF THE INVENTION

This invention refers to the use of nucleic acids and proteins involved in the processing of messenger RNA precursors for the enhancement of of tolerance to environmental stress such as mineral salt toxicity in eukaryotic cells and organisms.

BACKGROUND TO THE INVENTION

The nature of the cellular targets sensitive to lithium and sodium toxicity represents an important gap in our knowledge on the physiology of ion homeostasis in eukaryoUc cells. The characterisation of these targets is essential for the understanding of clinical problems such as the effects of lithium on the therapy for dipolar disorder [Schou (1997) *Arch, Gen. Psychiatry* 54, 9] or high sodium levels associated with hypertension [Lifton (1996) *Science* 272, 676). Another problem, completely different but also related to ionic homeostasis, is the progressive salinisation of cultivated lands subjected to intensive irrigation, which has turned crop plant breeding for salt tolerance into an urgent need for the development of a sustainable agriculture in arid regions [Serrano (1996) *Int. Rev. Cytol.* 165; 1; Yeo (1998) *J. Exp. Bot.* 49, 915; Holmberg & Bülow (1998) *Trends Plant Sci.* 3, 61].

Apart from ion transport [Haro et al. (1991) *FEBS Lett.* 291, 189; Gaxiola et al. (1999) *Proc. natl. Acad. Sci. USA* 96, 1480; Apse et al. (1999) *Science* 285, 1256] and osmolyte synthesis [Tarczynski et al (1993) *Science* 259, 508; Kishor et al. (1995) *Plant Physiol.* 108, 1387: Alia et al. (1998) *Plant J.* 16, 155], the manipulation of cellular systems most sensitive to high ion concentrations and to water stress offers alternative routes to improve salt tolerance of crop plants [Serrano (1996) *Int. Rev. Cytol.* 165, 1; Tezara et al. (1999) *Nature* 401, 914].

Genetic and biochemical analyses have allowed to identify the product of the yeast gene HAL2 as an important physiological target of salt toxicity [Gläser et al. (1993) *EMBO J.* 12, 3105; Dichtl et al. (1997) *EMBO J.* 16, 7184]. HAL2 encodes a 3',5'-biphosphate nucleotidase, which is very sensitive to inhibition by lithium and sodium [Murguía et al. (1995) *Science* 267, 232]. Salt inhibition of Hal2p results in the intracellular accumulation of 3'-phosphoadenosine 5'-phosphate (pAp) [Murguía et al. (1996) *J. Biol. Chem.* 271, 29029], a toxic compound which in turn inhibits the reactions of reduction and transfer of sulphate groups, as well as some exoribonucleases [Dichtl et al. (1997) *EMBO J.* 16, 7184; Gil-Mascarell et al. (1999) *Plant J.* 17, 373]. There are genes homologous to HAL2 in plants [Gil-Mascarell et al. (1999) *Plant J.* 17, 373] and in mammals [López-Coronado et al. (1999) *J. Biol. Chem.* 274, 16043] although in the latter case the encoded enzyme is inhibited by lithium but not by sodium.

The salt tolerance conferred by overexpression of Hal2p, the wild-type protein as well as mutated versions resistant to lithium and sodium, is relatively modest [Albert et al. (2000) *J. Mol. Biol.* 295, 927]. This suggests the existence of additional targets of salt toxicity, which become limiting once the HAL2 bottleneck is overcome, but the nature of these important salt-sensitive processes is not yet known.

Two patent applications relating to osmotic stress but describing protective mechanisms different to the general mechanism described in the present invention are the following: ES2110918A (1998-02-16) relating to the production of plants tolerant to osmotic stress through the manipulation of carbohydrate metabolism and ES2134155A1 (1998-10-07) relating to a method to confer tolerance to osmotic, water and salt stress in glycophylic plants, through the use of genes encoding proteins with peroxidase activity.

SUMMARY OF THE INVENTION

The technical problem underlying the present invention is to provide a method that can be used to enhance stress tolerance of cells and organisms that suffer from stress conditions like osmotic stress, caused by salt, drought or cold and freezing stress.

A solution to this technical problem is achieved by providing protection against osmotic stress in cells and organisms through the manipulation of the processing of messenger RNA. Provided by the present invention is at set of isolated genes that are able to confer to a heterologous host cell or host organism tolerance to stress conditions. These genes are all involved in the processing of mRNA precursors (such as synthesis, splicing, 5' and 3' end modification, movement, transport to the cytoplasm, metabolism etc. . . ) and they all showed a salt resistance phenotype when separately transformed to a salt sensitive yeast mutant. By doing so each gene acted as an efficient enhancer of stress tolerance, without the assistance of additional factors.

This set of genes, comprising SR-like proteins, (nuclear) RNA binding factors, components of ribonucleoprotein complexes, transcription factors, and nuclear movement proteins, enables the person skilled in the art to genetically alter the organism of interest in order to make it tolerant to stress situations such as osmotic stress situations, more particularly mineral salt or Na+ or Li+ toxicity. Each of the disclosed genes enables the person skilled in the art to modify cell fate and/or plant development and/or biochemistry and/or physiology by introducing at least one of these genes into the cell. For the cultivation of crop plants for example, of which many are sensitive to stress conditions like salt, drought or cold, the disclosed genes offer the possibility to solve the problem of reduced yield and reduced economic profit.

This invention offers a solution to cellular toxicity caused by environmental stress through the manipulation of the processing of messenger RNA precursors and the embodiments of the invention comprise methods, nucleic acids, polypeptides, vectors, host cells and transgenic organisms like transgenic plants.

DETAILED DESCRIPTION OF THE INVENTION

Soil salinity is one of the most significant abiotic or environmental stresses for plant agriculture. Apart from the practical goal of genetically improving the salt tolerance of crop plants, salt tolerance research represents an important part of basic plant biology. Also research on two other major abiotic stresses, drought and cold, is intimately linked with salt stress work. For example, many genes that are regulated by salt stress are also responsive to drought or cold stress (Zhu J. K., 1997, *Molecular aspects of osmotic stress in plants, CRC Crit. Rev. Plant Sci.* 16 253-277). A person skilled in the art thus can assume that when an isolated gene confers salt tolerance to a host organism when transfected herein, it could also confer cold and/or drought stress tolerance. Salt, drought and cold are considered to be the three most important forms of osmotic stress.

In order to identify novel targets of environmental toxicity in eukaryotic cells, the inventors characterised genes conferring an increase in the tolerance to mineral salts when expressed in yeast cells. Therefore, cDNA libraries from *Arabidopsis thaliana* [Minet et al. (1992) *Plant J.* 2, 417] and *Beta vulgaris* were searched which could confer tolerance to salt stress by overexpression in yeast cells, in which accumulation of pAp, and its toxic effect, was avoided by addition of methionin to the culture medium[Gläser et al. (1993) *EMBO J.* 12, 3105; Dichtl et al. (1997) *EMB J.* 16, 7184; Murguía et al. (1995) *Science* 267, 232; Murguía et al. (1996) *J. Biol. Chem.* 271, 29029]. The result of this strategy has given rise to the present invention. This is a functional approach to identify genes and proteins that are involved in the response of plants to salt stress. For this purpose cDNA expression libraries were constructed as described in example 1 and example 3 and competent yeast strains (see example 2) were used to screen cDNAs that increased the yeast salt tolerance upon overexpression. The growth of these yeast strains is normally inhibited at high NaCl or LiCl concentrations of (150 mM) similar to those impairing growth of most crop species. After transforming the yeast cells with the cDNA library, colonies were pooled and selected for their ability to grow in the presence of 150 mM NaCl. This screening procedure is further described in example 4.

Isolation of *Arabidopsis thaliana* Genes that Enhance Salt Tolerance

A cDNA library from the plant *Arabidopsis thaliana* of ca $7,5 \times 10^5$ transformants, was screened and three independent clones were isolated which were able to confer tolerance to high salt concentrations in yeast (FIG. 1). Surprisingly, these three cDNAs encode proteins implicated in the processing of messenger RNA precursors. These three proteins were named Ct-SRL1, RCY1 and U1A.

Two of these proteins belong to the family of the so-called "SR-like" or "alternating arginin-rich" factors, defined by having a domain with a high content in Arg residues alternating with Ser, Asp, andlor Glu (RS domain) (FIG. 2). Members of this family have been involved in constitutive and/or alternative splicing, and in the coupling of different steps during processing and metabolism of messenger RNA (transcription, modifications at the 5' and 3' ends, and pro-mRNA splicing, transport of mature RNA to the cytoplasm, etc.). The Ct-SRL1 protein, with amino acid composition as set forth in SEQ ID NO. 3, is encoded by the cDNA identified herein as SEQ ID NO.1, which can also be found on the genomic region of *Arabidopsis thaliana* chromosome 5, P1 clone MNJ8 (Genbank accession number AB017069). Also the protein sequence of SEQ ID. NO. 3 is present in the public database under the accession number BABO9109 but no function was assigned to this sequence.The cDNA of Ct-SRL1 is not full-length and it encodes the carboxy-terminal end of a putative SR-like protein, which includes the RS domain. Its expression in yeast confers tolerance to lithium and sodium (FIG. 1).

Figure 3:
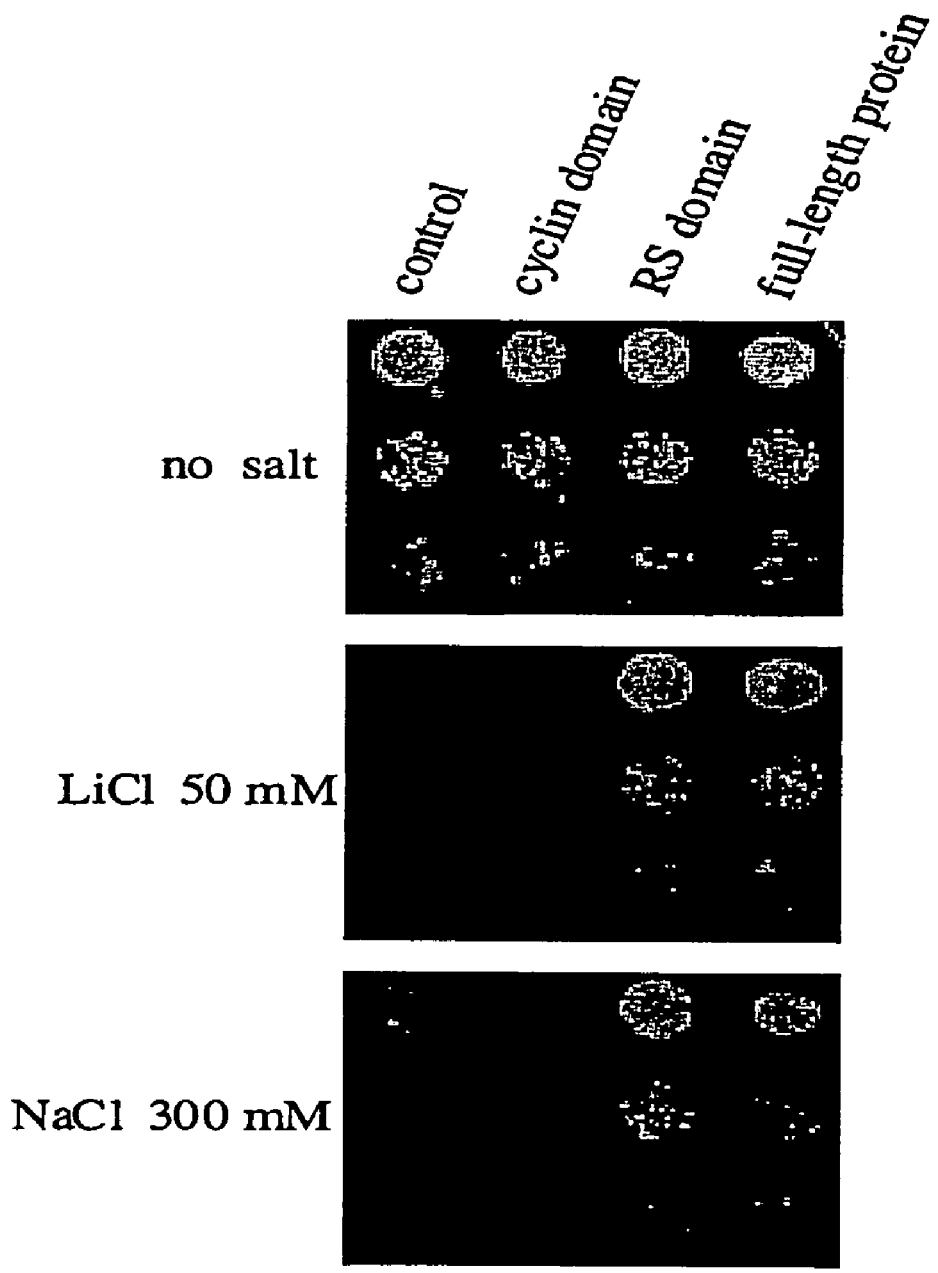

The second clone encodes a putative protein with an N-terminal cyclin domain related to those of K-type and T-type cyclins and with an arginin-rich domain at the C-terminus (FIG. 2 A). This SR-like protein was named RCY1 for altering arginin-rich cyclin 1. Its expression in yeast conferred tolerance to lithium and sodium (FIG. 1) To determine the role of the RS-domain in this SR-like protein for the enhancement of salt tolerance in yeast, the cyclin domain and the RS domain of RCY1 were separately cloned and transformed into yeast cells. The division of both domains is marked in FIG. 2A by the underlined methionin residue and the C-terminal part, containing the RS domain is referred to as SEQ ID NO. 21 (FIG. 5). The expression of only the RS domain confers the same phenotype as expression of the full-length protein (FIG. 3). These results demonstrate that, in the case of "SR-like" factors, it is the expression of the RS domain per se, and not of a specific protein, which confer salt stress tolerance. The amino acid composition of RCY1 protein is represented herein as SEQ ID NO. 4. The cDNA of RCY1 is identified herein as SEQ ID NO. 2 and this sequence can be found on the genomic region of *Arabidopsis thaliana* chromosome II sequence from clone T9J22. The nucleotide sequences of this genomic *Arabidopsis thaliana* clone, that corresponds to a part of the nucleotide sequence of the RCY1 gene, is annotated as a putative cyclin (accession number AAC14513.1). This protein prediction from the public database, lacks the first 55 amino acids of the RCY1 protein. As such, the fragment of the RCY1 protein corresponding with the amino-terminal region is represented in SEQ ID NO 22.

The third *Arabidopsis* clone encodes a U1A protein from *Arabidopsis*, a component of the U1-snRNP, the ribonucleoprotein complex which recognises the 5'-splice site in one of the first steps in the processing of introns of the pre-messenger RNA. The U1A protein of *Arabidopsis* is previously described by Simpson et al (1995, *EMBO J.* 14: 4540-4550) as a specific component of the spliceosomal U1-snRNP. The expression of U1A in yeast conferred weaker LiCl tolerance and no tolerance to NaCl (FIG. 1). The U1A protein, with amino acid composition as set forth in SEQ ID NO 6, is encoded by the cDNA identified herein as SEQ ID. NO. 5. The protein sequence as well as the nucleic acid sequence can be found in the public database under the accession numbers CAA90283.1 and Z49991 respectively and are fully annotated. The sequences described above are presented in FIG. 5.

The phenotypes as described above were observed in the presence and absence of methionine, and in different genetic backgrounds.

The improvement of salt tolerance by expression of the *Arabidopsis* clones was not due to the stimulation of ion transport in yeast, since it was not associated to changes in the intracellular lithium concentrations. This was determined as described in example 5. Also the phenotypes were maintained in a yeast strain defective in vacuolar transport.

The above-mentioned data suggested that an impact on another cellular process was responsible for the observed stress tolerance. The inventors believed that processing of messenger RNA precursors could be a target, of ionic toxicity in eukaryotic cells. This has not been described previously.

In agreement herewith, the inventors have confirmed that processing of introns of pre-mRNAs is inhibited in yeast in the presence of, for example, lithium chloride. Two independent tests for pre-mRNA splicing in vivo supported this invention. First, the inventors have measured the specific activity of the enzyme β-galactosidase synthesised in yeast cells from a plasmid containing the *E. coli* LacZ gene artificially interrupted by an intron (example 6). They detected a decrease in the accumulation of this enzyme, as compared to that produced from the control construct without intron, when LiCl is added to the culture medium. Simultaneous expression of the RS domain of *Arabidopsis* SRL1 in these yeast cells partially blocked the observed inhibition (data not shown). These results have been confirmed by the second assay, in which the inventors determined directly, by the RT-PCR technique as described in example 7, the inhibition of splicing in the presence of lithium. The accumulation of endogenous yeast messenger RNA precursors in the presence of LiCl, for example the pre-mRNA corresponding to the SAR1 gene, was demonstrated. Because a general inhibition of splicing would first affect the removal of those introns normally processed with lower efficiency, the inventors choose for these experiments the SAR1 pre-mRNA, which contains such an intron (Kao and Siliciano, 1996, Mol. Cell. Biol. 16: 960-967). Here again, the inventors observed the accumulation of SAR1 pre-mRNA by incubating yeast cells under salt stress conditions, and how it was partially reversed by simultaneous co-expression of Ct-SRL1. In this way the inventors demonstrated that the inhibition of processing precursor mRNA in the presence of salt is partially reverted by expression of one of the *Arabidopsis* clones mentioned before (e.g. Ct-SRL1).

The general significance of the present invention was corroborated by the phenotype of transgenic *Arabidopsis* plants, which overexpressed the Ct-SRL1 cDNA. Supporting the general character of the mechanism, the expression of the same Ct-SRL1 cDNA in under control of the CaMV 35S promoter *Arabidopsis* transgenic plants, increases their tolerance to NaCl and LiCl in a similar way as in yeast. This can be observed, for example, by germination of transgenic seeds in agar plates containing LiCl concentrations which are toxic to wild-type control seeds (FIG. 4). The three independent transgenic lines were able to grow indicating the efficiency of the method of the present invention.

From these results and from the very nature of the isolated *Arabidopsis* clones, it can be deduced that any stimulation of the processing of messenger RNA precursors, independently of the mechanism involved, counteracts the toxic effect of the salt, and that this protective effect against salt stress is general in all eukaryotic cells and organisms.

The universal character of the invention, namely that the protective effect against salt stress is not species-dependent, was confirmed by the isolation of sugar beet genes and eukaryotic genes which also confer salt tolerance and which were also related to the processing of messenger RNA precursors.

Isolation of *Beta Vulgaris* Genes that Enhance Salt Tolerance

Another aspect of the present invention is the procedure of screening a cDNA library from NaCl induced sugar beet leaves and subsequent isolation of the seven sugar beet genes that confer stress tolerance to yeast cells. A functional approach to identify sugar beet genes and proteins that are involved in the response of plants to salt stress was followed. For this purpose a NaCl-induced cDNA expression library was constructed from sugar beet leaves as described in example 1 and example 3 and the Na$^+$-sensitive yeast mutant strain JM26 (see example 2) was used to screen for sugar beet cDNAs that increased the yeast salt tolerance upon overexpression. The growth of this yeast mutant is normally inhibited at NaCl concentrations (150 mM) similar to those impairing growth of most crop species. After transforming the yeast cells with the cDNA library, colonies were pooled and selected for their ability to grow in the presence of 150 mM NaCl. This screening procedure is further described in example 4. Six positive clones which survived the high concentrations of salt, were further characterised and contained a gene with a sequence as in SEQ ID NO.7, SEQ ID NO 9, SEQ ID NO 11, SEQ ID NO. 13, SEQ ID NO. 15 or SEQ ID NO. 17. The corresponding protein sequences encoded by these genes have an amino acid composition as set forth in SEQ ID NO 8, SEQ ID NO. 10, SEQ ID NO 12, SEQ ID NO. 14, SEQ ID NO. 16 or SEQ ID NO. 18 respectively. All these sequences are presented in FIG. 5. Surprisingly, each of the six selected yeast clones are transformed by a gene that encodes a protein which is implicated in the processing of mRNA: one protein is a putative arginine-aspartate RNA binding protein, two are a putative RNA binding protein, two are a putative transcription factor and one shows similarity to a nuclear movement protein. Therefore these proteins (and the encoding genes) are suitable to be used as stress tolerance enhancers through the manipulation of pre-mRNA processing, as is described for the *Arabidopsis thaliana* genes of the present invention and as described above.

The selected genes and their encoded proteins are further described in the following paragraphs.

Accordingly, the invention relates to a novel isolated nucleic acid of red beet as set forth in SEQ ID NO. 7, encoding a putative arginine-aspartate RNA binding protein and capable of enhancing salt tolerance in yeast cells. The open reading frame, starting at nucleotide position 51 and ending at position 1079 encodes the amino acid sequence as set forth in SEQ ID NO. 8. This polypeptide has 76% identity and 86% similarity with the *Arabidopsis thaliana* putative arginin-aspartate RNA binding protein (Swiss prot accession number AAB68037). The amino acid comparison was done with the program GAP (Symbol comparison table: blosum62. cmp, CompCheck: 6430, BLOSUM62 amino acid substitution matrix, Reference: Henikoff, S. and Henikoff, J. G. (1992). Amino acid substitution matrices from protein blocks. Proc. Natl. Acad. Sci. USA 89: 10915-10919.). This program was also used for comparing the amino acid sequences of the following red beet polypeptides.

The invention also relates to a novel isolated nucleic acid of red beet as set forth in SEQ ID NO. 9, encoding a putative RNA binding protein and capable of enhancing salt tolerance in yeast cells. The open reading frame, starting at nucleotide position 14 and ending at position 625 encodes the amino acid sequence as set forth in SEQ ID NO. 10. This polypeptide has 68% identity and 78% similarity with the *Arabidopsis thaliana* putative RNA binding protein (Swiss prot accession number AAG52616.1).

The invention also relates to a novel isolated nucleic acid of red beet as set forth in SEQ ID NO. 11, further referred to as clone or sequence number 10, encoding a putative transcription factor and capable of enhancing salt tolerance in yeast cells. The open reading frame, starting at nucleotide position 51 and ending at position 1119 encodes the amino acid sequence as set forth in SEQ ID NO. 12. This polypeptide has 81% identity and 86% similarity with the *Spinacia oleracea* nuclear RNA binding protein (Swiss prot accession number AAF14145.1).

Nucleotides 1 to 475 from SEQ ID NO. 11 were published in the EST database under the accession number BF011019 with the description of a DNA fragments of a Sugar beet germination cDNA library and that is similar to a putative transcription factor.

The invention also relates to a novel isolated nucleic acid of red beet as set forth in SEQ ID NO. 13, encoding a putative transcription factor and capable of enhancing salt tolerance in yeast cells. The open reading frame, starting at nucleotide position 51 and ending at position 1121 encodes the amino acid sequence as set forth in SEQ ID NO. 14. This polypeptide has 81% identity and 87% similarity with the Spinacia oleracea nuclear RNA binding protein (Swiss prot accession number AAF14144.1).

The invention also relates to a novel isolated nucleic acid of red beet as set forth in SEQ ID NO. 15, encoding a putative RNA binding protein and capable of enhancing salt tolerance in yeast cells. The open reading frame, starting at nucleotide position 2 and ending at position 970 encodes the amino acid sequence as set forth in SEQ ID NO. 16. This polypeptide has 68% identity and 74% similarity with the Oryza sativa putative RNA binding protein (Swiss prot accession number AAG59664.1).

The invention also relates to a novel isolated nucleic acid of red beet as set forth in SEQ ID NO. 17, encoding an unknown type of protein and capable of enhancing salt tolerance in yeast cells. The open reading frame, starting at nucleotide position 35 and ending at position 922 encodes the amino acid sequence as set forth in SEQ ID NO. 18. This polypeptide has 61% identity and 69% similarity with the *Arabidopsis thaliana* protein with similarity to a nuclear movement protein (Swiss prot accession number BAA97317.1).

Accordingly, a preferred embodiment of the present invention relates to a method for induction of stress tolerance to an organism comprising the expression of a (or at least one) *Beta vulgaris* gene, which is involved in the processing of messenger RNA precursors.

Also the screening and selection procedure as described above can be used to select genes from other organisms than plants. As an example, a sequence of Mus musculus was selected that enhances salt tolerance in yeast cells. This sequences is set forth in SEQ ID NO. 19 and it encodes a putative small subunit of an U2 snRNP auxiliary factor protein and is capable of enhancing salt tolerance in yeast cells. The open reading frame, starting at nucleotide position 37 and ending at position 969 encodes the amino acid sequence as set forth in SEQ ID NO. 20. This polypeptide has 78% identity and 84% similarity with the *Arabidopsis thaliana* U2 snRNP auxiliary factor, small subunit (Swiss prot accession number BAB10638.1). This sequence is presented in FIG. 5.

This result illustrates that mammalian genes can also be use in the method of the present invention. The method of the present invention is thus generally applicable to confer stress tolerance to a host cell or organism through the manipulation of messenger RNA precursors.

The surprisingly strong phenotype of some of the yeast clones selected as described above and the fact that these genes in an isolated position and in a heterologous background acted as stress tolerance enhancers, makes these genes very attractive tools to induce stress tolerance in any organism of interest, without the need for accessory compounds. The ability of these genes to enhance osmotic stress tolerance, particularly mineral salt stress such as Na+ and Li+ stress in yeast cells when isolated and transfected herein, clearly demonstrates their potential to confer on their own osmotic stress tolerance to any heterologeous host organism. Alternatively, each of the stress tolerance genes of the present invention can be combined with another gene, in order to alter cell fate or plant morphology, plant development, plant biochemistry or plant physiology.

According to a first embodiment the present invention relates to a method to enhance stress tolerance in cells and organisms comprising the manipulation of the process of processing messenger RNA precursors.

According to a preferred embodiment, said stress could be environmental stress, such as but not limited to osmotic stress, salt stress, drought stress, cold or freezing stress.

According to a preferred embodiment, the methods of the invention relate to the enhancement of salt tolerance of cells and organisms.

Another embodiment of the invention relates to a method to protect cells and organisms against salt toxicity comprising the manipulation of the process of processing messenger RNA (mRNA) precursors.

According to one embodiment, one way of manipulating the process of processing messenger RNA precursors is by genetic or biochemical manipulation of at least one molecule which is involved in or which interferes with the process of processing messenger RNA precursors or with one of the pathways of processing mRNA precursors.

The term "cells" relates to any prokaryotic or eukaryotic cell. The term "organism" relates to any mono- or multicellular organism of prokaryotic or eukaryotic origin.

The present invention clearly describes several genes and proteins belonging to different classes of genes and proteins which can be used to enhance stress tolerance. These genes and proteins of the invention have been shown to have an effect on the process of mRNA processing.

Therefore, according to yet preferred embodiments, the invention relates to any of the above-mentioned methods wherein the genetic or biochemical manipulation of a protein possessing a domain with a high content in Arg-Ser, Arg-Glu and Arg-Asp dipeptides (RS domain), an RNA binding protein, a component of the U1-snRNP or the U2-snRNP complex, a transcription factor, or a nuclear movement protein is involved.

The invention also relates to the use of an isolated nucleic acid comprising a nucleic acid sequence as represented in SEQ ID NO 1 with an amino acid sequence as set forth in SEQ ID NO 3, or a nucleic acid as represented in SEQ ID NO 2 with an amino acid sequence as set forth in SEQ ID NO 4 or SEQ ID NO 21, or a nucleic acid encoding a polypeptide comprising the amino acid sequence represented in SEQ ID NO 22, for at least one, or in at least one, of the above described methods. SEQ ID NOs 1 and 2 share substantial homology with genes encoding SR-like proteins.

The invention also relates to an isolated nucleic acid comprising a nucleic acid sequence as represented in SEQ ID NO 5 with an amino acid sequence as set forth in SEQ ID NO 6 for any of the above described methods. SEQ ID No 5 shares substantial homology with genes encoding a component of the I1-snRNP or the U2-snRP complex.

The invention also relates to an isolated nucleic acid comprising a nucleic acid sequence as represented in any of SEQ ID NOs 7, 9, 11, 13, 15, 17 or 19, with an amino acid sequence as set forth in any of SEQ ID NO 8, 10, 12, 14, 16, 18 or 20 for any of the above-described methods. SEQ ID NOs 7, 9, 13 and 15 share substantial homology with genes encoding RNA-binding proteins. SEQ ID NO 19 shares substantial homology with genes encoding a component of the I1-snRNP or the U2-snRP complex. SEQ ID NOs 11 and 17 share substantial homology with genes encoding transcriptional factors.

The invention further relates to an isolated nucleic acid encoding a protein or an immunologically active and/or functional fragment of such a protein selected from the group consisting of:

a) a nucleic acid comprising a DNA sequence as given in any of SEQ ID NOs 1, 2, 5, 7, 9, 11, 13, 15, 17 or 19 or the complement thereof, b) Nucleic acid comprising the RNA sequence corresponding to any of SEQ ID NOs 1, 2, 5, 7, 9, 11, 13, 15, 17 or 19 as in (a) or the complement thereof, c) Nucleic acid specifically hybridizing tot the nucleotide sequence ad defined in (a) or (b), d) nucleic acid encoding a polypeptide or protein with an amino acid sequence which is at least 50%, preferably at least 60%, 70% or 80%, more preferably at least 85% or 90%, most preferably 95% identical to the polypeptide represented in any of SEQ ID NOs 3, 4, 6, 8, 10, 12, 14, 16, 18, 20or 21, e) nucleic acid encoding a polypeptide or protein comprising the amino acid sequence as given in any of SEQ ID NOs, 3, 4, 6, 8, 10, 12, 14, 16, 18, 20, 21 or 22, f) nucleic acid which is degenerated as a result of the genetic code to a nucleotide sequence of a nucleic acid as given in any of SEQ ID NOs 1, 2, 5, 7, 9, 11, 13, 15, 17 or 19 or as defined (a) to (e),
g) nucleic acid which is diverging due to the differences in codon usage between the organisms to a nucleotide sequence encoding a polypeptide or protein as given in any of SEQ ID NOs 3, 4, 6, 8, 10, 12, 14, 16, 18, 20 or 21 or as defined in (a) to (e),
h) nucleic acid which is diverging due to the differences in alleles encoding a polypeptide or protein as given in any of SEQ ID NOs, 3, 4, 6, 8, 10, 12, 14, 16, 18, 20 or 21 or as defined in (a) to (e),
i) nucleic acid encoding an immunologically active and/or functional fragment of a polypeptide or protein encoded by a DNA sequence as given in any of SEQ ID NOs 1, 2, 5, 7, 9, 11, 13, 15, 17 or 19 or as defined (a) to (e),
j) nucleic acid encoding a protein or polypeptide as defined in SEQ ID Nos, 3, 4, 6, 8, 10, 12, 14, 16, 18, 20 or 21 or as defined in (a) to (i) characterized in that said sequence is DNA, cDNA, genomic DNA or synthetic DNA.

It should be understood that the present invention also relates to any of the nucleic acids defined in a) to j) for use in any of the methods described earlier.

The invention further relates to a nucleic acid molecule of at least 15 nucleotides in length specifically hybridizing with, or specifically amplifying one of the nucleic acids of the invention, preferably those nucleic acids as defined in a) to j).

The invention also relates to a vector comprising a nucleic acid of the invention, wherein said vector preferably is an expression vector wherein the nucleic acid is operably linked to one or more control sequences allowing the expression of said sequence in prokaryotic and/or eukaryotic host cells. As such the invention also relates to a host cell containing a nucleic acid or a vector of the invention. Said host cell can be chosen from a bacterial, insect, fungal, yeast, plant or animal cell.

According to yet another embodiment, the invention relates to the use of a natural or synthetic nucleic acid encoding a protein containing an "RS domain" as defined earlier for use in any of the methods herein described.

The invention also relates to the use of a natural or synthetic nucleic acid encoding a protein involved in the process of processing messenger RNA precursors in eukaryotic cells in any of the methods of the invention.

The invention further relates to the use a nucleic acid with at least 50% identity to at least one of the sequences herein described in a method for enhancing stress tolerance comprising the manipulation of the process or pathway of processing mRNA precursors. Preferably said nucleic acid originates from an eukaryotic cell or organism.

Also comprised within the invention are anti-sense molecules corresponding to at least one of the nucleic acids of the invention and their use in any of the methods of the invention.

According to yet another embodiment, the present invention relates to a polypeptide encodable by at least one of the nucleic acids of the invention, or a homologue thereof or a derivative thereof, or an immunologically active and/or functional fragment thereof, said polypeptide being natural, synthetic, enriched, isolated, cell-free and/or recombinant. Each of these polypeptides can be used in any of the methods of the invention.

Preferred polypeptides are those comprising an amino acid sequence as given in any of SEQ ID NOs 3, 4, 6, 8, 10, 12, 14, 16, 18, 20, 21 or 22 a homologue thereof or a derivative thereof, or an immunologically active and/or functional fragment thereof.

The invention also relates to a method of producing a polypeptide of the invention comprising culturing a host cell as described earlier under the conditions allowing the expression of the polypeptide and recovering the produced polypeptide from the culture.

The invention also relates to a method for the production of transgenic plants, plant cells or plant tissues comprising the introduction of a nucleic acid of the invention in an expressible format or a vector of the invention in said plant, plant cell or plant tissue.

The invention also relates to a method for the production of altered plants, plant cells or plant tissues comprising the introduction of a polypeptide of the invention directly into a cell, a tissue or an organ of said plant.

The invention further relates to a method for effecting the expression of a polypeptide of the invention comprising the introduction of a nucleic acid of the invention operably linked to one or more control sequences or a vector of the invention stably into the genome of a plant cell.

The invention also relates to said methods for producing transgenic plants, further comprising regenerating a plant from said plant cell.

The invention further relates to a transgenic plant cell obtainable by one of the above-mentioned methods wherein said nucleic acid is stably integrated into the genome of said plant cell.

According to the invention, transgenic plants tolerant to salt stress can be produced as a result of the expression of at least one of the nucleic acids of claim 13 or at least one of the polypeptides of claim 25 or 26 or an anti-sense molecule of claim 23. Said transgenic plants are also part of the invention, as well as transgenic plants which as a result of the expression of at least one of the nucleic acids or antisense molecules of the invention or at least one of the polypeptides of the invention show an alteration of their phenotype.

The invention relates to any harvestable part of a plant of the invention which is preferably selected from the group consisting of seeds, leaves, fruits, stem cultures, rhizomes, roots, tubers and bulbs. Also the progeny derived from any of the plants or plant parts of the invention are part of the present invention.

According to another embodiment the invention relates to a method for enhancing stress tolerance in (a) plant(s) comprising expression of at least one of the nucleic acids or at least one of the polypeptides an anti-sense molecule of the invention in cells, tissues or parts of said plant(s).

According to another embodiment, the invention relates to a method for altering stress tolerance in (a) plant(s) comprising expression of at least one of the nucleic acids or at least one of the polypeptides or an ant-sense molecule of the invention in cells, tissues or parts of said plant(s).

It should be clear that the stress tolerance in the above methods can mean any stress caused by the environment such as, but not limited to osmotic stress, salt stress, drought stress, freezing stress or cold stress.

Furthermore, any of the methods, the nucleic acids, or antisense molecules or the polypeptides of the invention can be used (in a method) for increasing yield, for stimulating growth which can be in any part of that plant, such as root, leave, seed.

The invention also relates to a plant obtainable by any of the above described methods for culturing on soil with high salt concentrations, preferably soils with a salt content of more than 1 mM salt ions.

Also forming part of the invention are new strains of yeast or other unicellular eukaryotes more tolerant to salt stress as a result of the expression of any of the nucleic acids and/or proteins of the invention.

The invention further relates to an in vitro cell culture system comprising animal, plant or host cells as defined earlier, tolerant to salt, obtained as a result of the expression of at least one of the nucleic acids, vectors, polypeptides, or antisense molecule of claim 23.

The invention further relates to at least one therapeutic application in humans derived from the methods described herein.

The invention also relates to an antibody specifically recognizing a polypeptide of the invention or a specific epitope thereof.

The invention further relates to a diagnostic composition comprising at least a nucleic acid a vector, an antisense molecule, a polypeptide or an antibody of the invention.

DEFINITIONS AND ELABORATION TO THE EMBODIMENTS

Specific Definitions

"Manipulation of a process" herein means the interference with or the modulation of that process, preferably enhancing, catalysing, changing or altering that process. This interference can have an impact on every step or every component or every product or every result of that process. Also this interference can have an impact on the efficiency, the rate or the yield of that process.

"Genetic manipulation of a process" herein refers to the manipulation of a process by any kind of interfering with the genetic sequences (e.g. nucleotide sequences, RNA, DNA) that are involved in that process. Next to the natural genetic activity of the cell such as replication, transcription translation, and the processing of different nucleic acids, also molecular biology techniques and gentechnology techniques comprised in the term "genetic manipulation of a process". These artificial genetic techniques are know by the person skilled in the art and are for example cloning, transforming, recombining, expressing, overexpressing, silencing etc. As an example of "genetic manipulation of a process" one can interfere with the genetic sequence encoding a protein, which is involved in the process of processing messenger RNA precursors. Alternatively, one can interfere with an RNA molecule (such as a small nucleolar RNA), which is directly involved in the process of processing messenger RNA precursors.

In the case that said genetic sequence encodes a protein and the expression, the constitution, the structure or the location of that coding sequence is altered, the term "genetic manipulation of a protein" is used. More particularly one can alter the composition or the expression of said coding sequences or one can introduce or delete said coding sequence in the host cell, which performs said process. More specifically said protein can be any component which is involved in the processing of pre-mRNA, such as but not limited to a component of the U1-snRNP or U2-snRNP complex, a transcription factor, an RNA binding protein or a nuclear movement protein.

"Biochemical manipulation of a process" herein refers to the manipulation of said process by using biochemical methods that interfere with said process. With biochemical methods is meant the use of any substance (chemicals, peptides, and molecules) which have an impact on biological processes. For example one can introduce a peptide, or a protein, or a biochemical or a chemical substance in the cell performing that process, in order to interfere with that process. More particularly one can introduce a protein or a peptide derived from the genes of the present invention directly into the cell, in order to enhance the process of processing messenger RNA precursors.

In the case that said biochemical method involves the use of a protein or peptide or in case said biochemical method results in the modification of a protein, we use the term "biochemical manipulation of a protein".

"Cells" herein is to be taken in its broadest context and includes every living cell, such as prokaryotic and eukaryotic cells.

"Messenger RNA precursor" herein refers to any RNA molecule, which is not yet operational as a mature messenger RNA, from which polypeptides can be transcribed, because its composition, its structure or its location has to be changed. "Processing of messenger RNA precursors" herein refers to any process, which changes the composition, the structure or the location of a messenger RNA precursor. Examples of such processes in an eukaryotic cell are the synthesis of the messenger RNA precursor during the transcription, the modification of the 5' and/or the 3' ends of the precursor like polyadenylation, the splicing of introns from the precursor like the constitutive or the alternative splicing, the metabolism of precursor or the translocation of the precursor towards the nuclear envelop and the transport of the mature RNA to the cytoplams etc. Also the coupling of the different steps of this processing or metabolism of the precursor DNA are part of the term "processing of messenger RNA precursors" as used in this description. Post-transcriptional processing of precursor RNA comprises a complex pathway of endonucleolytic cleavages, exonucleolytic digestion and covalent modifications. The general order of the various processing steps is well conserved in eukaryotic cells, but the underlying mechanisms are largely unknown. The pre-mRNA processing is an important cellular activity and has been studied in the yeast cells Saccharomyces cerevisiae by Venema and Tollervey (Yeast, (1995) 11(16): 1629-1650). The processing steps involve a variety of protein-protein interactions as well as protein-RNA and RNA-RNA interactions. The precise role of different transcription factors, RNA binding proteins, and other nuclear proteins such as nuclear movement proteins and nuclear RNA's in the processing of pre-mRNA remains largely unknown. Therefor a protein interfering with the process of processing messenger RNA precursors, can be a protein of many different kinds. The nuclear transport of pre-mRNA involved several factors which can be used in the method of the present invention, since they are involved in the processing of pre-mRNA. Pre-mRNA is transcribed primarily from genes located at the interface between chromatin domains and the interchromatin space. After partial or complete processing and complexing with nuclear proteins, the transcripts leave their site of synthesis and travel through the interchromatin space to the nuclear pores, where they are captured by the export machinery for export to the cytoplasm. Transport-competent mRNA's are complexed with the correct complement of nuclear proteins (reviewed in Politz and Pederson, J. struct. Biol 2000, 129(2-3): 252-257). The role of the U1-snRNP and the U2-snRNP is mainly situated in the splicing of pre-mRNA. The product of the U1 small nuclear ribonucleoprotein particle or complex U1-snRNP 70K (U1-70K) gene, a U1 sn-RNP-specific protein, has been implicated in basic as well as alternative splicing or pre-mRNA in animals as well as in plants (Golovkin and Reddy, Plant Cell, 1996, (8): 1421-1435). In other reports different interacting proteins of the U1-70K protein are described, such as for example SC35-like protein and serine/arginine-rich protein (Golovkin and Reddy, J. Biol Chem 1999, 245(51): 36428-36438). For the U2 small nuclear ribonucleoprotein auxiliary factors such as U2A have been described (Domon et al, J. Biol Chem 1998: 273(51): 34603-34610). Within the scope of the present invention are any proteins, which are involved in splicing of the messenger RNA-precursors. The role of small nucleolar RNA's in the processing of pre-mRNA in plants has been described (Brown and Shaw, the Plant Cell, 1998, 10: 649-657). Therefor manipulation of the process of processing pre-mRNA can also be established by interfering with RNA molecules. Jarrous et al (J. Cell Biol. 1999, 146(3): 559-572) showed that Rpp29 and Rpp38 (protein subunits of human RNaseP) are found in the nucleolus and that they reside in coiled bodies, organelles that are implicated in the biogenesis of several other small nuclear ribonucleoproteins required for the processing of precursor mRNA. These kinds of proteins which are part of a Ribonucleoprotein Ribonuclease complex are involved in the processing of pre-mRNA can therefor also be used in the method of the present invention. The role of nuclear movement proteins is not well established in the art. Still a lot of molecules involved in the processing of messenger RNA precursors remain to be elucidated.

"SR-like proteins" as used herein are described previously in in Blencowe et al. 1999, 77(4): 277-291: "The processing of messenger RNA precursors (pre-mRNA) to mRNA requires a large number of proteins that contains domains rich in alternating arginine and serine residues (RS domains). These include members of the SR family of splicing factors and proteins that are structurally and functionally distinct from the SR family collectively referred to below as SR-related proteins. Both groups of RS domain proteins function in constitutive and regulated pre-mRNA splicing. Recently, several SR-related proteins have been identified that are associated with the transcriptional machinery. Other SR-related proteins are associated with mRNA 3' end formation and have been implicated in export". The evidence that proteins containing RS domains may play a fundamental role in the co-ordination of different steps in the synthesis and processing of pre-mRNA is further reviewed in Blencowe et al. 1999, 77(4): 277-291.

General Definitions

The terms "protein(s)", "peptide(s)" or "oligopeptide(s)" or polypeptide, when used herein refer to amino acids in a polymeric form of any length. Said terms also include known amino acid modifications such as disulphide bond formation, cysteinylation, oxidation, glutathionylation, methylation, acetylation, farnesylation, biotinylation, stearoylation, formylation, lipoic acid addition, phosphorylation, sulphation, ubiquitination, myristoylation, palmitoylation, geranylgeranylation, cyclization (e.g. pyroglutamic acid formation), oxidation, deamidation, dehydration, glycosylation (e.g. pentoses, hexosamines, N-acetylhexosamines, deoxyhexoses, hexoses, sialic acid etc.), acylation and radiolabels (e.g. $^{125}I$, $^{131}I$, $^{35}S$, $^{14}C$, $^{32}P$, $^{33}P$, $^{3}H$) as well as non-naturally occurring amino acid residues, L-amino acid residues and D-amino acid residues.

"Homologues" or "Homologs" of a protein of the invention are those peptides, oligopeptides, polypeptides, proteins and enzymes which contain amino acid substitutions, deletions and/or additions relative to the said protein with respect to which they are a homologue without altering one or more of its functional properties, in particular without reducing the activity of the resulting. For example, a homologue of said protein will consist of a bioactive amino acid sequence variant of said protein. To produce such homologues, amino acids present in the said protein can be replaced by other amino acids having similar properties, for example hydrophobicity, hydrophilicity, hydrophobic moment, antigenicity, propensity to form or break a-helical structures or β-sheet structures, and so on.

Substitutional variants of a protein of the invention are those in which at least one residue in said protein amino acid sequence has been removed and a different residue inserted in its place. Amino acid substitutions are typically of single residues, but may be clustered depending upon functional constraints placed upon the polypeptide; insertions will usually be of the order of about 1-10 amino acid residues and deletions will range from about 1-20 residues. Preferably, amino acid substitutions will comprise conservative amino acid substitutions, such as those described supra.

Insertional amino acid sequence variants of a protein of the invention are those in which one or more amino acid residues are introduced into a predetermined site in said protein. Insertions can comprise amino-terminal and/or carboxy-terminal fusions as well as intra-sequence insertions of single or multiple amino acids. Generally, insertions within the amino acid sequence will be smaller than amino or carboxyl terminal fusions, of the order of about 1 to 10 residues. Examples of amino- or carboxy-terminal fusion proteins or peptides include the binding domain or activation domain of a transcriptional activator as used in the yeast two-hybrid system, phage coat proteins, (histidine)$_6$-tag, glutathione S-transferase, protein A, maltose-binding protein, dihydrofolate reductase, Tag•100 epitope (EETARFQPGYRS), c-myc epitope (EQKLISEEDL), FLAG®-epitope (DYKDDDK), lacZ, CMP (calmodulin-binding peptide), HA epitope (YPYDVPDYA), protein C epitope (EDQVDPRLIDGK) and VSV epitope (YTDIEMNRLGK).

Deletional variants of a protein of the invention are characterised by the removal of one or more amino acids from the amino acid sequence of said protein.

Amino acid variants of a protein of the invention may readily be made using peptide synthetic techniques well known in the art, such as solid phase peptide synthesis and the like, or by recombinant DNA manipulations. The manipulation of DNA sequences to produce variant proteins, which manifest as substitutional, insertional or deletional variants are well known in the art. For example, techniques for making substitution mutations at predetermined sites in DNA having known sequence are well known to those skilled in the art, such as by M13 mutagenesis, T7-Gen in vitro mutagenesis kit (USB, Cleveland, Ohio), QuickChange Site Directed mutagenesis kit (Stratagene, San Diego, Calif.), PCR-mediated site-directed mutagenesis or other site-directed mutagenesis protocols. Another alternative to manipulate DNA sequences to produce variant proteins, which manifest as substitutional, insertional or deletional variants comprises targeted in vivo gene modification which can be achieved by chimeric RNA/DNA oligonucleotides as described by e.g. (Palmgren 1997; Yoon et al. 1996).

"Derivatives" of a protein of the invention are those peptides, oligopeptides, polypeptides, proteins and enzymes which comprise at least about five contiguous amino acid residues of said polypeptide but which retain the biological activity of said protein. A "derivative" may further comprise additional naturally-occurring, altered glycosylated, acylated or non-naturally occurring amino acid residues compared to the amino acid sequence of a naturally-occurring form of said polypeptide. Alternatively or in addition, a derivative may comprise one or more non-amino acid substituents compared to the amino acid sequence of a naturally-occurring form of said polypeptide, for example a reporter molecule or other ligand, covalently or non-covalently bound to the amino acid sequence such as, for example, a reporter molecule which is bound thereto to facilitate its detection.

With "immunologically active" is meant that a molecule or specific fragments thereof such as epitopes or haptens are recognised by, i.e. bind to antibodies.

In the context of the current invention are also included homologous, derivatives and/or immunologically active fragments of any of the inventive polypeptides. "Antibodies" include monoclonal, polyclonal, synthetic or heavy chain camel antibodies as well as fragments of antibodies such as Fab, Fv or scFv fragments. Monoclonal antibodies can be prepared by the techniques as described previously e.g. (Liddle & Cryer 1991) which comprise the fusion of mouse myeloma cells to spleen cells derived from immunised animals. The term "antibodies" furthermore includes derivatives thereof such as labelled antibodies. Antibody labels include alkaline phosphatase, PKH2, PKH26, PKH67, fluorescein (FITC), Hoechst 33258, R-phycoerythrin (PE), rhodamine (TRITC), Quantum Red, Texas Red, Cy3, biotin, agarose, peroxidase, gold spheres and radiolabels (e.g. $^{125}$I, $^{131}$I, $^{35}$S, $^{14}$C, $^{32}$P, $^{33}$P, $^{3}$H). Tools in molecular biology relying on antibodies against a protein include protein gel blot analysis, screening of expression libraries allowing gene identification, protein quantitative methods including ELISA and RIA, immunoaffinity purification of proteins, immunoprecipitation of proteins e.g. (Magyar et al 1997) and immunolocalization. Other uses of antibodies and especially of peptide antibodies include the study of proteolytic processing (Loffler et al 1994; Woulfe et al. 1994), determination of protein active sites (Lerner 1982), the study of precursor and post-translational processing (Baron & Baltimore 1982;Lerner et al 1981;Semler et al. 1982), identification of protein domains involved in protein-protein interactions (Murakami et al. 1992) and the study of exon usage in gene expression (Tamura et al. 1991).

In the scope of the current invention are also antibodies recognising the proteins of the present invention or homologue, derivative or fragment thereof as defined supra.

The terms "gene(s)", "polynucleotide(s)", "nucleic acid, sequence(s)", "nucleotide sequence(s)", "DNA sequence(s)" or "nucleic acid molecule(s)", when used herein refer to nucleotides, either ribonucleotides or deoxytibonucleobdes or a combination of both, in a polymeric form of any length. Said terms furthermore include double-stranded and single-stranded DNA and RNA. Said terms also include known nucleotide modifications such as methylation, cyclization and 'caps' and substitution of one or more of the naturally occurring nucleotides with an analogue such as inosine. Said terms also encompass peptide nucleic acids (PNAs), a DNA analogue in which the backbone is a pseudopeptid e consisting of N-(2-aminoethyl)-glycine units rather than a sugar. PNAs mimic the behaviour of DNA and bind complementary nucleic acid strands. The neutral backbone of PNA results in stronger binding and greater specificity than normally achieved. In addition, the unique chemical, physical and biological properties of PNA have been exploited to produce powerful biomolecular tools, anti-sense and anti-gene agents, molecular probes and biosensors.

With "recombinant DNA molecule" or "chimeric gene" is meant a hybrid DNA produced by joining pieces of DNA from different sources. With "heterologous nucleotide sequence" is intended a sequence that is not naturally occurring with the promoter sequence. While this nucleotide sequence is heterologous to the promoter sequence, it may be homologous, or native, or heterologous, or foreign, to the plant host. "Sense strand" refers to the strand of a double-stranded DNA molecule that is homologous to a mRNA transcript thereof. The "anti-sense strand" contains an inverted sequence, which is complementary to that of the "sense strand".

A "coding sequence" or "open reading frame" or "ORF" is defined as a nucleotide sequence that can be transcribed into mRNA and/or translated into a polypeptide when placed under the control of appropriate regulatory sequences, i.e. when said coding sequence or ORF is present in an expressible format. Said coding sequence of ORF is bounded by a 5' translation start codon and a 3' translation stop codon. A coding sequence or ORF can include, but is not limited to RNA, mRNA, cDNA, recombinant nucleotide sequences, synthetically manufactured nucleotide sequences or genomic DNA. Said coding sequence or ORF can be interrupted by intervening nucleic acid sequences. Genes and coding sequences essentially encoding the same protein but isolated from different sources can consist of substantially divergent nucleic acid sequences. Reciprocally, substantially divergent nucleic acid sequences can be designed to effect expression of essentially the same protein. Said nucleic acid sequences are the result of e.g. the existence of different alleles of a given gene, or of the degeneracy of the genetic code or of differences in codon usage. Thus amino acids such as methionine and tryptophan are encoded by a single codon whereas other amino acids such as arginine, leucine and serine can each be translated from up to six different codons. Differences in preferred codon usage are illustrated below for *Agrobacterium tumefaciens* (a bacterium), *A. thaliana*, *M. sativa* (two dicotyledonous plants) and *Oryza sativa* (a monocotyledonous plant). These examples were extracted from (www.kazusa.orjp/codon). To give one example, the codon GGC (for glycine) is the most frequently used codon in *A. tumefaciens* (36.2%), is the second most frequently used codon in *O. sativa* but is used at much lower frequencies in *A. thaliana* and *M. sativa* (9% and 8.4%, respectively). Of the four possible codons encoding glycine (see Table 2), said GGC codon is most preferably used in *A. tumefaciens* and *O. sativa*. However, in *A. thaliana* this is the GGA (and GGU) codon whereas in *M. sativa* this is the GGU (and GGA) codon. Allelic variants are further defined as to comprise single nucleotide polymorphisms (SNPs) as well as small insertion-ideletion polymorphisms (INDELs; the size of INDELs is usually less than 100. bp). SNPs and INDELs form the largest set of sequence variants in naturally occurring polymorphic strains of most organisms. They are helpful in mapping genes and discovery of genes and gene functions. They are furthermore helpful in identification of genetic loci, e.g. plant genes, involved in determining processes such as growth rate, plant size and plant yield, plant vigor, disease resistance, stress tolerance etc. Many techniques are nowadays available to identify SNPs and/or INDELs including (i) PCR followed by denaturing high performance liquid chromatography (DHPLC; e.g. . (Cho et al. 1999)); (ii) constant denaturant capillary electrophoresis (CDCE) combined with high-fidelity PCR (e.g. (U-Sucholeiki et al. 1999)); (iii) denaturing gradient gel electrophoresis (e.g. Fischer and Lerman 1983); (iv) matrix-assisted laser desorption/ionization time-of-flight mass spectrometry (MALDI-TOF MS; e.g. (Ross et al. 2000)); (v) real-time fluorescence monitoring PCR assays (e.g. Tapp et al. 2000); (vi) Acrydite.TM. gel technology (e.g. Kenney et al. 1998); (vii) cycle dideoxy fingerprinting (CddF; e.g. (Langemeier et al. 1994); (viii) single-strand conformation polymorphism (SSCP) analysis (e.g. (Vidal-Puig & Moller 1994)) and (ix) mini-sequencing primer extension reaction (e.g. Syvanen 1999). The technique of 'Targeting Induced Local Lesions in Genomes' (TILLING: (McCallum et al. 2000a;McCallum et al. 2000b)), which Is a variant of(i)

supra, can also be applied to rapidly identify an altered gene in e.g. chemically mutagenized plant individuals showing interesting phenotypes.

"Hybridisation" is the process wherein substantially homologous complementary nucleotide sequences anneal to each other. The hybridisation process can occur entirely in solution, i.e. both complementary nucleic acids are in solution. Tools in molecular biology relying on such a process include the polymerase chain reaction (PCR; and all methods based thereon), subtractive hybridisation, random primer extension, nuclease S1 mapping, primer extension, reverse transcription, cDNA synthesis, differential display of RNAs, and DNA sequence determination. The hybridisation process can also occur with one of the complementary nucleic acids immobilised to a matrix such as magnetic beads, Sepharose beads or any other resin. Tools in molecular biology relying on such a process include the isolation of poly (A+) mRNA. The hybridisation process can furthermore occur with one of the complementary nucleic acids immobilised to a solid support such as a nitro-cellulose or nylon membrane or immobilised by e.g. photolithography to e.g. a siliceous glass support (the latter known as nucleic acid arrays or microarrays or as nucleic acid chips). Tools in molecular biology relying on such a process include RNA and DNA gel blot analysis, colony hybridisation, plaque hybridisation, in situ hybridisation and microarray hybridisation. In order to allow hybridisation to occur, the nucleic acid molecules are generally thermally or chemically denatured to melt a double strand into two single strands and/or to remove hairpins or other secondary structures from single stranded nucleic acids. The stringency of hybridisation is influenced by conditions such as temperature, salt concentration and hybridisation buffer composition. High stringency conditions for hybridisation include high temperature and/or low salt concentration (salts include NaCl and $Na_3$-citrate) and/or the inclusion of formamide in the hybridisation buffer and/or lowering the concentration of compounds such as SDS (detergent) in the hybridisation buffer and/or exclusion of compounds such as dextran sulphate or polyethylene glycol (promoting molecular crowding) from the hybridisation buffer. Conventional hybridisation conditions are described e.g. (Sambrook et al. 1989) but the skilled craftsman will appreciate that numerous different hybridisation conditions can be designed in function of the known or the expected homology and/or length of the nucleic acid sequence. With specifically hybridising is meant hybridising under stringent conditions. Sufficiently low stringency hybridisation conditions are particularly preferred to isolate nucleic acids heterologous to the DNA sequences of the invention defined supra. Elements contributing to said heterology include allelism, degeneration of the genetic code and differences in preferred codon usage as discussed supra.

Accordingly, the scope of the current invention is also related to the use of the inventive DNA sequences encoding the polypeptides of the present invention, homologue, derivative and/or immunologically fragment thereof as defined higher in any method of hybridisation. The current invention furthermore also relates to DNA sequences hybridising to said inventive DNA sequences.

"Specifically amplifying" herein using an amplification method which is selective and only amplifies a nucleic acid sequence with a specific base-pair composition (e.g. polymerase chain reaction).

DNA sequences as defined in the current invention can be interrupted by intervening sequences. With "intervening sequences" is meant any nucleic acid sequence which disrupts a coding sequence comprising said inventive DNA sequence or which disrupts the expressible format of a DNA sequence comprising said inventive DNA sequence. Removal of the intervening sequence restores said coding sequence or said expressible format. Examples of intervening sequences include introns, mobilizable DNA sequences such as transposons and DNA tags such as e.g. a T-DNA. With "mobilizable DNA sequence" is meant any DNA sequence that can be mobilised as the result of a recombination event.

To effect expression of a protein in a cell, tissue or organ, preferably of plant origin, either the protein may be introduced directly to said cell, such as by microinjection or ballistic means or alternatively, an isolated nucleic acid molecule encoding said protein may be introduced into said cell, tissue or organ in an expressible format.

Preferably, the DNA sequence of the invention comprises a coding sequence or open reading frame (ORF) encoding a protein of the present invention or a homologue or derivative thereof or an immunologically active thereof as defined supra. The preferred proteins of the invention comprises the amino acid sequence as presented in SEQ ID NO. 3, 4, 6, 8, 10, 12, 14, 16, 18, 20 and 21.

With "vector" or "vector sequence" is meant a DNA sequence, which can be introduced in an organism by transformation and can be stably maintained in said organism. Vector maintenance is possible in e.g. cultures of *Escherichia coli, A. tumefaciens, Saccharomyces cerevisiae* or *Schizosaccharomyces pombe*. Other vectors such as phagemids and cosmid vectors can be maintained and multiplied in bacteria and/or viruses. Vector sequences generally comprise a set of unique sites recognised by restriction enzymes, the multiple cloning site (MCS), wherein one or more non-vector sequence(s) can be inserted.

With "non-vector sequence" is accordingly meant a DNA sequence which is integrated in one or more of the sites of the MCS comprised within a vector.

"Expression vectors" form a subset of vectors which, by virtue of comprising the appropriate regulatory sequences enabling the creation of an expressible format for the inserted non-vector sequence(s), thus allowing expression of the protein encoded by said non-vector sequence(s). Expression vectors are known in the art enabling protein expression in organisms including bacteria (e.g. *E. coli*), fungi (e.g. *S. cerevisiae, S. pombe, Pichia pastoris*), insect cells (e.g. baculoviral expression vectors), animal cells (e.g. COS or CHO cells) and plant cells (e.g. potato virus X-based expression vectors, see e.g. Vance et al. 1998—WO9844097). See also further in this specification for typical plant expression vectors.

The current invention clearly includes any vector or expression vector comprising a non-vector DNA sequence comprising the nucleotide sequences according to the present invention or a non-vector sequence encoding the proteins of the present invention, or the homologue, derivative and/or immunologically active fragment thereof as defined supra.

As an alternative to expression vector-mediated protein production in biological systems, chemical protein synthesis can be applied. Synthetic peptides can be manufactured in solution phase or in solid phase. Solid phase peptide synthesis (Merrifield 1963) is, however, the most common way and involves the sequential addition of amino acids to create a linear peptide chain.

By "expressible format" or "under the control of expression control sequences" is meant that the isolated nucleic acid molecule is in a form suitable for being transcribed into mRNA and/or translated to produce a protein, either constitutively or following induction by an intracellular or extracellular signal, such as an environmental stimulus or stress (mitogens, anoxia, hypoxia, temperature, salt, light, dehydration, etc) or a chemical compound such as IPTG (isopropyl- β-D-thiogalactopyranoside) or such as an antibiotic (tetracycline, ampicillin, rifampicin, kanamycin), hormone (e.g. gibberellin, auxin, cytokinin, glucocorticoid, brassinosteroid, ethylene, abscisic acid etc), hormone analogue (iodoacetic acid (IAA), 2,4-D, etc), metal (zinc, copper, iron, etc), or dexamethasone, amongst others. As will be known to those skilled in the art, expression of a functional protein may also require one or more post-translational modifications, such as glycosylation, phosphorylation, dephosphorylation, or one or more protein-protein interactions, amongst others. All such processes are included within the scope of the term "expressible format".

Preferably, expression of a protein in a specific cell, tissue, or organ, preferably of plant origin, is effected by introducing and expressing an isolated nucleic acid molecule encoding said protein, such as a cDNA molecule, genomic gene, synthetic oligonucleotide molecule, mRNA molecule or open reading frame, to said cell, tissue or organ, wherein said nucleic acid molecule is placed operably in connection with suitable regulatory sequences including a promoter, preferably a plant-expressible promoter, and a terminator sequence.

"Regulatory sequence" refers to control DNA sequences, which are necessary to affect the expression of coding sequences to which they are ligated. The nature of such control sequences differs depending upon the host organism. In prokaryotes, control sequences generally include promoters, ribosomal binding sites, and terminators. In eukaryotes generally control sequences include promoters, terminators and enhancers or silencers.

Within the scope of the invention are also the nucleotide sequences as defined in the present invention fused to any regulatory sequence. The term "control sequences" is intended to include, at a minimum, all components the presence of which are necessary for expression, and may also include additional advantageous components and which determines when, how much and where a specific gene is expressed.

Reference herein to a "promoter" is to be taken in its broadest context and includes the transcriptional regulatory sequences derived from a classical eukaryotic genomic gene, including the TATA box which is required for accurate transcription initiation, with or without a CCMT box sequence and additional regulatory elements (i.e. upstream activating sequences, enhancers and silencers) which alter gene expression in response to developmental and/or external stimuli, or in a tissue-specific manner.

The term "promoter" also includes the transcriptional regulatory sequences of a classical prokaryotic gene, in which case it may include a −35 box sequence and/or a −10 box transcriptional regulatory sequences.

The term "promoter" is also used to describe a synthetic or fusion molecule or derivative, which confers, activates or enhances expression of a nucleic acid molecule in a cell, tissue or organ.

Promoters may contain additional copies of one or more specific regulatory elements, to further enhance expression and/or to alter the spatial expression and/or temporal expression of a nucleic acid molecule to which it is operably connected. Such regulatory elements may be placed adjacent to a heterologous promoter sequence to drive expression of a nucleic acid molecule in response to e.g. copper, glucocorticoids, dexamethasone, tetracycline, gibberellin, cAMP, abscisic acid, auxin, wounding, ethylene, jasmonate or salicylic acid or to confer expression of a nucleic acid molecule to specific cells, tissues or organs such as meristems, leaves, roots, embryo, flowers, seeds or fruits. In the context of the present invention, the promoter preferably is a plant-expressible promoter sequence. Promoters, however, that also function or solely function in non-plant cells such as bacteria, yeast cells, insect cells and animal cells are not excluded from the invention. By "plant-expressible" is meant that the promoter sequence, including any additional regulatory elements added thereto or contained therein, is at least capable of inducing, conferring, activating or enhancing expression in a plant cell, tissue or organ, preferably a monocotyledonous or dicotyledonous plant cell, tissue, or organ.

The terms "plant-operable" and "operable in a plant" when used herein, in respect of a promoter sequence, shall be taken to be equivalent to a plant-expressible promoter sequence.

In the present context, a "regulated promoter" or "regulatable promoter sequence" is a promoter that is capable of conferring expression on a structural gene in a particular cell, tissue, or organ or group of cells, tissues or organs of a plant, optionally under specific conditions, however does generally not confer expression throughout the plant under all conditions. Accordingly, a regulatable promoter sequence may be a promoter sequence that confers expression on a gene to which it is operably connected in a particular location within the plant or alternatively, throughout the plant under a specific set of conditions, such as following induction of gene expression by a chemical compound or other elicitor. Preferably, the regulatable promoter used in the performance of the present invention confers expression in a specific location within the plant, either constitutively or following induction, however not in the whole plant under any circumstances. Included within the scope of such promoters are cell-specific promoter sequences, tissue-specific promoter sequences, organ-specific promoter sequences, cell cycle specific gene promoter sequences, inducible promoter sequences and constitutive promoter sequences that have been modified to confer expression in a particular part of the plant at any one time, such as by integration of said constitutive promoter within a transposable genetic element (Ac, Ds, Spm, En, or other transposon). Those skilled in the art will be aware that an "inducible promoter" is a promoter the transcriptional activity of which is increased or induced in response to a developmental, chemical, environmental, or physical stimulus. Within the scope of the present invention are the nucleotide sequences as defined in the claims, fused to a stress inducible promoter. Similarly, the skilled craftsman will understand that a "constitutive promoter" is a promoter that is transcriptionally active throughout most, but not necessarily all parts of an organism, preferably a plant, during most, but not necessarily all phases of its growth and development. Contrarily the term "ubiquitous promoter" is taken to indicate a promoter that is transcriptionally active throughout most, but not necessarily all parts of an organism, preferably a plant.

Those skilled in the art will readily be capable of selecting appropriate promoter sequences for use in regulating appropriate expression of the proteins of the present inventio as described supra from publicly-available or readily-available sources, without undue experimentation.

Placing a nucleic acid molecule under the regulatory control of a promoter sequence, or in operable connection with a promoter sequence means positioning said nucleic acid molecule such that expression is controlled by the promoter sequence. A promoter is usually, but not necessarily, positioned upstream, or at the 5'-end, and within 2 kb of the start site of transcription, of the nucleic acid molecule which it regulates. In the construction of heterologous promoter/structural gene combinations it is generally preferred to position the promoter at a distance from the gene transcription start site that is approximately the same as the distance between that promoter and the gene it controls in its natural setting (i.e., the gene from which the promoter is derived).

"Expression" means the production of a protein or nucleotide sequence in the cell itself or in a cell-free system. It includes transcription into an RNA product, post-transcriptional modification and/or translation to a protein product or polypeptide from a DNA encoding that product, as well as possible post-translational modifications.

"Operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences. In case the control sequence is a promoter, it is obvious for a skilled person that double-stranded nucleic acid is preferably used.

The term "terminator" refers to a DNA sequence at the end of a transcriptional unit which signal termination of transcription. Terminators are 3'-non-translated DNA sequences containing a polyadenylation signal, which facilitates the addition of polyadenylate sequences to the 3'-end of a primary transcript. Terminators active in cells derived from viruses, yeasts, moulds, bacteria, insects, birds, mammals and plants are known and described in the literature. They may be isolated from bacteria, fungi, viruses, animals and/or plants.

Examples of terminators particularly suitable for use in the gene constructs of the present invention include the *Agrobacterium tumefaciens* nopaline synthase (NOS) gene terminator, the *Agrobacterium tumefaciens* octopine synthase (OCS) gene terminator sequence, the Cauliflower mosaic virus (CaMV) 35S gene terminator sequence, the *Oryza sativa* ADP-glucose pyrophosphorylase terminator sequence (t3'Bt2), the *Zea mays* zein gene terminator sequence, the rbcs-1A gene terminator, and the rbcs-3A gene terminator sequences, amongst others.

Those skilled in the art will be aware of suitable promoter sequences and terminator sequences which may be suitable for use in performing the invention. Such sequences may readily be used without any undue experimentation.

Altering the expression of e gene can be the downregulation of expression. In the context of the current invention is envisaged the downregulation of the expression of some proteins which are involved in the process of processing of messenger RNA precursors.

This can for example result in a beneficial effect on messenger RNA processing and stress tolerance, when said protein was a negative regulator of the process. "Downregulation of expression" as used herein means lowering levels of gene expression and/or levels of active gene product and/or levels of gene product activity. Decreases in expression may be accomplished by e.g. the addition of coding sequences or parts thereof in a sense orientation (if resulting in co-suppression) or in an antisense orientation relative to a promoter sequence and furthermore by e.g. insertion mutagenesis (e.g. T-DNA insertion or transposon insertion) or by gene silencing strategies as described by e.g. Angell and Baulcombe 1998 (WO9836083), Lowe et al. 1989 (WO9853083), Lederer et al. 1999 (WO9915682) or Wang et al. 1999 (WO9953050). Genetic constructs aimed at silencing gene expression may have the nucleotide sequence of said gene (or one or more parts thereof) contained therein in a sense and/or antisense orientation relative to the promoter sequence. Another method to downregulate gene expression comprises the use of ribozymes, e.g. as described in Atkins et al. 1994 (WO9400012), Lenee et al. 1995 (WO9503404), Lutziger et al. 2000 (WO00009619), Prinsen et al. 1997 (WO9713865) and Scott et al. 1997 (WO9738116).

Modulating, including lowering, the level of active gene products or of gene product activity can be achieved by administering or exposing cells, tissues, organs or organisms to said gene product, a homologue, analogue, derivative and/or immunologically active fragment thereof. Immunomodulation is another example of a technique capable of downregulation levels of active gene product and/or of gene product activity and comprises administration of or exposing to or expressing antibodies to said gene product to or in cells, tissues, organs or organisms wherein levels of said gene product and/or gene product activity are to be modulated. Such antibodies comprise "plantibodies", single chain antibodies, IgG antibodies and heavy chain camel antibodies as well as fragments thereof. Within the scope of the present invention are antibodies, recognizing the proteins of the present invention and that can be used for said immunomodulation.

Modulating, including lowering, the level of active gene products or of gene product activity can furthermore be achieved by administering or exposing cells, tissues, organs or organisms to an inhibitor or activator of said gene product or the activity thereof. Such inhibitors or activators include proteins (comprising e.g. proteinases and kinases) and chemical compounds identified according to the current By "cell fate and/or plant development and/or plant morphology and/or biochemistry and/or physiology" is meant that one or more developmental and/or morphological and/or biochemical and/or physiological characteristics of a plant is altered by the performance of one or more steps pertaining to the invention described herein.

"Cell fate" refers to the cell-type or cellular characteristics of a particular cell that are produced during plant development or a cellular process therefor, in particular during the cell cycle or as a consequence of a cell cycle process.

"Plant development" or the term "plant developmental characteristic" or similar term shall, when used herein, be taken to mean any cellular process of a plant that is involved in determining the developmental fate of a plant cell, in particular the specific tissue or organ type into which a progenitor cell will develop. Cellular processes relevant to plant development will be known to those skilled in the art. Such processes include, for example, morphogenesis, photomorphogenesis, shoot development, root development, vegetative development, reproductive development, stem elongation, flowering, and regulatory mechanisms involved in determining cell fate, in particular a process or regulatory process involving the cell cycle.

"Plant morphology" or the term "plant morphological characteristic" or similar term will, when used herein, be understood by those skilled in the art to refer to the external appearance of a plant, including any one or more structural features or combination of structural features thereof. Such structural features include the shape, size, number, position, colour, texture, arrangement, and patternation of any cell, tissue or organ or groups of cells, tissues or organs of a plant, including the root, stem, leaf, shoot, petiole, trichome, flower, petal, stigma, style, stamen, pollen, ovule, seed, embryo, endosperm, seed coat, aleurone, fibre, fruit, cambium, wood, heartwood, parenchyma, aerenchyma, sieve element, phloem or vascular tissue, amongst others.

"Plant biochemistry" or the term "plant biochemical characteristic" or similar term will, when used herein, be understood by those skilled in the art to refer to the metabolic and catalytic processes of a plant, including primary and secondary metabolism and the products thereof, including any small molecules, macromolecules or chemical compounds, such as but not limited to starches, sugars, proteins, peptides, enzymes, hormones, growth factors, nucleic acid molecules, celluloses, hemicelluloses, calloses, lectins, fibres, pigments such as anthocyanins, vitamins, minerals, micronutrients, or macronutrients, that are produced by plants.

"Plant physiology" or the term "plant physiological characteristic" or similar term will, when used herein, be understood to refer to the functional processes of a plant, including developmental processes such as growth, expansion and differentiation, sexual development, sexual reproduction, seed set, seed development, grain filling, asexual reproduction, cell division, dormancy, germination, light adaptation, photosynthesis, leaf expansion, fiber production, secondary growth or wood production, amongst others; responses of a plant to externally-applied factors such as metals, chemicals, hormones, growth factors, environment and environmental stress factors (eg. anoxia, hypoxia, high temperature, low temperature, dehydration, light, day length, flooding, salt, heavy metals, amongst others), including adaptive responses of plants to said externally-applied factors.

The term "environmental stress" has been defined in different ways in the prior art and largely overlaps with the term "osmotic stress". (Holmberg & Bülow, 1998, Trends plant sci. 3, 61-66) for instance define different environmental stress factors which result in abiotic stress. The term osmotic stress as used herein is meant as a stress situation induces by conditions as salinity, drought, heat, chilling (or cold) and freezing. With The term "environmental stress" as used in the present invention refers to any adverse effect on metabolism, growth or viability of the cell, tissue, seed, organ or whole plant which is produced by an non-living or non-biological environmental stress. More particularly, it also encompasses environmental factors such as water stress (flooding, water logging, drought, dehydration), anaerobic (low level of oxygen, $CO_2$ etc.), aerobic stress, osmotic stress, salt stress, temperature stress (hot/heat, cold, freezing, frost) or nutrients deprivation, pollutants stress (heavy metals, toxic chemicals), ozone, high light, pathogen (including viruses, bacteria, fungi, insects and nematodes) and combinations of these.

The term "anaerobic stress" means any reduction in oxygen levels sufficient to produce a stress as herein before defined, including hypoxia and anoxia.

The term "flooding stress" refers to any stress which is associated with or induced by prolonged or transient immersion of a plant, plant part, tissue or isolated cell in a liquid medium such as occurs during monsoon, wet season, flash flooding or excessive irrigation of plants, etc.

"Cold stress" or "chilling stress" and "heat stress" are stresses induced by temperatures that are respectively, below or above, the optimum range of growth temperatures for a particular plant species. Such optimum growth temperature ranges are readily determined or known to those skilled in the art.

"Dehydration stress" is any stress which is associated with or induced by the loss of water, reduced turgor or reduced water content of a cell, tissue, organ or whole plant.

"Drought stress" refers to any stress, which is induced by or associated with the deprivation of water or reduced supply of water to a cell, tissue, organ or organism.

"Oxidative stress" refers to any stress, which increases the intracellular level of reactive oxygen species.

The terms "salinity-induced stress", "salt stress" or "salt ionic toxicity" or mineral salt toxicity or similar terms refer to any stress which is associated with or induced by elevated concentrations of salt and which result in a perturbation in the osmotic potential of the intracellular or extracellular environment of a cell. The best known examples of mineral salts that induce said salt stress are Na+ and Li+.

The transgenic plants obtained in accordance with the method of the present invention, upon the presence of the polynucleic acid and/or regulatory sequence introduced into said plant, attain resistance, tolerance or improved tolerance or resistance against environmental stress which the corresponding wild-type plant was susceptible to.

The terms "tolerance" and "resistance" cover the range of protection from a delay to complete inhibition of alteration in cellular metabolism, reduced cell growth and/or cell death caused by the environmental stress conditions defined herein before. Preferably, the transgenic plant obtained in accordance with the method of the present invention is tolerant or resistant to environmental stress conditions in the sense that said plant is capable of growing substantially normal under environmental conditions where the corresponding wild-type plant shows reduced growth, metabolism, viability, productivity and/or male or female sterility. As used herein, "stress tolerance" refers to the capacity to grow and produce biomass during stress, the capacity to reinitiate growth and biomass production after stress, and the capacity to survive stress. The term "stress tolerance" also covers the capacity of the plant to undergo its developmental program during stress similarly to under non-stressed conditions, e.g. to switch from dormancy to germination and from vegetative to reproductive phase under stressed conditions similarly as under non-stressed conditions. Methodologies to determine plant growth or response to stress include, but are not limited to height measurements, leaf area, plant water relations, ability to flower, ability to generate progeny and yield or any other methodology known to those skilled in the art.

"Growth" refers to the capacity of the plant or of plant parts to grow and increase in biomass while "yield" refers to the harvestable biomass of plants or plant parts, particularly those parts of commercial value. "Growth and/or yield under stressed and non-stressed conditions" refers to the fact that field-grown plants almost always will experience some form of stress, albeit mild. It is therefore preferred not to distinguish non-stressed from mild-stressed conditions. As certain beneficial effects of the invention on growth and yield are expected to occur under both severe and mild stress conditions, they are thus described as increasing growth and/or yield under stressed and non-stressed conditions. Means for introducing recombinant DNA into plant tissue or cells include, but are not limited to, transformation using $CaCl_2$ and variations thereof, in particular the method described previously (Hanahan 1983), direct DNA uptake into protoplasts (Krens et al. 1982; Paszkowski et al. 1984), PEG-mediated uptake to protoplasts (Armstrong et al. 1990) microparticle bombardment, electroporation (Fromm et al. 1985), microinjection of DNA (Crossway et al. 1986; Fromm et al. 1985), microparticle bombardment of tissue explants or cells (Christou et al. 1988), vacuum-infiltration of tissue with nucleic acid, or in the case of plants, T-DNA-mediated transfer from *Agrobacterum* to the plant tissue as described essentially (An et al 1985;Dodds 1985;Herrera-Estrella et al. 1983a;Herrera-Estrella et al. 1983b). Methods for transformation of monocotyledonous plants are well known in the art and include *Agrobacterium*-mediated transformation (Cheng et al. 1997—WO9748814; Hansen 1998—WO9854961, Hiei et al. 1994—WO9400977;Hiei et al. 1998—WO9817813;Rikiishi et al. 1999—WO9904618; Saito et al. 1995—WO9506722), microprojectile bombardment (Adams et al. 1999—U.S. Pat. No. 5,969,213; Bowen et al. 1998—U.S. Pat. No. 5,736,369; Chang et al. 1994—WO9413822; Lundquist et al. 1999—U.S. Pat. Nos. 5,874, 265/5,990,390; Vasil and Vasil 1995—U.S. Pat. No. 5,405, 765; Walker et al. 1999—U.S. Pat. No. 5,955,362), DNA uptake (Eyal et al. 1993—WO9318168), microinjection of *Agrobacterium* cells (von Holt 1994—DE4309203) and sonication (Finer et al. 1997—U.S. Pat. No. 5693512).

A whole plant may be regenerated from the transformed or transfected cell, in accordance with procedures well known in the art. Plant tissue capable of subsequent clonal propagation, whether by organogenesis or embryogenesis, may be transformed with a gene construct of the present invention and a whole plant regenerated therefrom. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem).

Preferably, the plant is produced according to the inventive method is transfected or transformed with a genetic sequence, or amenable to the introduction of a protein, by any art-recognized means, such as microprojectile bombardment, microinjection, *Agrobacterium*-mediated transformation (including the 'flower dip' transformation method; (Bechtold & Pelletier 1998;Trieu et al. 2000)), protoplast fusion, or electroporation, amongst others. Most preferably said plant is produced by *Agrobacteriuim*-mediated transformation.

With "binary transformation vector" is meant a T-DNA transformation vector comprising: a T-DNA region comprising at least one gene of interest and/or at least one selectable marker active in the eukaryotic cell to be transformed; and a vector backbone region comprising at least origins of replication active in *E. coli* and *Agrobacterium* and markers for selection in *E. coli* and *Agrobacterium*. Alternatively, replication of the binary transformation vector in *Agrobacterium* is dependent on the presence of a separate helper plasmid. The binary vector pGreen and the helper plasmid pSoup form an example of such a system as described in e.g. (Hellens et al. 2000) or as available on the internet site www.pgreen.ac.uk.

The T-DNA borders of a binary transformation vector can be derived from octopine-type or nopaline-type Ti plasmids or from both. The T-DNA of a binary vector is only transferred to a eukaryotic cell in conjunction with a helper plasmid. Also known in the art are multiple binary vector *Agrobacterium* strains for efficient co-transformation of plants (Bidney and Scelonge 2000—WO001 8939).

"Host" or "host cell" or host organism" herein is any prokaryotic or eukaryotic cell or organism that can be a recipient of the sequences of the present invention. A "host," as the term is used herein, includes prokaryotic or eukaryotic organisms that can be genetically engineered. For examples of such hosts, see Maniatis et al., Molecular Cloning. A Laboratory Manual, Cold Spring Harbor Laboratory, Cold Spring Harbor, N.Y. (1982). "plant cell" comprises any cell derived from any plant and existing in culture as a single cell, a group of cells or a callus. A plant cell may also be any cell in a developing or mature plant in culture or growing in nature.

"Plant" or "Plants" comprise all plant species which belong to the superfamily Viridiplantae. The present invention is applicable to any plant, in particular a monocotyledonous plants and dicotyledonous plants including a fodder or forage legume, ornamental plant, food crop, tree, or shrub selected from the list comprising *Acacia* spp., *Acer* spp., *Actinidia* spp., *Aesculus* spp., *Agathis australis, Albizia amara, Alsophila tricolor, Andropogon* spp., *Arachis* spp, *Areca catechu, Astelia fragrans, Astragalus cicer, Baikiaea plurijuga, Betula* spp., *Brassica* spp., *Bruguiera gymnorrhiza, Burkea africana, Butea frondosa, Cadaba farinosa, Calliandra* spp, *Camellia sinensis, Canna indica, Capsicum* spp., *Cassia* spp., *Centroema pubescens, Chaenomeles* spp., *Cinnamomum cassia, Coffea arabica, Colophospermum mopane, Coronillia varia, Cotoneaster serotina, Crataegus* spp., *Cucumis* spp., *Cupressus* spp., *Cyathea dealbata, Cydonia oblonga, Cryptomeria japonica, Cymbopogon* spp., *Cynthea dealbata, Cydonia oblonga, Dalbergia monetaria, Davallia divaricata, Desmodium* spp., *Dicksonia squarosa, Diheteropogon amplectens, Dioclea* spp, *Dolichos* spp., *Dorycnium rectum, Echinochloa pyramidalis, Ehrartia* spp., *Eleusine coracana, Eragrestis* spp., *Erythrina* spp., *Eucalyptus* spp., *Euclea schimperi, Eulalia villosa, Fagopyrum* spp., *Feijoa sellowiana, Fragaria* spp., *Flemingia* spp, *Freycinetia banksii, Geranium thunbergii, Ginkgo biloba, Glycine javanica, Gliricidia* spp, *Gossypium hirsutum, Grevillea* spp., *Guibourtia coleosperma, Hedysarum* spp., *Hemarthia altissima, Heteropogon contortus, Hordeum vulgare, Hyparrhenia rufa, Hypericum erectum, Hyperthelia dissoluta, Indigo incarnata, Iris* spp., *Leptarrhena pyrolifolia, Lespediza* spp., *Lettuca* spp., *Leucaena leucocephala, Loudetia simplex, Lotonus bainesii, Lotus* spp., *Macrotyloma axillare, Malus* spp., *Manihot esculenta, Medicago sativa, Metasequoia glyptostroboides, Musa sapientum, Nicotianum* spp., *Onobrychis* spp., *Ornithopus* spp., *Oryza* spp., *Peltophorum africanum, Pennisetum* spp., *Persea gratissima, Petunia* spp., *Phaseolus* spp., *Phoenix canariensis, Phormium cookianum, Photinia* spp., *Picea glauca, Pinus* spp., *Pisum sativum, Podocarpus totara, Pogonarthria fleckii, Pogonarthria squarrosa, Populus* spp., *Prosopis cineraria, Pseudotsuga menziesii, Pterolbium stellatum, Pyrus communis, Quercus* spp., *Rhaphiolepsis umbellata, Rhopalostylis sapida, Rhus natalensis, Ribes grossularia, Ribes* spp., *Robinia pseudoacacia, Rosa* spp., *Rubus* spp., *Salix* spp., *Schyzachyrium sanguineum, Sciadopitys verticillata, Sequoia sempervirens, Sequoiadendron giganteum, Sorghum bicolor, Spinacia* spp., *Sporobolus fimbriatus, Stiburus alopecuroides, Stylosanthos humilis, Tadehagi* spp, *Taxodium distichum, Themeda triandra, Trifollum* spp., *Triticum* spp., *Tsuga heterophylla, Vaccinium* spp., *Vicia* spp. *Vitis vinifera, Watsonia pyramidata, Zantedeschia aethiopica, Zea mays*, amaranth, artichoke, asparagus, broccoli, brussel sprout, cabbage, canola, carrot, cauliflower, celery, collard greens, flax, kale, lentil, oilseed rape, okra, onion, potato, rice, soybean, straw, sugarbeet, sugar cane, sunflower, tomato, squash, and tea, amongst others, or the seeds of any plant specifically named above or a tissue, cell or organ culture of any of the above species The present invention is applicable to any plant, in particular a monocotyledonous plants and dicotyledonous plants including a fodder or forage legume, ornamental plant, food crop, tree, or shrub selected from the list comprising *Acacia* spp., *Acer.* spp., *Actinidia* spp., *Aesculus* spp., *Agathis australis, Albizia amara, Alsophila tricolor, Andropogon* spp., *Arachis* spp, *Areca catechu, Astelia fragrans, Astragalus cicer, Baikiaea plurijuga, Betula* spp., *Brassica* spp., *Bruguiera gymnorrhiza, Burkea africana, Butea frondosa, Cadaba farinosa, Calliandra* spp, *Camellia sinensis, Canna indica, Capsicum* spp., *Cassia* spp., *Centroema pubescens, Chaenomeles* spp., *Cinnamomum cassia, Coffea arabica, Colophospermum mopane, Coronillia varia, Cotoneaster serotina, Crataegus* spp., *Cucumis* spp., *Cupressus* spp., *Cyathea dealbata, Cydonia oblonga, Cryptomeria japonica, Cymbopogon* spp., *Cynthea dealbata, Cydonia oblonga, Dalbergia monetaria, Davallia divaricata, Desmodium* spp., *Dicksonia squarosa, Diheteropogon amplectens, Dioclea* spp, *Dolichos* spp., *Dorycnium rectum, Echinochloa pyramidalis, Ehrartia* spp., *Eleusine coracana, Eragrestis* spp., *Erythrina* spp., *Eucalyptus* spp., *Euclea schimperi, Eulalia villosa, Fagopyrum* spp.,

*Feijoa sellowiana, Fragaria* spp., *Flemingia* spp, *Freycinetia banksii, Geranium thunbergii, Ginkgo biloba, Glycine javanica, Gliricidia* spp, *Gossypium hirsutum, Grevillea* spp., *Guibourtia coleosperma, Hedysarum* spp., *Hemarthia altissima, Heteropogon contortus, Hordeum vulgare, Hyparrhenia rufa, Hypericum erectum, Hyperthelia dissoluta, Indigo incamata, Iris* spp., *Leptarrhena pyrolifolia, Lespediza* spp., *Lettuca* spp., *Leucaena leucocephala, Loudetia simplex, Lotonus bainesai, Lotus* spp., *Macrotyloma axillare, Malus* spp., *Manihot esculenta, Medicago sativa, Metasequoia glyptostroboides, Musa sapientum, Nicotianum* spp., *Onobrychis* spp., *Omithopus* spp., *Oryza* spp., *Peltophorum africanum, Pennisetum* spp., *Persea gratissima, Petunia* spp., *Phaseolus* spp., *Phoenix canariensis, Phormium cookianum, Photinia* spp., *Picea glauca, Pinus* spp., *Pisum sativum, Podocarpus totara, Pogonarthria fleckii, Pogonarthria squarrosa, Populus* spp., *Prosopis cineraria, Pseudotsuga menziesii, Pterolobium stellatum, Pyrus communis, Quercus* spp., *Rhaphiolepsis umbellata, Rhopalostylis sapida, Rhus natalensis, Ribes grossularia, Ribes* spp., *Robinia pseudoacacia, Rosa* spp., *Rubus* spp., *Salix* spp., *Schyzachynum sanguineum, Sciadopitys verticillata, Sequoia sempemrens, Sequoiadendron giganteum, Sorghum bicolor, Spinacia* spp., *Sporobolus fimbriatus, Stiburus alopecuroides, Stylosanthos humilis, Tadehagi* spp, *Taxodium distichum, Themeda triandra, Trifolium* spp., *Triticum* spp., *Tsuga heterophylla, Vaccinium* spp., *Vicia* spp. *Vitis vinifera, Watsonia pyramidata, Zantedeschia aethiopica, Zea mays,* amaranth, artichoke, asparagus, broccoli, brussel sprout, cabbage, canola, carrot, cauliflower, celery, collard greens, flax, kale, lentil, oilseed rape, okra, onion, potato, rice, soybean, straw, sugarbeet, sugar cane, sunflower, tomato, squash, and tea, amongst others, or the seeds of any plant specifically named above or a tissue, cell or organ culture of any of the above species "Cereal" comprises crop plants with edible grain for example plants belonging to the grass family that is cultivated for its nutritious grains such as oats, barley, rye, wheat, rice, and corn etc.

Within the scope of the present invention is also the application of the Two-hybrid system, wherein any of the sequences of the present invention are used to study interactions with other factors such as proteins. With "yeast two-hybrid assay" is meant an assay that is based on the observation that many eukaryotic transcription factors comprise two domains, a DNA-binding domain (DB) and an activation domain (AD) which, when physically separated (i.e. disruption of the covalent linkage) do not effectuate target gene expression. Two proteins able to interact physically with one of said proteins fused to DB and the other of said proteins fused to AD will re-unite the DB and AD domains of the transcription factor resulting in target gene expression. The target gene in the yeast two-hybrid assay is usually a reporter gene such as the β-galactosidase gene. Interaction between protein partners in the yeast two-hybrid assay can thus be quantified by measuring the activity of the reporter gene product (Bartel & Fields 1997). Alternatively, a mammalian two-hybrid system can be used which includes e.g. a chimeric green fluorescent protein encoding reporter gene (Shioda et al. 2000). Yet another alternative consists of a bacterial two-hybrid system using e.g. HIS as reporter gene (Joung et al. 2000). A person skilled in the art will also recognise that in adapted versions of the two-hybrid system and also other techniques (e.g. gel-retardation, immunoprecipitation, competitive inhibition), it is possible to study protein-oligonucleotide interactions, and therefor these techniques which use any of the sequences of the present invention are also within the scope of the invention.

The term "fragment of a sequence" or "part of a sequence" means a truncated sequence of the original sequence referred to. The truncated sequence (nucleic acid or protein sequence) can vary widely in length; the minimum size being a sequence of sufficient size to provide a sequence with at least a comparable function and/or activity or the original sequence referred to, while the maximum size is not critical. In some applications, the maximum size usually is not substantially greater than that required to provide the desired activity and/or function(s) of the original sequence. Typically, the truncated amino acid or nucleotide sequence will range from about 5 to about 60 amino acids in length. More typically, however, the sequence will be a maximum of about 50 amino acids in length, preferably a maximum of about 60 amino acids. It is usually desirable to select sequences of at least about 10, 12 or 15 amino acids or nucleotides, up to a maximum of about 20 or 25 amino acids or nucleotides.

The invention also includes methods for high throughput compound screening. The man skilled in the art can easily design such methods using one or several elements of the invention.

The compounds yet to be obtained or identified can be compounds that are able to bind to any of the nucleic acids, peptides or proteins involved in the process of processing precursor messenger RNA and are therefore useful in the method of the present invention. Said compound or plurality of compounds may be comprised in, for example, samples, e.g., cell extracts from, e.g., plants, animals or micro-organisms. Furthermore, said compound(s) may be known in the art but hitherto not known to be capable of suppressing or activating proteins involved in processing of precursor messenger RNA.

In the scope of the present invention is also included the introduction into a plant cell one or more recombinant nucleic acid molecules, such as a DNA molecule encoding a protein which when expressed in said plant cell at an effective amount increases or induces the expression of an endogenous polynucleotide acid according to the present invention or as defined in claims or increases or induces the activity of a polypeptide of claim.

The present invention is further described by reference to the following non-limiting figures and examples.

SHORT DESCRIPTION OF THE FIGURES

FIG. 1

Salt-tolerance phenotypes of yeast strains expressing the isolated *Arabidopsis* cDNA clones, U1A, Ct-SRL1 or RCY1, as determined by "drop-tests"; in which serial dilutions of saturated cultures of the different strains, and of the control strain containing the empty expression vector, are tested on plates, without salt or containing the indicated LiCl or NaCl concentrations.

FIG. 2

Amino acid sequences derived from the nucleotide sequences of clones RCY1 (A: SEQ ID NO 4) and Ct-SRL1 (B: SEQ ID NO 3). Dipeptides Arg-Ser. Arg-Glu and Arg-Asp. which define the RS domain, are written in bold letters. The underlined M in (A) marks the methionine residue used as initiator during expression in yeast of the RS domain of RCY1 (SEQ ID NO 21).

FIG. 3

Salt-tolerance phenotype of yeast strains expressing the amino-terminal (cyclin) domain of RCY1, its carboxy-terminal RS domain, or the full-length protein. Drop-tests were performed as in the experiment of FIG. 1.

FIG. 4

Salt-tolerance phenotype of transgenic *Arabidopsis* plants. T2 seeds from three independent transgenic lines (L1, L3 and L5, as an example of the 12 obtained lines), transformed with the Ct-SRL 1 cDNA under control of the 35S promoter from CaMV, were germinated on agar plates without (A) or with (B) 20mM LiCl. Seeds from wild-type plants (Wt) were used as control. All transgenic lines showed similar phenotypes.

FIG. 5

Sequences of the genes and proteins of the present invention.

EXAMPLES

Example 1

Plant Material

Seeds of the red beet (*Beta vulgaris* var. DITA, also referred to herein as "sugar beet"), were sown on pots containing a mixture of sand and vermiculite (1:1 w/w). The plants were grown under greenhouse conditions (8 hours at 20° C., 16 hours at 25° C. with supplementary lighting to stimulate a minimum of 12 hours photoperiod). They were periodically irrigated with a nutrient solution containing 2.4 g/l $Ca(NO_3)_2.4H_2O$, 1 g/l $KNO_3$, 1 g/l $MgSO_4.7H_2O$, 0.3 g/l $KH_2PO_4$, 5.6 mg/l Fe-quelate (Kelantren, Bayer), 1.1 mg/l $ZnSO_4.7H_2O$, 3.3 mg/l $MnO_4.H_2O$, 0.3 mg/l $CuSO_4.5H_2O$, 3.8 mg/l $H_3BO_3$, 0.18 mg/l $(NH_4)6Mo_7.4H_2O$. For the construction of the cDNA library, three-week-old plants were irrigated with 200 mM NaCl for 24 hours before harvesting.

Example 2

Yeast Strains and Culture Conditions

The *Saccharomyces cerevisiae* competent cells W303-1A (MATa ura3, leu2, his3, trp1, ade2, ena 1-4::HIS3) were transformed with the *Arabidopsis* cDNA library.

The *Saccharomyces cerevisiae* strain JM26 (MATa leu 2-3, 112 ura 3-1 trp1-1, ade 2-1 his3-11,15 can 1-100, ena 1-4:: HIS3, nha1:TRP1) provided by J. M. Mulet (Universidad Politécnica de Valencia, Instituto de Biologia Molecular y Cellular de Plantas) was used for the screening of the red beet cDNA library. Strain JM26 is a derivative of W303.1 A (Wallis et al., 1989, Cell 58: 409-419) with null mutations of the genes ENA1-4 and NHA1, encoding a $Na^+$-pumping ATPase and a $Na^+/H^+$ antiporter, respectively, responsible for most of the yeast sodium extrusion (Garciadeblas et al. 1993, Mol. Gen. Genet. 236, 363-368), (Bañuelos et al. 1998, Microbiology 144: 2749-2758).

The yeast cells were grown in either minimal synthetic glucose medium (SD) or rich medium (YPD). SD medium contained 2% glucose, 0.7% yeast nitrogen base without amino acids and 50 mM succinic acid, adjusted to pH 5 with Tris, plus the required amino acids [100 μg/ml leucine, 30 μg/ml adenine, 100 μg/ml methionine] as indicated. YPD medium contained 1% yeast extract, 2% Bacto peptone and 2% glucose. Media were supplemented with NaCl and LiCl as indicated in the figures and the examples. Solid media contained 2% bacteriological-grade agar.

Example 3

Construction of the cDNA Libraries

The construction of the *Arabidopsis thaliana* cDNA library in the vector pFL61 is described in Minet et al. (1992) Plant J. 2(3): 417-422.

For the construction of a red beet cDNA library induced by salt stress, the plant material as described in example 1 was used. Directional cDNAs were synthesised (cDNA synthesis kit, Stratagene) using poly(A)+ RNA prepared from leaves of salt-treated red beet plants. cDNAs were ligated into phage λPG15 vector and packaged using a Gigapack III gold packaging extract (Stratagene). This phage has inserted the excisable expression plasmid pYPGE15 (URA3 as a selection marker) that is usable directly for both *E. coli* and yeast complementation (Brunelli and Pall, 1993, Yeast 9: 1309-1318). A plasmid cDNA library was recovered from λPG15 by the cre-lox recombinase system (Brunelli and Pall, 1993, Yeast 9: 1309-1318).

Example 4

Screening and Isolation of cDNA Clones Conferring Salt Tolerance to Yeast

To screen for *Arabidopsis thaliana* cDNAs which increase salt tolerance in yeast, the cDNA library constructed in pFL61 was used to transform the yeast strain W303-1A by the LiCl method (Gietz et al. 1992, Nucleic Acids Res. 20: 1425). Transformants were screened for halotolerance in plates with minimal medium plus 25 mM and 50 mM LiCl, or as indicated in the figures, and containing 400 μM methionine. Resistant clones were subjected to fluoroorotic acid-induced plasmid loss (Boeke et al (1984) Mol. Gen. Genet. 197: 354-346) to select only those clones showing plasmid dependent LiCl tolerance. Results were confirmed in wild type strain and in the double mutant ena1-4::HIS3 tfp1::LEU2, defective in the vacuolar transport.

To screen for red beet cDNAs which increase salt tolerance in yeast, the cDNA library constructed in pYPGE15 was used to transform the yeast mutant strain JM26. Transformants selected on SD plates with leucine and adenine by uracil prototrophy were pooled and replated on screening medium (SD with leucine, adenine and methionine supplemented with 0.15 M NaCl) at a density of $2 \times 10^5$ cells per plate (12×12 cm). Methionine was added to the selective medium to avoid selection of the HAL2-like homologues already found in *Arabidopsis* (Quintero et al. 1996, Plant Cell 8: 529-537) (Gil-Mascarell et al. 1999, Plant J. 17(4): 373-383). Alternatively, for the selection of Li+ resistant yeast cells, the transformants were replated on screening medium (SD with leucine and adenin supplemented with 20 mM LiCl). The putative positive clones were rescreened on the same NaCl or LiCl medium.

Example 5

Determination of Intracellular Lithium Content

Yeast cells expressing the cDNA clones of the present invention or the control strain transformed with the empty vector, were grown to exponential phase and the medium was then supplemented with LiCl to 30 mM final concentration. 10 ml—samples were taken at different times and the intracellular lithium content was determined as described previously (Murgùia et al. 1996, J. Biol. Chem. 271: 29029-29033).

Example 6

Beta Galactosidase Assay

Yeast cells containing the *E. Coli* LacZ gene, interrupted or not with an intron (Legrain and Rosbash (1989), cell, 75: 573-583), under control of an galactose-inducible promoter, were transformed with the Ct-SRL1 cDNA in a yeast expression vector or, as a control, with the empty plasmid. Cultures were grown to exponential phase in glucose minimal medium, with or without 35 mM LCl, and then shifted to galactose medium, maintaining the same salt conditions, to induce the beta-galactosidase expression. Samples were collected at 0 (background value) and 4 hours after induction, and beta-galactosidase activity was measured in permeabilised cells as described (Serrano et al, 1973: Eur. J. Biochem. 34: 479-482).

Example 7

RT-PCR Assay

Yeast cells overexpressing the Ct-SRL cDNA or transformed with the empty vector were grown to exponential phase; the medium was then supplemented with LiCl to 150 mM final concentration and total RNA was purified at different times. Equal amounts of total RNA were digested with RNase-free DNaseI, and reverse-transcribed with M-MuLV RTase (Roche Molecular Biochemicals) using primer preSARlrp (5' CATCAAATCTTTCAGGG-3': SEQ ID NO. 23), that hybridises to the second SAR1 exon 277 nucleotides downstream from the 3'-splice site. It was followed by 15 cycles of PCR amplification with Netzyme (Molecular Netline Bioproducts) DNA polymerase, and primer preSAR1fp, (5'-CTTTATTTTACTGTACAG-3': SEQ ID NO. 24), which hybridises to the 3' end of the SAR1 intron. [$\alpha$-$^{32}$P]dCTP (740kBq, 110 TBq/mmol, Amersham) was added after the $5^{th}$ cycle and the products were resolved in 6% PA-urea gels and visualised by autoradiography. The relative intensity of the amplified bands was determined using a FUJI (Fujifilm BAS-1500) phosphorimager. Samples lacking reverse transcriptase ware used as controls.

Example 8

Transformation of Plants

The clones of the present invention, for example the *Arabidopsis* Ct-SRL1 cDNA, are subcloned into pBI121 (Clontech), in place of the GUS gene, and the resulting binary vector is introduced into the *Agrobacterium tumefaciens* strain C58C1 by electroporation. Transgenic plants, like *Arabidopsis* plants were obtained by in vivo infiltration as described in www.arabidopsis.org/protocols_Mundy2.html#trans.inf.

Alternatively, the genes of the present invention can be transformed to other dicotyledon or monocotyledon plants. Therefore they are cloned in the suitable plant transformation vector, such as a binary vector, under the control of plant operable regulatory sequences, such as a plant operable promoter and a plant operable terminator. These vectors comprising a gene of the present invention can be transformed into plants (such as a crop plant) using standard techniques well known by the person skilled in the art, such as *Agrobacterium* mediated gene transfer. The transgenic plant expressing the gene of the present invention are expected to show an increased tolerance to environmental stress, such as for example an increased tolerance to mineral salt toxicity. This increased tolerance can for example be observed by the ability of the transgenic plants to germinate in salt containing medium.

Example 9

Rice Transformation with the Genes of the Present Invention

The expression of red beet genes or *Arabidopsis thaliana* that are involved in salt tolerance in yeast in monocotyledons, such as for example Rice, can confer stress tolerance to that monocotyledoneous plant.

To transfer the stress tolerance activity of the genes of the present invention to monocots, the aforementioned genes (SEQ ID NO. 1, 2, 5, 7, 9, 11, 13, 15, 17 and 19), operably linked to a promoter, are each transformed to rice using the standard transformation procedures well known to the persons skilled in the art and outlined in the following paragraph. After several time periods ranging from 1 day to 1 or more weeks, the seedling is checked for the expression of the transformed gene. This is done by growing the seedlings in organogenesis medium, and checking the presence of the DNA or mRNA by PCR or reverse PCR. After the confirmation of gene expression the transformed rice plants are checked for the enhanced tolerance to stress situations including salt, drought and cold (see WO97/13843). This is done by growing the transformed rice plants in medium containing increased amounts of NaCl or LiCl. Also the increased resistance to cold or drought is tested by growing the transformed plants in suboptimal growing temperatures and suboptimal levels of humidity, respectively (WO97/13843).

*Agrobacterium*-Mediated Rice Transformation

The genes of the present invention are operably linked to a promoter and cloned into a vector. These vectors are transformed to *Agrobacterium tumefaciens* strain LBA4404 or C58 by means of electroporation and subsequently transformed bacterial cells are selected on a solid agar medium containing the appropriate antibiotics.

For demonstration of the expression of the genes of the current invention in rice, 309 mature dry seeds of the rice japonica cultivars Nipponbare or Taipei are dehusked, sterilised and germinated on a medium containing 2,4-dichlorophenoxyacetic acid (2,4-D). After incubation in the dark for four weeks, embryogenic, scutellum-derived calli are excised and propagated on the same medium. Selected embryogenic callus is then co-cultivated with *Agrobacterium*. Co-cultivated callus is grown on 2,4D-containing medium for 4 to 5 weeks in the dark in the presence of a suitable concentration of the appropriate selective agent. During this period, rapidly growing resistant callus islands develop. After transfer of this material to a medium with a reduced concentration of 2,4-D and incubation in the light, the embryogenic potential is released and shoots develop in the next four to five weeks. Shoots are excised from the callus and incubated for one week on an auxin-containing medium from which they can be transferred to the soil. Hardened shoots are grown under high humidity and short days in a phytotron. Seeds can be harvested three to five months after transplanting. The method yields single locus transformants at a rate of over 50% (Chan et al. 1993, Plant Mol. Biol. 22 :491-506) (Hiei et al. 1994, Plant J. 6: 271-282)

REFERENCE

An G., Watson B. D., Stachel S., Gordon M. P., & Nester E. W. (1985) New cloning vehicles for transformation of higher plants. *EMBO J.* 4, 277-284.

Armstrong C. L., Petersen W. P., Buchholz W. G., Bowen B. A., & Sulc S. L. (1990) Factors affecting PEG-mediated stable transformation of maize protoplasts. *Plant Cell Reports* 9, 335-339.

Baron M. H. & Baltimore D. (1982) Antibodies against the chemically synthesized genome-linked protein of poliovirus react with native virus-specific proteins. *Cell* 28, 395-404.

Bartel P. L. & Fields S. (1997) The Yeast Two-Hybrid System. Oxford University Press.

Bechtold N. & Pelletier G. (1998) in planta *Agrobacterium*-mediated transformation of adult *Arabidopsis thaliana* plants by vacuum infiltration. *Methods Mol.Biol.* 82, 259-266.

Cho R. J., Mindrinos M., Richards D. R., Sapolsky R. J., Anderson M., Drenkard E., Dewdney J., Reuber T. L., Stammers M., Federspiel N., Theologis A., Yang W. H., Hubbell E., Au M., Chung E. Y., Lashkari D., Lemieux B., Dean C., Lipshutz R. J., Ausubel F. M., Davis R. W., & Oefner P. J. (1999) Genome-wide mapping with biallelic markers in *Arabidopsis thaliana*. *Nat.Genet.* 23, 203-207.

Christou P., McCabe D. E., & Swain W. F. (1988) Stable transformation of soybean callus by DNA-coated gold particles. *Plant Physiol.* 87, 671-674.

Crossway A., Oakes J. V., Irvine J. M., Ward B., Knauf V. C., & Shewmaker C. K. (1986) Integration of foreign DNA following microinjection of tobacco mesophyll protoplasts. *Mol.Gen.Genet.* 202,179-185.

Dodds J. H. (1985) Plant genetic engineering. Cambridge University Press.

Fromm M., Taylor L. P., & Walbot V. (1985) Expression of genes transferred into monocot and dicot plant cells by electroporation. *Proc.Natl.Acad.Sci.U.S.A* 82, 5824-5828.

Hanahan D. (1983) Studies on transformation of *Escherichia coli* with plasmids. *J. Mol.Biol* 166, 557-580.

Hellens R. P., Edwards E. A., Leyland N. R., Bean S., & Mullineaux P. M. (2000) pGreen: a versatile and flexible binary Ti vector for *Agrobacterium*-mediated plant transformation. *Plant Mol.Biol.* 42, 819-832.

Herrera-Estrella L., De Block M., Messens E. H. J. P., Van Montagu M., & Schell J. (1983a) Chimeric genes as dominant selectable markers in plant cells. *EMBO J.* 2, 987-995.

Herrera-Estrella L., Depicker A., Van Montagu M., & Schell J. (1 983b) Expression of chimaeric genes transferred into plant cells using a Ti-plasmid-derived vector. *Nature* 303, 209-213.

Joung J. K., Ramm E. I., & Pabo C. O. (2000) A bacterial two-hybrid selection system for studying protein-DNA and protein-protein interactions. *Proc.NatLAcad. Sci.U.S.A* 97, 7382-7387.

Krens F. A., Molendijk L., Wullems G. J., & Schilperoort R. A. (1982) in vitro transformation of plant protoplasts with Ti-plasmid DNA. *Nature* 296, 72-74.

Langemeier J. L., Cook R. F., Issel C. J., & Montelaro R. C. (1994) Application of cycle dideoxy fingerprinting to screening heterogeneous populations of the equine infectious anemia virus. *Biotechniques* 17, 484-6, 488, 490.

Lerner R. A. (1982) Tapping the immunological repertoire to produce antibodies of predetermined specificity. Nature 299, 593-596.

Lerner R. A., Green N., Alexander H., Liu F. T., Sutcliffe J. G., & Shinnick T. M. (1981) Chemically synthesized peptides predicted from the nucleotide sequence of the hepatitis B virus genome elicit antibodies reactive with the native envelope protein of Dane particles. *Proc.NatLAcad. Sci.U.S.A* 78, 3403-3407.

Li-Sucholeiki X. C. , Khrapko K., Andre P. C., Marcelino L. A., Karger B. L., & Thilly W. G. (1999) Applications of constant denaturant capillary electrophoresis/high-fidelity polymerase chain reaction to human genetic analysis. *Electrophoresis* 20, 1224-1232.

Liddle J. E. & Cryer A. (1991) A Practical Guide to Monoclonal Antibodies. Wiley New York.

Loffler J., Langui D., Probst A., & Huber G. (1994) Accumulation of a 50 kDa N-terminal fragment of beta-APP695 in Alzheimer's disease hippocampus and neocortex. *Neurochem.Int.* 24, 281-288.

Magyar Z., Meszaros T., Miskolczi P., Deak M., Feher A., Brown S., Kondorosi E., Athanasiadis A., Pongor S., Bilgin M., Bako L., Koncz C., & Dudits D. (1997) Cell cycle phase specificity of putative cyclin-dependent kinase variants in synchronized alfalfa cells. *Plant Cell* 9, 223-235.

McCallum C. M., Comai L., Greene E. A., & Henikoff S. (2000b) Targeted screening for induced mutations. *Nat. Biotechnol.* 18, 455-457.

McCallum C. M., Comai L., Greene E. A., & Henikoff S. (2000a) Targeting induced local lesions IN genomes (TILLING) for plant functional genomics. *Plant Physiol* 123, 439-442.

Merrifield R. B. (1963) Solid phase peptide synthesis. I. The synthesis of a tetrapeptide. *J.Amer.Chem.Soc.* 85, 2149-2154.

Murakami T., Simonds W. F., & Spiegel A. M. (1992) Site-specific antibodies directed against G protein beta and gamma subunits: effects on alpha and beta gamma subunit interaction. *Biochemistry* 31, 2905-2911.

Palmgren G. (1997) Transgenic plants: environmentally safe factories of the future. *Trends Genet.* 13, 348.

Paszkowski J., Shillito R. D. , Saul M., Mandak V., & Hohn T. H. B. P. I. (1984) Direct gene transfer to plants. *EMBO J.* 3, 2717-2722.

Ross P., Hall L., & Haff L. A. (2000) Quantitative approach to single-nucleotide polymorphism analysis using MALDI-TOF mass spectrometry [In Process Citation]. *Biotechniques* 29, 620-629.

Sambrook J., Fritsch E. F. , & Maniatis T. (1989) Molecular Cloning: A Laboratory Manual. Cold Spring Harbor Laboratory Press.

Semler B. L., Anderson C. W., Hanecak R., Dorner L. F. , & Wimmer E. (1982) A membrane-associated precursor to poliovirus VPg identified by immunoprecipitation with antibodies directed against a synthetic heptapeptide. *Cell* 28, 405-412.

Shioda T., Andriole S., Yahata T., & Isselbacher K. J. (2000) A green fluorescent protein-reporter mammalian two-hybrid system with extrachromosomal maintenance of a prey expression plasmid: Application to interaction screening. *Proc.Natl.Acad.Sci.U.S.A* 97, 5220-5224.

Tamura R. N., Cooper H. M., Collo G., & Quaranta V. (1991) Cell type-specific integrin variants with alternative alpha chain cytoplasmic domains. *Proc.Natl.Acad.Sci.US.A* 88, 10183-10187.

Trieu A. T., Burleigh S. H., Kardailsky I. V., Maldonado-Mendoza I. E., Versaw W. K., Blaylock L. A., Shin H., Chiou T. J., Katagi H., Dewbre G. R., Weigel D., & Harrison M. J. (2000) Technical Advance: Transformation of Medicago truncatula via infiltration of seedlings or flowering plants with *Agrobacterium*. *Plant J.* 22, 531-541.

Vidal-Puig A. & Moller D. E. (1994) Comparative sensitivity of alternative single-strand conformation polymorphism (SSCP) methods. *Biotechniques* 17, 490-2, 494, 496.

Woulfe J., Lafortune L., de Nadai F., Kitabgi P., & Beaudet A. (1994) Post-translational processing of the neurotensin/neuromedin N precursor in the central nervous system of the rat-II. Immunohistochemical localization of maturation products. *Neuroscience* 60, 167-181.

Yoon K., Cole-Strauss A., & Kmiec E. B. (1996) Targeted gene correction of episomal DNA in mammalian cells mediated by a chimeric RNA.DNA oligonucleotide. *Proc. Natl.Acad.Sci.U.S.A* 93, 2071-2076.

The invention claimed is:

1. A method of enhancing salt stress tolerance in plants, plant cells or yeast cells, said method comprising overexpression of a nucleic acid molecule encoding an RS domain (SEQ ID NO:21) in said plants or said cells.

2. The method according to claim 1 which comprises overexpression of a nucleic acid molecule encoding an SR-like protein comprising said RS domain.

3. The method according to claim 2 wherein said SR-like protein is RCY1 (SEQ ID NO: 4).

4. The method according to claim 3 wherein the nucleic acid molecule encoding the SR-like protein has the sequence of SEQ ID NO: 2.

5. An isolated nucleic acid molecule encoding a protein selected from the group consisting of:
   (a) a nucleic acid molecule comprising the DNA sequence of SEQ ID NO: 2 or the complement thereof,
   (b) a nucleic acid molecule comprising the corresponding RNA sequence of SEQ ID NO: 2 as in (a) or the complement thereof,
   (c) a nucleic acid molecule encoding a protein having the amino acid sequence of SEQ ID NO: 4 or 21 or as defined in (a) or (b) characterized in that said sequence is DNA, cDNA, genomic DNA or synthetic DNA.

6. A vector comprising a nucleic acid molecule according to claim 5.

7. A vector according to claim 6 which is an expression vector wherein the nucleic acid molecule is operably linked to one or more control sequences allowing the expression of said nucleic acid molecule in prokaryotic and/or eukaryotic host cells.

8. A host cell comprising a nucleic acid molecule according to claim 5 or a vector according to claim 6 or 7.

9. A host cell comprising the vector of claim 7 wherein the host cell is a bacterial, insect, fungal, yeast, plant or animal cell.

10. An isolated polypeptide encoded by at least one of the nucleic acid molecules defined in claim 5.

11. The polypeptide of claim 10 comprising the amino acid sequence of SEQ ID NO: 4 or 21.

12. A method of producing a polypeptide according to claim 10 or 11 comprising culturing a host cell under conditions allowing expression of the polypeptide wherein said host cell comprises a vector comprising a nucleic acid molecule operably linked to one or more control sequences allowing expression of said nucleic acid molecule in prokaryotic or eukaryotic host cells and wherein the nucleic acid molecule is selected from the group consisting of
   (a) a nucleic acid molecule comprising the DNA sequence of SEQ ID NO: 2 or the complement thereof,
   (b) a nucleic acid molecule comprising the corresponding RNA sequence of SEQ ID NO: 2 as in (a) or the complement thereof,
   (c) a nucleic acid molecule encoding a protein having the amino acid sequence of SEQ ID NO: 4 or 21 or as defined in (a) or (b) characterized in that said sequence is DNA, cDNA, genomic DNA or synthetic DNA, and recovering the produced polypeptide from the culture.

13. A method for the production of a transgenic plant, plant cell or plant tissue comprising the introduction of a nucleic acid molecule according to claim 5 in an expressible format or a vector in said plant, plant cell or plant tissue.

14. A method for effecting the expression of a polypeptide of claim 10 or 11 comprising introduction and stable integration into the genome of a plant cell, of a nucleic acid molecule operably linked to one or more control sequences or a vector comprising a nucleic acid molecule operably linked to one or more control sequences, said nucleic acid molecule selected from the group consisting of
  (a) a nucleic acid molecule comprising the DNA sequence of SEQ ID NO: 2 or the complement thereof;
  (b) a nucleic acid molecule comprising the corresponding RNA sequence of SEQ ID NO: 2 as in (a) or the complement thereof; and
  (c) a nucleic acid molecule encoding a protein having the amino acid sequence of SEQ ID NO: 4 or 21 or as defined in (a) or (b) characterized in that said sequence is DNA, cDNA, genomic DNA or synthetic DNA.

15. The method of claim 13 further comprising regenerating a plant from said plant cell.

16. The transgenic plant cell obtainable by a method of claim 15 wherein said nucleic acid molecule is stably integrated into the genome of said plant cell.

17. A Transgenic plant tolerant to salt stress as a result of the expression of at least one of the nucleic acid molecules of claim 5.

18. A Transgenic plant which as a result of the expression of at least one of the nucleic acid molecules of claim 5 shows an alteration of its phenotype.

19. A harvestable part of a plant of claim 16 wherein said harvestable part comprises the nucleic acid molecule which was introduced into the transgenic plant.

20. The harvestable part of a plant of claim 19 selected from the group consisting of seeds, leaves, fruits, stem cultures, rhizomes, roots, tubers and bulbs.

21. Transgenic progeny derived from any of the plants or plant parts of claim 17 wherein said transgenic progeny comprises the nucleic acid molecule which was introduced into the parent plant.

22. The method of claim 1 for increasing yield of the harvestable biomass of plants.

23. A diagnostic composition comprising a nucleic acid molecule of claim 5.

24. A harvestable part of a plant of claim 18 wherein said harvestable part comprises the nucleic acid molecule which was introduced into the transgenic plant.

25. Transgenic progeny derived from any of the plants or plant parts of claim 18 wherein said transgenic progeny comprises the nucleic acid molecule which was introduced into the parent plant.

26. The method according to any of claims 1, 2 or 3 wherein said plant is *Arabidopsis thaliana* or said plant cells are *Arabidopsis thaliana* cells.

27. The method according to any of claims 1, 2 or 3 wherein said yeast cells are *Saccharomyces cerevisiae* cells.

28. A diagnostic composition comprising a vector of claim 6 or 7.

29. A diagnostic composition comprising a polypeptide of claim 10 or 11.

* * * * *

SEQUENCE LISTING

<160> NUMBER OF SEQ ID NOS: 24

<210> SEQ ID NO 1
<211> LENGTH: 840
<212> TYPE: DNA
<213> ORGANISM: Arabidopsis thaliana

<400> SEQUENCE: 1

```
caaaccttga gaagatgaat ttaccaacta aaccttctgg ttcaaccgga gacatgaccc       60
gtggctcaga agacactgcc cgtcgtccac catcagtaaa agcatctctc tctgtttcat      120
ttggtcagcg tgcacctcat cgtgcttcca ccagaggctc ttctcctgtt cgccgtcctc      180
caccgactgg ttatgacaga aatggaggcg atgaagtaca cagcggtcc ccacgtagaa       240
gccagagccg agactattat tctgacagag actcagatag acaacgggaa agagagaggg      300
agaaagaccg cgaaagagag aggggagggg atagatacag agaaagggag agggattatg      360
gtaatgatag gagatcaagg cgcgactatg atagtagaag caggcgcaat gattatgagg      420
acgacagaag tagacatgac cggagaagca ggagcagaag cagaagtagg agcaggagtg      480
tgcagattga gcgtgaaccg actcctaaaa gagatagtag caacaaagag aaatcggcgg      540
tgacagtgaa cagcaatctc gcaaagctaa aagatttgta tggagacgca agtagtcaga      600
aaagggatga aggatttgga acaaggaaag attcaagttc agaagaagtg ataaagcttg      660
gtggttcctc ttggaggtga aaaaacaaac aaaacaaaac caaactgtgg atttaaaatg      720
cttcttctat ttagcaggat gatgcatgtt gtttaactat actgttttga tttccagcaa      780
actatttgtc atatgcttta tattacagtt taagagttga tctttatctt gaaaaaaaaa      840
```

<210> SEQ ID NO 2
<211> LENGTH: 1433
<212> TYPE: DNA
<213> ORGANISM: Arabidopsis thaliana

<400> SEQUENCE: 2

```
gtttagtgaa tcgatgattt acactgctat cgacaatttt tacctaaccg acgagcagct       60
gaaggcttca ccttcgagga aagatgggat agatgaaaca actgaaatct ctcttagaat      120
ctatggatgt gatctcatcc aagagggtgg aatattgctc aaactaccac aggcagttat      180
ggctactggg caggttctgt ttcagcgatt ctattgcaag aagtctttgg ctaaatttga      240
tgtcaagata gttgctgcca gctgtgtatg gcttgcatca aaactggaag aaaaccctaa      300
aaaagctaga caggtcatca tcgtattcca caggatggag tgtcgcaggg agaacttgcc      360
attagaacat ctggatatgt atgccaagaa gttctctgag ttgaaagttg aattaagcag      420
aactgagaga catatactga agagatgggt ttttgtttgt catgttgaac atcctcacaa      480
gttcatatca aactaccttg ccacattaga aacacctcca gaattgaggc aagaagcttg      540
gaatttggcc aatgatagtc tgcgtacaac cctctgtgta aggttcagaa gtgaggttgt      600
ggcttgtggg gtagtgtatg ctgctgcccg taggtttcaa gtaccactcc ctgagaatcc      660
gccgtggtgg aaagcatttg atgcagataa atctagtatt gacgaagtgt gtagagttct      720
tgctcattta tacagtcttc caaaggctca gtatatctct gtttgcaagg atgggaagcc      780
atttacattt tctagcagat ccgggaattc tcaaggtcaa tcagcgacaa aggatctgtt      840
gccgggagca ggcgaggctg ttgatactaa atgtactgca ggatcagcta ataacgactt      900
gaaggatgga atggttacta caccacacga aaaggctaca gattccaaga aaagtggtac      960
```

```
cgagtcaaac tctcagccaa ttgtaggaga ctcaagctat gaaagaagta aagtaggaga    1020
tagagaaaga gagagtgata gagagaagga acgaggtaga gagagggaca ggggtaggtc    1080
tcacagaggc agagattctg acagagacag tgatagggag agagacaaac tcaaagatcg    1140
aagtcatcat cggtcaagag acagattgaa ggattcaggt ggacattcag ataaatcaag    1200
gcatcattct tctcgggacc gtgactaccg cgactcatcg aaagaccgtc gtaggcacca    1260
ttaagccaat cttcttgtca tctacatccc cttgagccta cttgatgtta agacagtata    1320
gtgttgtatt gtgttaagag tcaaacccca tgtgtactta atcacatgct aagatcacgt    1380
tggttcgaca tataaatcga gaaagtctga tatgtttcta aaaaaaaaaa aaa           1433
```

<210> SEQ ID NO 3
<211> LENGTH: 221
<212> TYPE: PRT
<213> ORGANISM: Arabidopsis thaliana

<400> SEQUENCE: 3

```
Met Asn Leu Pro Thr Lys Pro Ser Gly Ser Thr Gly Asp Met Thr Arg
 1               5                  10                  15

Gly Ser Glu Asp Thr Ala Arg Arg Pro Ser Val Lys Ala Ser Leu
             20                  25                  30

Ser Val Ser Phe Gly Gln Arg Ala Pro His Arg Ala Ser Thr Arg Gly
         35                  40                  45

Ser Ser Pro Val Arg Arg Pro Pro Thr Gly Tyr Asp Arg Asn Gly
     50                  55                  60

Gly Asp Glu Val Gln Gln Arg Ser Pro Arg Arg Ser Gln Ser Arg Asp
 65                  70                  75                  80

Tyr Tyr Ser Asp Arg Asp Ser Asp Arg Gln Arg Glu Arg Glu Arg Glu
                 85                  90                  95

Lys Asp Arg Glu Arg Glu Arg Gly Arg Asp Arg Tyr Arg Glu Arg Glu
            100                 105                 110

Arg Asp Tyr Gly Asn Asp Arg Arg Ser Arg Arg Asp Tyr Asp Ser Arg
        115                 120                 125

Ser Arg Arg Asn Asp Tyr Glu Asp Asp Arg Ser Arg His Asp Arg Arg
    130                 135                 140

Ser Arg Ser Arg Ser Arg Ser Arg Ser Arg Ser Val Gln Ile Glu Arg
145                 150                 155                 160

Glu Pro Thr Pro Lys Arg Asp Ser Ser Asn Lys Glu Lys Ser Ala Val
                165                 170                 175

Thr Val Asn Ser Asn Leu Ala Lys Leu Lys Asp Leu Tyr Gly Asp Ala
            180                 185                 190

Ser Ser Gln Lys Arg Asp Glu Gly Phe Gly Thr Arg Lys Asp Ser Ser
        195                 200                 205

Ser Glu Glu Val Ile Lys Leu Gly Gly Ser Ser Trp Arg
    210                 215                 220
```

<210> SEQ ID NO 4
<211> LENGTH: 416
<212> TYPE: PRT
<213> ORGANISM: Arabidopsis thaliana

<400> SEQUENCE: 4

```
Met Ile Tyr Thr Ala Ile Asp Asn Phe Tyr Leu Thr Asp Glu Gln Leu
 1               5                  10                  15

Lys Ala Ser Pro Ser Arg Lys Asp Gly Ile Asp Glu Thr Thr Glu Ile
             20                  25                  30
```

```
Ser Leu Arg Ile Tyr Gly Cys Asp Leu Ile Gln Glu Gly Gly Ile Leu
         35                  40                  45

Leu Lys Leu Pro Gln Ala Val Met Ala Thr Gly Gln Val Leu Phe Gln
     50                  55                  60

Arg Phe Tyr Cys Lys Lys Ser Leu Ala Lys Phe Asp Val Lys Ile Val
 65                  70                  75                  80

Ala Ala Ser Cys Val Trp Leu Ala Ser Lys Leu Glu Glu Asn Pro Lys
                 85                  90                  95

Lys Ala Arg Gln Val Ile Ile Val Phe His Arg Met Glu Cys Arg Arg
             100                 105                 110

Glu Asn Leu Pro Leu Glu His Leu Asp Met Tyr Ala Lys Lys Phe Ser
         115                 120                 125

Glu Leu Lys Val Glu Leu Ser Arg Thr Glu Arg His Ile Leu Lys Glu
     130                 135                 140

Met Gly Phe Val Cys His Val Glu His Pro His Lys Phe Ile Ser Asn
145                 150                 155                 160

Tyr Leu Ala Thr Leu Glu Thr Pro Pro Glu Leu Arg Gln Glu Ala Trp
                 165                 170                 175

Asn Leu Ala Asn Asp Ser Leu Arg Thr Thr Leu Cys Val Arg Phe Arg
             180                 185                 190

Ser Glu Val Val Ala Cys Gly Val Val Tyr Ala Ala Arg Arg Phe
         195                 200                 205

Gln Val Pro Leu Pro Glu Asn Pro Pro Trp Trp Lys Ala Phe Asp Ala
     210                 215                 220

Asp Lys Ser Ser Ile Asp Glu Val Cys Arg Val Leu Ala His Leu Tyr
225                 230                 235                 240

Ser Leu Pro Lys Ala Gln Tyr Ile Ser Val Cys Lys Asp Gly Lys Pro
                 245                 250                 255

Phe Thr Phe Ser Ser Arg Ser Gly Asn Ser Gln Gly Gln Ser Ala Thr
             260                 265                 270

Lys Asp Leu Leu Pro Gly Ala Gly Glu Ala Val Asp Thr Lys Cys Thr
         275                 280                 285

Ala Gly Ser Ala Asn Asn Asp Leu Lys Asp Gly Met Val Thr Thr Pro
     290                 295                 300

His Glu Lys Ala Thr Asp Ser Lys Lys Ser Gly Thr Glu Ser Asn Ser
305                 310                 315                 320

Gln Pro Ile Val Gly Asp Ser Ser Tyr Glu Arg Ser Lys Val Gly Asp
                 325                 330                 335

Arg Glu Arg Glu Ser Asp Arg Glu Lys Glu Arg Gly Arg Glu Arg Asp
             340                 345                 350

Arg Gly Arg Ser His Arg Gly Arg Asp Ser Asp Arg Asp Ser Asp Arg
         355                 360                 365

Glu Arg Asp Lys Leu Lys Asp Arg Ser His Arg Ser Arg Asp Arg
     370                 375                 380

Leu Lys Asp Ser Gly Gly His Ser Asp Lys Ser Arg His His Ser Ser
385                 390                 395                 400

Arg Asp Arg Asp Tyr Arg Asp Ser Ser Lys Asp Arg Arg Arg His His
                 405                 410                 415

<210> SEQ ID NO 5
<211> LENGTH: 920
<212> TYPE: DNA
<213> ORGANISM: Arabidopsis thaliana
```

<400> SEQUENCE: 5

```
ccacgcgtcc gagagatttg gtgaagacga tggagatgca agaggctaat caaggaggag    60
gatcggaggt ttctccgaat cagacgattt acatcaacaa tctcaacgaa aaagtgaagc   120
ttgatgagct gaagaaatcg ctgaatgcag tgttctctca gttcgggaag atactggaga   180
tattggcgtt taagaccttt aagcacaaag acaagcttg ggtagtcttc gacaacaccg   240
agtctgcttc cactgctatt gctaaaatga ataattttcc tttctacgac aaggagatga   300
gaatacaata tgccaaaaca aaatcagatg ttgttgccaa ggccgatggt acatttgttc   360
ctcgcgagaa gagaaagaga catgaggaga aggaggcgg caagaaaaag aaagaccagc   420
accatgattc tacacagatg ggcatgccca tgaactcagc atatccaggt gtctatggag   480
ctgcacctcc tctatcgcaa gtaccatacc ctggtggcat gaaacccaat atgcccgagg   540
caccagctcc gccaaataat attctctttg tccaaaacct tcctcacgag acaactccaa   600
tggtgcttca gatgttgttc tgccagtacc aaggatttaa ggaagttaga atgattgaag   660
ccaaaccggg aatcgccttt gtggagtttg ctgatgagat gcagtcgacg gtcgcaatgc   720
agggacttca aggtttcaag attcagcaaa accagatgct catcacgtat gccaagaaat   780
agacaatttc gttttatttg tgtttcgatg agatatgttt gtatctgtca atgttacttc   840
ttgccatggg ggctgtcttc tgggttgtgt gatgctagat atccctctct acttacattt   900
tttcatcaaa aaaaaaaaaa                                               920
```

<210> SEQ ID NO 6
<211> LENGTH: 250
<212> TYPE: PRT
<213> ORGANISM: Arabidopsis thaliana

<400> SEQUENCE: 6

```
Met Glu Met Gln Glu Ala Asn Gln Gly Gly Gly Ser Glu Val Ser Pro
  1               5                  10                  15

Asn Gln Thr Ile Tyr Ile Asn Asn Leu Asn Glu Lys Val Lys Leu Asp
             20                  25                  30

Glu Leu Lys Lys Ser Leu Asn Ala Val Phe Ser Gln Phe Gly Lys Ile
         35                  40                  45

Leu Glu Ile Leu Ala Phe Lys Thr Phe Lys His Lys Gly Gln Ala Trp
     50                  55                  60

Val Val Phe Asp Asn Thr Glu Ser Ala Ser Thr Ala Ile Ala Lys Met
 65                  70                  75                  80

Asn Asn Phe Pro Phe Tyr Asp Lys Glu Met Arg Ile Gln Tyr Ala Lys
                 85                  90                  95

Thr Lys Ser Asp Val Val Ala Lys Ala Asp Gly Thr Phe Val Pro Arg
            100                 105                 110

Glu Lys Arg Lys Arg His Glu Glu Lys Gly Gly Gly Lys Lys Lys Lys
        115                 120                 125

Asp Gln His His Asp Ser Thr Gln Met Gly Met Pro Met Asn Ser Ala
    130                 135                 140

Tyr Pro Gly Val Tyr Gly Ala Ala Pro Pro Leu Ser Gln Val Pro Tyr
145                 150                 155                 160

Pro Gly Gly Met Lys Pro Asn Met Pro Glu Ala Pro Ala Pro Pro Asn
                165                 170                 175

Asn Ile Leu Phe Val Gln Asn Leu Pro His Glu Thr Thr Pro Met Val
            180                 185                 190
```

```
Leu Gln Met Leu Phe Cys Gln Tyr Gln Gly Phe Lys Glu Val Arg Met
        195                 200                 205
Ile Glu Ala Lys Pro Gly Ile Ala Phe Val Glu Phe Ala Asp Glu Met
    210                 215                 220
Gln Ser Thr Val Ala Met Gln Gly Leu Gln Gly Phe Lys Ile Gln Gln
225                 230                 235                 240
Asn Gln Met Leu Ile Thr Tyr Ala Lys Lys
                245                 250

<210> SEQ ID NO 7
<211> LENGTH: 1492
<212> TYPE: DNA
<213> ORGANISM: Beta vulgaris

<400> SEQUENCE: 7 tcctctctttt aacctaatt tgagctctca ttatcctgat ttttttcaacc atggatgctc      60
agagagctct ctcgatgaa ttaatgggcg cagctcgaaa tctgactgat gaagaaaaga     120
aaggttatag agagataaag tgggatgaca aggaagtttg tgcgccgtat atgattcgat     180
tttgccctca cgatctcttc gtcaatactc gaagtgatct tggaccatgt ccaagagttc     240
atgaccaaaa gctgaaagag agctttgaga actctccaag gcatgactca tatgtcccac     300
gttttgaagc agagcttgcc caattttgtg agaagctggt ggcagatttg gataggaaag     360
taagacgtgg gagagagcgg ctggaccagg aggttgaacc tccacctccc cctcctattt     420
ctgcagaaaa agctgagcag ctatctgtac ttgaagagaa aataaaaaat ttgcttgaac     480
aagtagagtc actgggagaa gctggcaaag tcgatgaagc agaagcactc atgcgaaagg     540
tggaaagtct taatttagag aaagctgcat taactcaaca gccccagaat gcagcaacaa     600
tgcttaccca agaaaaaag atggcactat gtgaaatttg cggttccttc ctggtagcca     660
atgatgctgt ggaaagaact caatctcata taactggcaa gcagcatatt ggctatggca     720
tggtccgtga ttaccttgct gagtataagg aggctaagga aaggcaagaa gaagaggaaa     780
gattagcaag ggagaaagaa gcagaagaac gtcggaagca gagggaaaag gaaaatgaga     840
gtaaaaacag aagaagcatc tccagtgaga gggaccgtca tcgtgatagg gattatggcc     900
gagatcgtga agatcacgaa gaatggaaca atagggggaa tcgagacgag ggaagaggaa     960
tggatcggag aaggcaatat gatcgcaatg aagggatgg agggaggaat acgtatcatg    1020
gtcgtgaacg tgaaaggagc aggtcacggt cccctgttag gcatggccac cggaggtgat    1080
ctaagagtgc tggttgccga tattagtagg cagtgggttg tgtagataaa cgatgatctt    1140
aaacctactg aggtagatgc tttatatctc aagatgtttt gtgtctgttt tcgaggtgtt    1200
gcattgcagt cttattgggg gttaaacttt tctttattgt cccacagtgt tgagactata    1260
ctgtctcctc tcatcaatct tgttagaggt caaagagatt gaggtaggta aaacttcatc    1320
gttgtaatct tacctatagt caacttgagt tttgtccaat tatagcacat ggtctttgaa    1380
acatttttta atcatgcggg ggtacgcaag aaaatatgca actatgctgc atggcttgtg    1440
tgcaaaaaaa aaaaaaaaaa aaaaaactcg agggggggcc cggtaccaag at           1492

<210> SEQ ID NO 8
<211> LENGTH: 342
<212> TYPE: PRT
<213> ORGANISM: Beta vulgaris
```

<400> SEQUENCE: 8

```
Met Asp Ala Gln Arg Ala Leu Leu Asp Glu Leu Met Gly Ala Ala Arg
 1               5                  10                  15

Asn Leu Thr Asp Glu Glu Lys Lys Gly Tyr Arg Glu Ile Lys Trp Asp
             20                  25                  30

Asp Lys Glu Val Cys Ala Pro Tyr Met Ile Arg Phe Cys Pro His Asp
         35                  40                  45

Leu Phe Val Asn Thr Arg Ser Asp Leu Gly Pro Cys Pro Arg Val His
     50                  55                  60

Asp Gln Lys Leu Lys Glu Ser Phe Glu Asn Ser Pro Arg His Asp Ser
 65                  70                  75                  80

Tyr Val Pro Arg Phe Glu Ala Glu Leu Ala Gln Phe Cys Glu Lys Leu
                 85                  90                  95

Val Ala Asp Leu Asp Arg Lys Val Arg Arg Gly Arg Glu Arg Leu Asp
             100                 105                 110

Gln Glu Val Glu Pro Pro Pro Pro Pro Ile Ser Ala Glu Lys Ala
         115                 120                 125

Glu Gln Leu Ser Val Leu Glu Glu Lys Ile Lys Asn Leu Leu Glu Gln
     130                 135                 140

Val Glu Ser Leu Gly Glu Ala Gly Lys Val Asp Glu Ala Glu Ala Leu
145                 150                 155                 160

Met Arg Lys Val Glu Ser Leu Asn Leu Glu Lys Ala Ala Leu Thr Gln
                 165                 170                 175

Gln Pro Gln Asn Ala Ala Thr Met Leu Thr Gln Glu Lys Lys Met Ala
             180                 185                 190

Leu Cys Glu Ile Cys Gly Ser Phe Leu Val Ala Asn Asp Ala Val Glu
         195                 200                 205

Arg Thr Gln Ser His Ile Thr Gly Lys Gln His Ile Gly Tyr Gly Met
     210                 215                 220

Val Arg Asp Tyr Leu Ala Glu Tyr Lys Glu Ala Lys Glu Lys Ala Arg
225                 230                 235                 240

Glu Glu Glu Arg Leu Ala Arg Glu Lys Glu Ala Glu Glu Arg Arg Lys
                 245                 250                 255

Gln Arg Glu Lys Glu Asn Glu Ser Lys Asn Arg Arg Ser Ile Ser Ser
             260                 265                 270

Glu Arg Asp Arg His Arg Asp Arg Asp Tyr Gly Arg Asp Arg Glu Arg
         275                 280                 285

Ser Arg Glu Trp Asn Asn Arg Gly Asn Arg Asp Glu Gly Arg Gly Met
     290                 295                 300

Asp Arg Arg Arg Gln Tyr Asp Arg Asn Gly Arg Asp Gly Gly Arg Asn
305                 310                 315                 320

Thr Tyr His Gly Arg Glu Arg Glu Arg Ser Arg Ser Arg Ser Pro Val
                 325                 330                 335

Arg His Gly His Arg Arg
             340
```

<210> SEQ ID NO 9
<211> LENGTH: 650
<212> TYPE: DNA
<213> ORGANISM: Beta vulgaris

<400> SEQUENCE: 9

```
acgaacaaca aaaatggcgg cagcagatgt tgaagcagta gacttcgaac ctgaagaaga      60
tgatctcatg gacgaagatg gcggtgcggc tgaagctgac ggctctcctc gagctcctca     120
```

```
ccctaagatt aaatcagcca ttactggcgc cggagctcca tcttctggcg gcttcggagc    180
taagaaaact aaaggtcgcg gcttccgtga agacgccgat gctgagcgta acagccgtat    240
gactgctcgt gaatttgatt ctcttgactc cgatggtgga cctggtcctg ctcgatcaat    300
tgagggctgg attatacttg tcacgggagt gcatgaagag gctcaagaag aggatctcct    360
taatgtcttt ggagagtttg gccagcttaa gaatttgcat ttgaatctgg atcgtcgtac    420
tgggtttgtc aagggttatg cattgatcga gtatgagaag tttgaagaag cacaagctgc    480
aataaaggag atgaatggtg ccaaaatgct tgagcagccg ataaatgttg attgggcatt    540
ctgcaatggt ccttacagga ggaggggcaa ccgaagaaga tccccacgtg gtcaccgatc    600
aaggagtcct agaagaagat attaaatctg tttgctgcat gtggaagttg                650
```

<210> SEQ ID NO 10
<211> LENGTH: 203
<212> TYPE: PRT
<213> ORGANISM: Beta vulgaris

<400> SEQUENCE: 10

Met Ala Ala Ala Asp Val Glu Ala Val Asp Phe Glu Pro Glu Glu Asp
 1               5                  10                  15

Asp Leu Met Asp Glu Asp Gly Gly Ala Ala Glu Ala Asp Gly Ser Pro
                20                  25                  30

Arg Ala Pro His Pro Lys Ile Lys Ser Ala Ile Thr Gly Ala Gly Ala
             35                 40                  45

Pro Ser Ser Gly Gly Phe Gly Ala Lys Lys Thr Lys Gly Arg Gly Phe
         50                 55                  60

Arg Glu Asp Ala Asp Ala Glu Arg Asn Ser Arg Met Thr Ala Arg Glu
 65              70                  75                  80

Phe Asp Ser Leu Asp Ser Asp Gly Gly Pro Gly Pro Ala Arg Ser Ile
                85                  90                  95

Glu Gly Trp Ile Ile Leu Val Thr Gly Val His Glu Glu Ala Gln Glu
            100                 105                 110

Glu Asp Leu Leu Asn Val Phe Gly Glu Phe Gly Gln Leu Lys Asn Leu
        115                 120                 125

His Leu Asn Leu Asp Arg Arg Thr Gly Phe Val Lys Gly Tyr Ala Leu
    130                 135                 140

Ile Glu Tyr Glu Lys Phe Glu Glu Ala Gln Ala Ala Ile Lys Glu Met
145                 150                 155                 160

Asn Gly Ala Lys Met Leu Glu Gln Pro Ile Asn Val Asp Trp Ala Phe
                165                 170                 175

Cys Asn Gly Pro Tyr Arg Arg Arg Gly Asn Arg Arg Ser Pro Arg
            180                 185                 190

Gly His Arg Ser Arg Ser Pro Arg Arg Tyr
        195                 200

<210> SEQ ID NO 11
<211> LENGTH: 1464
<212> TYPE: DNA
<213> ORGANISM: Beta vulgaris

<400> SEQUENCE: 11

```
ttttgtagca tttgattttt gctgaaaaac ccaattcata ttttgaagaa atgacaacaa     60
tgaacccttt tgatttgttg ggtgacaatg ataacgatga cccatctcag cttttagagt    120
ctgcaactgc tcagttgcag aaaattgctg ttaaaaaaac cccaactcag gttgctcaac    180
```

-continued

```
aacctcagca acagaaagct gcaaagttac ccaccaaacc tcttcctcca actcaagctg    240
tccgggaggc aaagaatgat tcccagcgcg gagggggggcg tggaggaggt cgcggtagtg    300
gccgtgggcg tggtggatac aatagggact actcaaacaa tgaaaatgct tttaacagca    360
ctggagtaac tggcagtcaa ggggatgatg gggaaaggga aggcgaccct tatgcgggac    420
ctcgtggccc ttatcgtggt ggtcgccgag atgggttcaa caatgaggag gaagagacg     480
gggaacgccc gcgtagaacc tatgagcgac gaagtggac tgggcgtgga agtgagatca    540
aacgtgaggg agcaggacgt ggaaactggg gtgctgaatc agatgaagtt gcaccggtta    600
ctgaggaagc tggagaacaa aatgagaaga agttgaaccc tgagaatctt ccagctgtag    660
aagatgctgc tgatggcatc aaggagggcc agccagatga gactgaagaa aaggaaccag    720
aggaaaagga gatgacactt gaagagtatg agaagttgct ggaagagaag aggaaggctt    780
tatcagcact caaggctgag gaacgcaagg tggaggttga caaagatttc gagtccatgc    840
aacagcttat aaacaaaaaa aaggatgaag actcagtttt catcaaattg ggttctgaca    900
aggataagaa gaaggaagca gctgaaaagg agaaagtgaa gaagtctgtc agcattaatg    960
aatttctgaa gcctgctgaa ggggatagat atggtggtcg tggcagggga cgtggtcgtg   1020
gcccaagagg tggtggatat ggtggaggta ataggatgtt tagtacgtct gctccagcaa   1080
tcgaagatcc aggggagttc ccaaccctag gtggcaagtg aggccacatc tttgaacttt   1140
ggtctctatt tggggtttta cttgaccccc tctgatttta agtcatttga gtgacaggaa   1200
tggacttcca gctgtgggtt tcctgtacca aatccacttt taagaaaatt tttatgcttt   1260
ttaaatttgt atatttattc tgttaaaaaa aaaaaaaaa actcgtgccg aattcgatat   1320
caagcttatc gataccgtcg acctcgaggg ggggcccggt accaagatgg cctttggtgg   1380
gttgaagaag gaaaaagaca gaaacgactt aattaccttac ttgaaaaaag cctgtgagta   1440
aacaggcccc ttttcctttg tcga                                         1464
```

<210> SEQ ID NO 12
<211> LENGTH: 356
<212> TYPE: PRT
<213> ORGANISM: Beta vulgaris

<400> SEQUENCE: 12

```
Met Thr Thr Met Asn Pro Phe Asp Leu Leu Gly Asp Asn Asp Asn Asp
  1               5                  10                  15

Asp Pro Ser Gln Leu Leu Glu Ser Ala Thr Ala Gln Leu Gln Lys Ile
             20                  25                  30

Ala Val Lys Lys Thr Pro Thr Gln Val Ala Gln Gln Pro Gln Gln Gln
         35                  40                  45

Lys Ala Ala Lys Leu Pro Thr Lys Pro Leu Pro Thr Gln Ala Val
     50                  55                  60

Arg Glu Ala Lys Asn Asp Ser Gln Arg Gly Gly Gly Arg Gly Gly Gly
 65                  70                  75                  80

Arg Gly Ser Gly Arg Gly Arg Gly Gly Tyr Asn Arg Asp Tyr Ser Asn
                 85                  90                  95

Asn Glu Asn Ala Phe Asn Ser Thr Gly Val Thr Gly Ser Gln Gly Asp
            100                 105                 110

Asp Gly Glu Arg Glu Arg Arg Pro Tyr Ala Gly Pro Arg Gly Pro Tyr
        115                 120                 125

Arg Gly Gly Arg Arg Asp Gly Phe Asn Asn Glu Glu Gly Arg Asp Gly
    130                 135                 140
```

```
Glu Arg Pro Arg Arg Thr Tyr Glu Arg Arg Ser Gly Thr Gly Arg Gly
145                 150                 155                 160

Ser Glu Ile Lys Arg Glu Gly Ala Gly Arg Gly Asn Trp Gly Ala Glu
            165                 170                 175

Ser Asp Glu Val Ala Pro Val Thr Glu Glu Ala Gly Glu Gln Asn Glu
        180                 185                 190

Lys Lys Leu Asn Pro Glu Asn Leu Pro Ala Val Glu Asp Ala Ala Asp
    195                 200                 205

Gly Ile Lys Glu Gly Gln Pro Asp Glu Thr Glu Glu Lys Glu Pro Glu
210                 215                 220

Glu Lys Glu Met Thr Leu Glu Glu Tyr Glu Lys Leu Leu Glu Glu Lys
225                 230                 235                 240

Arg Lys Ala Leu Ser Ala Leu Lys Ala Glu Glu Arg Lys Val Glu Val
                245                 250                 255

Asp Lys Asp Phe Glu Ser Met Gln Gln Leu Ile Asn Lys Lys Lys Asp
            260                 265                 270

Glu Asp Ser Val Phe Ile Lys Leu Gly Ser Asp Lys Asp Lys Lys Lys
        275                 280                 285

Glu Ala Ala Glu Lys Glu Lys Val Lys Lys Ser Val Ser Ile Asn Glu
    290                 295                 300

Phe Leu Lys Pro Ala Glu Gly Asp Arg Tyr Gly Gly Arg Gly Arg Gly
305                 310                 315                 320

Arg Gly Arg Gly Pro Arg Gly Gly Tyr Gly Gly Asn Arg Met
                325                 330                 335

Phe Ser Thr Ser Ala Pro Ala Ile Glu Asp Pro Gly Glu Phe Pro Thr
            340                 345                 350

Leu Gly Gly Lys
        355

<210> SEQ ID NO 13
<211> LENGTH: 1310
<212> TYPE: DNA
<213> ORGANISM: Beta vulgaris

<400> SEQUENCE: 13
ccgacaagtt agggttttc caagggtttt ctgaaaaaca gcgaataaca atggcaacca      60
ctaacccttt cgacttgctc gacgacgatg ctgaggaccc agccctcctt attgctgcgc     120
aggagcagaa ggtttccgcc gtcgttgccg gagataagaa aactccggca gtcgctgcta     180
agcctgctaa actccctact aagcctcttc ctccttctca agctgtgaga gaggcaagga     240
atgatggtgg tcgtggtgga ggtggccgcg ggggccgtgg ttatgggcgg ggacgtggtc     300
caggtggacc taatagagat tcaacaaata atgatgaaat atatcccaac gagaatgggg     360
gttctatggg atataggag gacagagata agccatctga agacgtgga ggatatggcg     420 gtcctcgtgg tggttatcgt ggaggacgac gtggaggtta tgataatgga gaagctgctg     480
aaggagaacg tcctaggagg atgtatgaac gccgtagtgg cactggacga ggaggtgaga     540
ttaaacgtga gggttctggt cgtgtgaaact ggggatctcc tactgatgag atagctccgg     600
agactgaaga acctgttgtg gaaaatgaag cagctgttgc agctgataag ccagcaggag     660
agggagaaaa tgttgatgct gaaaggaga gtcaagagaa ggaagttgta gaagcagagc     720
ctgaagaaaa ggaaatgact cttgaggagt atgagaaggt attggaggag aagaggaagg     780
ccttgctatc attgaaaggg gaggaaagaa aggtggattt ggacaaggag tttgaatcta     840
tgcagctggt ttcaaagaag aagaatgatg atgaggtttt cataaagctg ggttctgata     900
```

```
aggacaagag aaaggaggct gcagaaagag aagaaaggtc caagaagtct gtgagcatca    960
atgaatttct taagcctgcc gagggtgacg gataccacag gcgtggaaga ggaagaggcc   1020
gtggtggtag gggaggctat ggtgaggat acggcatgaa caatgcatct gctccttcta   1080
ttgaggatcc caatcaattc ccatctttgg gtgcgaactg agttttttgtc cgttgttgtc   1140 ttagttattt ttgggtcttt cttatatttt gagacttatt tatgatgttc aggagcctca   1200
tcaattacaa aaaagatat ttgacaggaa taatgtgttt ttcctgtgtt aagagtgtaa   1260
atcttagatg tttcatcttt caaaaaaaaa aaaaaaact cgaggggggg               1310
```

```
<210> SEQ ID NO 14
<211> LENGTH: 356
<212> TYPE: PRT
<213> ORGANISM: Beta vulgaris

<400> SEQUENCE: 14
```

```
Met Ala Thr Thr Asn Pro Phe Asp Leu Leu Asp Asp Ala Glu Asp
  1               5                  10                  15

Pro Ala Leu Leu Ile Ala Ala Gln Glu Gln Lys Val Ser Ala Val Val
                 20                  25                  30

Ala Gly Asp Lys Lys Thr Pro Ala Val Ala Ala Lys Pro Ala Lys Leu
             35                  40                  45

Pro Thr Lys Pro Leu Pro Pro Ser Gln Ala Val Arg Glu Ala Arg Asn
         50                  55                  60

Asp Gly Gly Arg Gly Gly Gly Arg Gly Gly Arg Gly Tyr Gly Arg
 65                  70                  75                  80

Gly Arg Gly Pro Gly Gly Pro Asn Arg Asp Ser Thr Asn Asn Asp Glu
                 85                  90                  95

Ile Tyr Pro Asn Glu Asn Gly Gly Ser Met Gly Tyr Arg Glu Asp Arg
            100                 105                 110

Asp Lys Pro Ser Glu Arg Arg Gly Gly Tyr Gly Gly Pro Arg Gly Gly
        115                 120                 125

Tyr Arg Gly Gly Arg Arg Gly Gly Tyr Asp Asn Gly Glu Ala Ala Glu
    130                 135                 140

Gly Glu Arg Pro Arg Arg Met Tyr Glu Arg Arg Ser Gly Thr Gly Arg
145                 150                 155                 160

Gly Gly Glu Ile Lys Arg Glu Gly Ser Gly Arg Gly Asn Trp Gly Ser
                165                 170                 175

Pro Thr Asp Glu Ile Ala Pro Glu Thr Glu Glu Pro Val Val Glu Asn
            180                 185                 190

Glu Ala Ala Val Ala Ala Asp Lys Pro Ala Gly Glu Gly Glu Asn Val
        195                 200                 205

Asp Ala Glu Lys Glu Ser Gln Glu Lys Glu Val Val Glu Ala Glu Pro
    210                 215                 220

Glu Glu Lys Glu Met Thr Leu Glu Glu Tyr Glu Lys Val Leu Glu Glu
225                 230                 235                 240

Lys Arg Lys Ala Leu Leu Ser Leu Lys Gly Glu Glu Arg Lys Val Asp
                245                 250                 255

Leu Asp Lys Glu Phe Glu Ser Met Gln Leu Val Ser Lys Lys Asn
            260                 265                 270

Asp Asp Glu Val Phe Ile Lys Leu Gly Ser Asp Lys Asp Lys Arg Lys
        275                 280                 285

Glu Ala Ala Glu Arg Glu Glu Arg Ser Lys Lys Ser Val Ser Ile Asn
    290                 295                 300
```

```
Glu Phe Leu Lys Pro Ala Glu Gly Asp Gly Tyr His Arg Arg Gly Arg
305                 310                 315                 320

Gly Arg Gly Arg Gly Arg Gly Gly Tyr Gly Gly Tyr Gly Met
            325                 330                 335

Asn Asn Ala Ser Ala Pro Ser Ile Glu Asp Pro Asn Gln Phe Pro Ser
            340                 345                 350

Leu Gly Ala Asn
        355

<210> SEQ ID NO 15
<211> LENGTH: 1155
<212> TYPE: DNA
<213> ORGANISM: Beta vulgaris

<400> SEQUENCE: 15
gatggacgag aattatattc gtacttgttt cgctcaatcc ggcgagcttg ttaatgttaa      60
aatcatccgt aataagcaaa ccatgcagtc agagtgctat ggatttattg agttttccac     120
ccatgctgct gctgaaagga ttttgcagac ttacaataac accttgatgc caaatgttga     180
gcaaaactac agactgaatt gggctttcta tggatctggt gagaagcgtg gagaggatgc     240
ttctgattat acaatttttg ttggggattt agctccagat gttactgatt acacattgca     300
agagacattt agagttcgct atccatctgt aaaaggtgct aaggttgtga tagatagact     360
gacaagtaga tcaaagggtt atggatttgt tcgtttcgga gatgaaagtg aacaagcacg     420
tgccatgtca gagatgaatg gaatgatgtg cttaggccgt gcaatgcgta ttggagcagc     480
tgcaaacaag aaaagtgttg gcggaacagc ttcatatcag aataatcagg aactccaaa     540 tgacagtgat ccgagtaaca ctactatatt tgttggcaat ttggattcta atgtgactga     600
tgaacatttg agacaaacat ttagccctta cggagaattg gtccatgtaa aaattcctgc     660
gggcaaacag tgcgggtttg ttcaatttac taacagaagt agtgctgagg aagcattgag     720
ggtattgaac ggaatgcaat taggcggacg aaatgttaga cttcgtgggg gccgtagtcc     780
taacaacaga cagtctcaac ctgaccagaa ccagtggaac aatgctgctt attatggtta     840
tcctcaagga tacgactctt atggatatgt atctgctcct caagacccaa acatgtacta     900
tggtggctac cctggttatg gtggttacgc gatgcctcag caggctcaga tgccattgca     960
acaacagtga tctaccttat gccaagcagg agaggtcggt tgccagggag ctgtcattgt    1020
acttggaggc tgagcttctg gagttggatg attcctccca gagatggcag aatgtagtat    1080
aacttggtca ttgtgctggt cgaattttat ttactgtctt gggttttgc tctgtgctgc    1140 ttttttgtag cttgc                                                    1155

<210> SEQ ID NO 16
<211> LENGTH: 322
<212> TYPE: PRT
<213> ORGANISM: Beta vulgaris

<400> SEQUENCE: 16

Met Asp Glu Asn Tyr Ile Arg Thr Cys Phe Ala Gln Ser Gly Glu Leu
1               5                   10                  15

Val Asn Val Lys Ile Ile Arg Asn Lys Gln Thr Met Gln Ser Glu Cys
            20                  25                  30

Tyr Gly Phe Ile Glu Phe Ser Thr His Ala Ala Ala Glu Arg Ile Leu
        35                  40                  45

Gln Thr Tyr Asn Asn Thr Leu Met Pro Asn Val Glu Gln Asn Tyr Arg
    50                  55                  60
```

-continued

```
Leu Asn Trp Ala Phe Tyr Gly Ser Gly Glu Lys Arg Gly Glu Asp Ala
 65                  70                  75                  80

Ser Asp Tyr Thr Ile Phe Val Gly Asp Leu Ala Pro Asp Val Thr Asp
                 85                  90                  95

Tyr Thr Leu Gln Glu Thr Phe Arg Val Arg Tyr Pro Ser Val Lys Gly
            100                 105                 110

Ala Lys Val Val Ile Asp Arg Leu Thr Ser Arg Ser Lys Gly Tyr Gly
        115                 120                 125

Phe Val Arg Phe Gly Asp Glu Ser Glu Gln Ala Arg Ala Met Ser Glu
    130                 135                 140

Met Asn Gly Met Met Cys Leu Gly Arg Ala Met Arg Ile Gly Ala Ala
145                 150                 155                 160

Ala Asn Lys Lys Ser Val Gly Gly Thr Ala Ser Tyr Gln Asn Asn Gln
                165                 170                 175

Gly Thr Pro Asn Asp Ser Asp Pro Ser Asn Thr Thr Ile Phe Val Gly
            180                 185                 190

Asn Leu Asp Ser Asn Val Thr Asp Glu His Leu Arg Gln Thr Phe Ser
        195                 200                 205

Pro Tyr Gly Glu Leu Val His Val Lys Ile Pro Ala Gly Lys Gln Cys
    210                 215                 220

Gly Phe Val Gln Phe Thr Asn Arg Ser Ser Ala Glu Glu Ala Leu Arg
225                 230                 235                 240

Val Leu Asn Gly Met Gln Leu Gly Gly Arg Asn Val Arg Leu Ser Trp
                245                 250                 255

Gly Arg Ser Pro Asn Asn Arg Gln Ser Gln Pro Asp Gln Asn Gln Trp
            260                 265                 270

Asn Asn Ala Ala Tyr Tyr Gly Tyr Pro Gln Gly Tyr Asp Ser Tyr Gly
        275                 280                 285

Tyr Val Ser Ala Pro Gln Asp Pro Asn Met Tyr Tyr Gly Gly Tyr Pro
    290                 295                 300

Gly Tyr Gly Gly Tyr Ala Met Pro Gln Gln Ala Gln Met Pro Leu Gln
305                 310                 315                 320

Gln Gln

<210> SEQ ID NO 17
<211> LENGTH: 1200
<212> TYPE: DNA
<213> ORGANISM: Beta vulgaris

<400> SEQUENCE: 17
aaaaacctct ttttctctct cctaaatcac acaatggcg atactctcag attacgagga      60
agaagaacac caaccacaac cagaaaagaa gcaaccttca agaaattttt cagcaacttt     120
cgatccttcg aatccgctag ggtttcttca atctactctc gaattcgtct caaaagagtc     180 cgatttttc gctaaggaat catctgcgaa agatgttgtt tctctggttc agaaagtgaa      240
ggagaagtac attgaagaag tagagaataa gaagaagaag cttctagatg aatctgccgc     300
tgccgccgcc gccgccgctg ctgctgctgc gtcgtcgtct tcatctgatt ggagaagaa      360 ggttgatgat aatgagagtg cggaagagac agagaaatct aagtacaaag ctccaaacag     420
tgggaatggt caagatctcg agaactactc atggatacag tccttgcaag aagttactgt     480
taatgttcct gttccacctg aacaaagtc taggtttatc gattgtcaga taagaagaa      540 tcatctgaaa gttggcctca agggtcagcc tcccatcatc gatggtgaac tgttcaagcc     600
tgttaagcca gatgattgtt tttggagttt ggaggatcaa aagtcaatct ctatgctgct     660
```

```
aacaaagcat gatcaaatgg agtggtggag aagtctggtc aaaggtgaac ctgaaatcga    720
cactcagaag gttgaacctg agagcagtaa gctgtctgac ttggaccctg aaacaaggtc    780
aactgttgag aagatgatgt ttgaccaaag gcaaaaatcc atgggcttgc ccacaagtga    840
tgatatgcag aagcaagaca tgctgaagaa gttcatgtcc gagcatccgg aaatggactt    900
ttctaacgcg aagtttaact agatatcgat gtcggtgatg gactatgatt ttttgggtgg    960
caaattctcg aaacaggaac tgaagaaagc ttttgttatg tctaatactg agcttgttca   1020
tagtagttac agtctctagg gtagatgtct catgaagagg ggaacattgc ttttttgttta  1080 actcttattt atatgcaagt gatattcggt ttgctaagca gtacattcgt gcatcctgcg   1140
cttgattcgg gtcctgttca atcatatatg taatgttata gctgcaaaaa aaaaaaaaa    1200
```

<210> SEQ ID NO 18
<211> LENGTH: 295
<212> TYPE: PRT
<213> ORGANISM: Beta vulgaris

<400> SEQUENCE: 18

```
Met Ala Ile Leu Ser Asp Tyr Glu Glu Glu His Gln Pro Gln Pro
 1               5                  10                  15

Glu Lys Lys Gln Pro Ser Lys Lys Phe Ser Ala Thr Phe Asp Pro Ser
                20                  25                  30

Asn Pro Leu Gly Phe Leu Gln Ser Thr Leu Glu Phe Val Ser Lys Glu
            35                  40                  45

Ser Asp Phe Phe Ala Lys Glu Ser Ser Ala Lys Asp Val Val Ser Leu
        50                  55                  60

Val Gln Lys Val Lys Glu Lys Tyr Ile Glu Glu Val Glu Asn Lys Lys
 65                  70                  75                  80

Lys Lys Leu Leu Asp Glu Ser Ala Ala Ala Ala Ala Ala Ala
                85                  90                  95

Ala Ala Ala Ser Ser Ser Ser Asp Leu Glu Lys Lys Val Asp Asp
            100                 105                 110

Asn Glu Ser Ala Glu Glu Thr Glu Lys Ser Lys Tyr Lys Ala Pro Asn
        115                 120                 125

Ser Gly Asn Gly Gln Asp Leu Glu Asn Tyr Ser Trp Ile Gln Ser Leu
    130                 135                 140

Gln Glu Val Thr Val Asn Val Pro Val Pro Pro Gly Thr Lys Ser Arg
145                 150                 155                 160

Phe Ile Asp Cys Gln Ile Lys Lys Asn His Leu Lys Val Gly Leu Lys
                165                 170                 175

Gly Gln Pro Pro Ile Ile Asp Gly Glu Leu Phe Lys Pro Val Lys Pro
            180                 185                 190

Asp Asp Cys Phe Trp Ser Leu Glu Asp Gln Lys Ser Ile Ser Met Leu
        195                 200                 205

Leu Thr Lys His Asp Gln Met Glu Trp Trp Arg Ser Leu Val Lys Gly
    210                 215                 220

Glu Pro Glu Ile Asp Thr Gln Lys Val Glu Pro Glu Ser Ser Lys Leu
225                 230                 235                 240

Ser Asp Leu Asp Pro Glu Thr Arg Ser Thr Val Glu Lys Met Met Phe
                245                 250                 255

Asp Gln Arg Gln Lys Ser Met Gly Leu Pro Thr Ser Asp Asp Met Gln
            260                 265                 270
```

```
Lys Gln Asp Met Leu Lys Lys Phe Met Ser Glu His Pro Glu Met Asp
            275                 280                 285

Phe Ser Asn Ala Lys Phe Asn
    290                 295
```

<210> SEQ ID NO 19
<211> LENGTH: 1050
<212> TYPE: DNA
<213> ORGANISM: Mus musculus

<400> SEQUENCE: 19

```
gaaagagag  gagagagaaa  accaaaatca  acaaaaatgg  cggaacatct  agcatcgata    60
ttcgggacag  agaaagacag  agtgaactgt  ccattctact  tcaagatcgg  agcttgtaga   120
catggagatc  gttgctcaag  gcttcatact  aagcctagta  ttagccctac  tttgttgctt   180
gctaatatgt  atcaacgccc  tgatatgatt  actcctggtg  ttgatcctca  aggacagcct   240
cttgatcctc  gcaaaattca  acaacatttt  gaggattttt  atgaggattt  atttgaggaa   300
ctaagcaagt  atggggagat  tgaaagtctc  aacatctgtg  acaatttggc  tgaccacatg   360
gttgggaatg  tttatgtgca  gttcagagag  aagaacatg   ctggcgaggc  actacgaaac   420
ttgagtggaa  gattttatgc  cggtcgtcca  atcattgttg  attttctcc   tgtaacggac   480
tcagagaag   caacctgcag  acagtatgag  gaaaatgtgt  gcaatcgtgg  aggttactgc   540
aactttatgc  atttgaaaaa  aattagcagg  gagcttaggc  gacagttgtt  tggaaggtac   600
agaaggaggc  atagccgtag  tagaagtcgc  agtcctcaag  cacatcgggg  gcatggagat   660
cgtccacatg  gtggccgtgg  ttatggtaga  agagatgatg  atagaaatca  gcggtaccat   720
gacaagggaa  gaaggcctag  aagccgtagc  cctgggcata  gaggacgaag  cagaagccct   780
cccggcagga  gggataggag  tccagtgagg  gagaatagtg  aggagagaag  agcaaagatt   840
gcacaatgga  acagggaaaa  ggaacaggca  gacactggta  taacgatgt   taatcatgat   900
gtcactgaca  accatgcaaa  tggatttcag  gacaatgggg  aggattacta  tgaccatcct   960
cagcagtaac  tggatgaagt  gcacaagcag  gcttattca   ctacttctgg  tttgctgtta  1020
tcagagtctg  ctcgtttgca  ggatttttcg                                     1050
```

<210> SEQ ID NO 20
<211> LENGTH: 310
<212> TYPE: PRT
<213> ORGANISM: Mus musculus

<400> SEQUENCE: 20

```
Met Ala Glu His Leu Ala Ser Ile Phe Gly Thr Glu Lys Asp Arg Val
 1               5                  10                  15

Asn Cys Pro Phe Tyr Phe Lys Ile Gly Ala Cys Arg His Gly Asp Arg
                20                  25                  30

Cys Ser Arg Leu His Thr Lys Pro Ser Ile Ser Pro Thr Leu Leu Leu
            35                  40                  45

Ala Asn Met Tyr Gln Arg Pro Asp Met Ile Thr Pro Gly Val Asp Pro
        50                  55                  60

Gln Gly Gln Pro Leu Asp Pro Arg Lys Ile Gln Gln His Phe Glu Asp
65                  70                  75                  80

Phe Tyr Glu Asp Leu Phe Glu Glu Leu Ser Lys Tyr Gly Glu Ile Glu
                85                  90                  95

Ser Leu Asn Ile Cys Asp Asn Leu Ala Asp His Met Val Gly Asn Val
            100                 105                 110
```

```
Tyr Val Gln Phe Arg Glu Glu His Ala Gly Glu Ala Leu Arg Asn
        115                 120                 125

Leu Ser Gly Arg Phe Tyr Ala Gly Arg Pro Ile Ile Val Asp Phe Ser
    130                 135                 140

Pro Val Thr Asp Phe Arg Glu Ala Thr Cys Arg Gln Tyr Glu Glu Asn
145                 150                 155                 160

Val Cys Asn Arg Gly Gly Tyr Cys Asn Phe Met His Leu Lys Lys Ile
                165                 170                 175

Ser Arg Glu Leu Arg Arg Gln Leu Phe Gly Arg Tyr Arg Arg His
        180                 185                 190

Ser Arg Ser Arg Ser Arg Ser Pro Gln Ala His Arg Gly His Gly Asp
        195                 200                 205

Arg Pro His Gly Gly Arg Gly Tyr Gly Arg Arg Asp Asp Arg Asn
        210                 215                 220

Gln Arg Tyr His Asp Lys Gly Arg Arg Pro Arg Ser Arg Ser Pro Gly
225                 230                 235                 240

His Arg Gly Arg Ser Arg Ser Pro Pro Gly Arg Arg Asp Arg Ser Pro
                245                 250                 255

Val Arg Glu Asn Ser Glu Glu Arg Arg Ala Lys Ile Ala Gln Trp Asn
        260                 265                 270

Arg Glu Lys Glu Gln Ala Asp Thr Gly Asn Asn Asp Val Asn His Asp
        275                 280                 285

Val Thr Asp Asn His Ala Asn Gly Phe Gln Asp Asn Gly Glu Asp Tyr
        290                 295                 300

Tyr Asp His Pro Gln Gln
305                 310

<210> SEQ ID NO 21
<211> LENGTH: 117
<212> TYPE: PRT
<213> ORGANISM: Arabidopsis thaliana

<400> SEQUENCE: 21

Met Val Thr Thr Pro His Glu Lys Ala Thr Asp Ser Lys Lys Ser Gly
1               5                   10                  15

Thr Glu Ser Asn Ser Gln Pro Ile Val Gly Asp Ser Ser Tyr Glu Arg
            20                  25                  30

Ser Lys Val Gly Asp Arg Glu Arg Glu Ser Asp Arg Glu Lys Glu Arg
        35                  40                  45

Gly Arg Glu Arg Asp Arg Gly Arg Ser His Arg Gly Arg Asp Ser Asp
    50                  55                  60

Arg Asp Ser Asp Arg Glu Arg Asp Lys Leu Lys Asp Arg Ser His His
65                  70                  75                  80

Arg Ser Arg Asp Arg Leu Lys Asp Ser Gly Gly His Ser Asp Lys Ser
                85                  90                  95

Arg His His Ser Ser Arg Asp Arg Asp Tyr Arg Asp Ser Ser Lys Asp
            100                 105                 110

Arg Arg Arg His His
        115

<210> SEQ ID NO 22
<211> LENGTH: 55
<212> TYPE: PRT
<213> ORGANISM: Arabidopsis thaliana
```

-continued

```
<400> SEQUENCE: 22

Met Ile Tyr Thr Ala Ile Asp Asn Phe Tyr Leu Thr Asp Glu Gln Leu
 1               5                  10                  15

Lys Ala Ser Pro Ser Arg Lys Asp Gly Ile Asp Glu Thr Thr Glu Ile
            20                  25                  30

Ser Leu Arg Ile Tyr Gly Cys Asp Leu Ile Gln Glu Gly Gly Ile Leu
        35                  40                  45

Leu Lys Leu Pro Gln Ala Val
     50                  55

<210> SEQ ID NO 23
<211> LENGTH: 17
<212> TYPE: DNA
<213> ORGANISM: Artificial Sequence
<220> FEATURE:
<223> OTHER INFORMATION: Description of Artificial Sequence:Probe or
      Primer

<400> SEQUENCE: 23
catcaaatct ttcaggg                                                      17

<210> SEQ ID NO 24
<211> LENGTH: 18
<212> TYPE: DNA
<213> ORGANISM: Artificial Sequence
<220> FEATURE:
<223> OTHER INFORMATION: Description of Artificial Sequence:Probe or
      Primer

<400> SEQUENCE: 24
ctttatttta ctgtacag                                                     18
```